US009499496B2

(12) United States Patent
Golden et al.

(10) Patent No.: US 9,499,496 B2
(45) Date of Patent: Nov. 22, 2016

(54) INHIBITORS OF RESPIRATORY SYNCYTIAL VIRUS

(71) Applicants: University of Kansas, Lawrence, KS (US); Southern Research Institute, Birmingham, AL (US)

(72) Inventors: Jennifer E. Golden, Olathe, KS (US); Jeffrey Aube, Lawrence, KS (US); Denise S. Simpson, Lawrence, KS (US); Daniel P. Flaherty, Overland Park, KS (US); Daljit S. Matharu, Lawrence, KS (US); William E. Severson, Louisville, KY (US); Lynn Rasmussen, Odenville, AL (US)

(73) Assignees: University of Kansas, Lawrence, KS (US); Southern Research Institute, Birmingham, AL (US)

( * ) Notice: Subject to any disclaimer, the term of this patent is extended or adjusted under 35 U.S.C. 154(b) by 0 days.

(21) Appl. No.: 14/405,772

(22) PCT Filed: Jun. 5, 2013

(86) PCT No.: PCT/US2013/044321
§ 371 (c)(1),
(2) Date: Dec. 4, 2014

(87) PCT Pub. No.: WO2013/184806
PCT Pub. Date: Dec. 12, 2013

(65) Prior Publication Data
US 2015/0119411 A1    Apr. 30, 2015

Related U.S. Application Data

(60) Provisional application No. 61/655,781, filed on Jun. 5, 2012, provisional application No. 61/655,778, filed on Jun. 5, 2012.

(51) Int. Cl.
| | |
|---|---|
| *C07D 239/96* | (2006.01) |
| *C07D 405/12* | (2006.01) |
| *C12N 7/00* | (2006.01) |
| *A61K 31/517* | (2006.01) |

(52) U.S. Cl.
CPC .......... *C07D 239/96* (2013.01); *A61K 31/517* (2013.01); *C07D 405/12* (2013.01); *C12N 7/00* (2013.01); *C12N 2760/18563* (2013.01)

(58) Field of Classification Search
CPC .................................................. A01K 31/50
See application file for complete search history.

(56) References Cited

U.S. PATENT DOCUMENTS

| | | |
|---|---|---|
| 2004/0142953 A1 | 7/2004 | Delorme et al. |
| 2005/0288282 A1 | 12/2005 | Delorme et al. |
| 2009/0163545 A1 | 6/2009 | Goldfarb |

FOREIGN PATENT DOCUMENTS

| | | |
|---|---|---|
| FR | 2943673 | 10/2010 |
| FR | 2944206 | 10/2010 |
| WO | WO 03/024448 | 3/2003 |
| WO | WO 2008/112715 | 9/2008 |
| WO | WO 2008/113255 | 9/2008 |
| WO | WO 2009/077680 | 6/2009 |
| WO | WO 2009/155001 | 12/2009 |
| WO | WO 2010/109148 | 9/2010 |
| WO | WO 2010/116090 | 10/2010 |

OTHER PUBLICATIONS

Andries, K.; et, al. 2003. Substituted benzimidazoles with nanomolar activity against respiratory syncytial virus. Antiviral Res. 60, 209-219.
Berge et al, 1977, "Pharmaceutically Acceptable Salts." J. Pharm. Sci. vol. 66, pp. 1-19.
Bonavia, A.;Franti, M.; Keaney, E.P.; Kuhen, K.; Seepersaud, M.; Radetich, B.; Shao, J.; Honda, A.; Dewhurst, J.; Monroe, J.; Wolff, K.; Osborne, C.; Lanieri, L.; Hoffmaster, K.; Amin, J.; Markovits, J.; Broome, M.; Skuba, E.; Cornella-Taracido, I.; Joberty, G.; Bouwmeester, T.; Hamann, L.; Tallarico, J.A.; Tommasi, R.; Compton, T.; Sushell, S.M. 2011. Organic Synthesis Toward Small-Molecule Probes and Drugs Special Feature: Identification of broad-spectrum antiviral compounds and assessment of the druggability of their target for efficacy against respiratory syncytial virus (RSV) PNAS, 6739-6744.
Bonfanti J-F, et al. 2007 Selection of a respiratory syncytial virus fusion inhibitor clinical candidate, part 1: Improving the pharmacokinetic profile using the structure property relationship. J Med Chem 50:4572-4584.
Byrd and Prince. (1997) Animal Models of Respiratory Syncytial Virus Infection. Clinical Infectious Diseases 25:1363-8.
Carter, M.C., et. al. 2006. 1,4-Benzodiazepines as inhibitors of respiratory syncytial virus. J. Med. Chem. 2006, 49, 2311-2319.
Chen, B.; Dodge, M.E.; Tang, W., et al., "Small molecule-mediated disruption of Wnt-dependent signaling in tissue regeneration and cancer." Nature Chemical Biology 2009, 5(2), 100-107.
Cianci, C.; Genovesi, E.V.; Lamb, L.; Medina, I.; et al. 2004. Oral efficacy of a respiratory syncycial virus inhibitor in rodent models of infection. Antimicrob. Agents Chemother. 48:2448-2454.
Cianci, C.; Yu, K.L.; Combrink, K.; Sin, N.; et al. 2004. Orally active fusion inhibitors of syncycial virus. Antimicrob. Agents Chemother. 48:413-422.
Combrink et al., "Respiratory syncytial virus fusion inhibitors. Part 6: An examination of the effect of structural variation of the benzimidazol-2-one heterocycle moiety," Bioorganic & Medical Chemistry Letters, Pergamon, Elsevier Science, GB, vol. 17, No. 17, Aug. 4, 2007, pp. 4784-4790.
Database CA [Online] Chemical Abstracts Service, Columbus, Ohio, US; 2009, Goldfarb, "Method using lifespan-altering compounds for altering the lifespan of eukaryotic organisms, and screening for such compounds."
Database Registry [Online] Chemical Abstracts Service, Columbus, Ohio, US; Aug. 9, 2006.

(Continued)

*Primary Examiner* — Paul V Ward
(74) *Attorney, Agent, or Firm* — Michael Best & Friedrich LLP

(57) ABSTRACT

Described herein are compounds, pharmaceutical compositions and methods for treating a respiratory syncytial virus infection in a subject, or for inhibiting replication of respiratory syncytial virus.

43 Claims, 25 Drawing Sheets

(56) References Cited

OTHER PUBLICATIONS

Douglas, J. L., M. L. Panis, E. Ho, K. Y. Lin, S. H. Krawczyk, D. M. Grant, R. Cai, S. Swaminathan, and T. Cihlar. 2003 Inhibition of respiratory syncytial virus fusion by the small molecule VP-14637 via specific interactions with F protein. J Virol 77:5054-64.

Douglas, J.L. 2004, In search of a small-molecule inhibitor for respiratory syncytial virus. Expert Rev. Anti-infect. Ther. 2:625-639.

Douglas, J.L., et al. Small Molecules VP-14637 and JNJ-2408068 Inhibit Respiratory Syncytial Virus Fusion by Similar Mechanisms. 2005. Antimicrobial Agents and Chemotherapy, 49: 2460-2466.

Gopinathan, S., Nouraldeen, A., Wilson, A.G.E. Development and application of a highthroughput formulation screening strategy for oral administration in drug discovery. Future Med. Chem. (2010) 2(9), 1391-1398.

Hall, C. B., E. E. Walsh, J. F. Hruska, R. F. Betts, and W. J. Hall. 1983. Ribavirin treatment of experimental respiratory syncytial viral infection. A controlled double-blind study in young adults. JAMA 249:2666-70.

Hall, C. B., J. T. McBride, E. E. Walsh, D. M. Bell, C. L. Gala, S. Hildreth, L. G. Ten Eyck, and W. J. Hall. 1983. Aerosolized ribavirin treatment of infants with respiratory syncytial viral infection. A randomized double-blind study. N Engl J Med 308:1443-7.

Higuchi, T. and Stella, V., Pro-drugs as Novel Delivery Systems, V. 14 of the A.C.S. Symposium Series (1975).

Hruska, J. F., J. M. Bernstein, R. G. Douglas, Jr., and C. B. Hall. 1980. Effects of ribavirin on respiratory syncytial virus in vitro. Antimicrob Agents Chemother 17:770-5.

Hruska, J. F., P. E. Morrow, S. C. Suffin, and R. G. Douglas, Jr. 1982. In vivo inhibition of respiratory syncytial virus by ribavirin. Antimicrob Agents Chemother 21:125-30.

Huntley, C.C.; Weiss, W.J. Gazumyan, A.; Buklan, A.; Feld, B.; Hu, W.; Jones, T.R.; Murphy, T.; Nikitenko, A.A.; O'Hara, B.; Prince, G.; Quartuccio, S.; Raifeld, Y.E.; Wyde, P.; O'Connell, J.F. 2002. RFI-641, a Potent Respiratory Syncycial Virus Inhibitor. Antimicrob. Agents Chemother. 46:841-847.

Ibrahim F, El-Din MK, Eid MI, Wahba ME. 2011. Validated stability-indicating spectrofluorimetric methods for the determination of ebastine in pharmaceutical preparations. Chem Cent J. 5(1):11.

International Search Report and Written Opinion for Application No. PCT/US2013/044321 dated Jul. 31, 2013 (12 pages).

Leyssen, P., et al. The predominant mechanism by which ribavirin exerts its antiviral activity in vitro against flaviviruses and paramyxoviruses is mediated by inhibition of IMP dehydrogenase. J Virol, 2005. 79(3): p. 1943-7. PMID: 15650220.

Noah, J.W.; Severson, W.; Chung, D.H.; Moore, B.; Jia, F.; Xu, X.; Maddox, C.; Lynn Rasmussen, L.; Sosa M.I.; Tower, N.A.; Ananthan, S.; White, E.L.; Jonsson, C.; Matharu, D.S.; Golden, J.E.; Prisinzano, T.E.; Aubé, J. "A Cell Based HTS Approach for the Discovery of New Inhibitors of RSV." Probe Report from the NIH Molecular Libraries Program [Internet]. Bethesda (MD): National Center for Biotechnology Information (US); 2011, Probe ML232.

Olszewska W, Openshaw P. 2009. Emerging drugs for respiratory syncytial virus infection.Expert Opin Emerg Drugs. 14(2):207-17.

Ossman et al., "Synthesis of some new 4(3H)-quinazolinones as potential anticonvulsants," Saudi Pharmaceutical Journal, 2(1), 1994, pp. 21-31.

Prescott, Ed., Methods in Cell Biology, vol. XIV, Academic Press, New York, N. Y., (1976), p. 33 et seq.

Razinkov, V., A. Gazumyan, A. Nikitenko, G. Ellestad, and G. Krishnamurthy. 2001. RFI-641 inhibits entry of respiratory syncytial virus via interactions with fusion protein. Chem Biol 8:645-59.

Rouan, M.C., Gevers, T., Roymans, D., de Zwart, L., Nauwelaers. D., De Meulder, M., van Remoortere, P., Vanstockem, M., Koul, A., K. Simmen, and K. Andries. 2010. Pharmacokinetic-pharmacodynamics of a respiratory syncytial virus fusion inhibitor in the cotton rat model. Antimicro. Agents Chemother. 54:4543-39.

Sudo, K., Y. Miyazaki, N. Kojima, M. Kobayashi, H. Suzuki, M. Shintani, and Y. Shimizu 2005. YM-53403, a unique anti-respiratory syncytial virus agent with a novel mechanism of action. Antiviral Res 65:125-31.

Taber, L. H., V. Knight, B. E. Gilbert, H. W. McClung, S. Z. Wilson, H. J. Norton, J. M. Thurson, W. H. Gordon, R. L. Atmar, and W. R. Schlaudt. 1983. Ribavirin aerosol treatment of bronchiolitis associated with respiratory syncytial virus infection in infants. Pediatrics 72:613-8.

Wyde, P.R.; Laquerre, S.; Chetty, S.N.; Gilbert, B.E.; Nitz, T.J.; Pevear, D.C.; 2005. Antiviral efficacy of VP14637 against respiratory syncycial virus in vitro and in cotton rats following delivery by small droplet aerosol. Antiviral Res. 68:18-26.

Yu, K.L.; Zhang, Y.; Civiello, R.L.; et al. 2004. Respiratory syncycial virus inhibitors. Part 2. Benzimidazole-2-one derivatives. Bioorg. Med. Chem. Lett. 14:1133-1137.

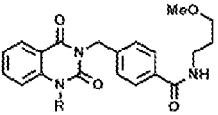

| Entry | R | P or S | n | EC$_{50}$ µM | EC$_{50}$ STDEV | n | CC$_{50}$ µM | CC$_{50}$ STDEV | Selectivity Index (CC$_{50}$/EC$_{50}$) | Plaque Reduction Assay (log reduction) at 10 µM |
|---|---|---|---|---|---|---|---|---|---|---|
| 1 | CH$_2$-4-methyl-phenyl | S | 3 | 2.5 | ± 0.75 | 2 | 69 | ± 3.0 | 27.6 | 4.15 |
| 2 | CH$_2$-4-methyl-phenyl | P | 3 | 1.77 | ± 0.08 | 2 | >50 | NA | 28.2 | NT |
| 3 | methyl | S | 3 | >50 | NA | 2 | 15.65 | ± 0.35 | NA | NT |
| 4 | n-propyl | S | 3 | >50 | NA | 2 | 18.95 | ± 9.12 | NA | NT |
| 5 | CH$_2$-cyclohexyl | S | 3 | >50 | NA | 2 | < 1.6 | NA | NA | 1.84 |
| 6 | CH$_2$-phenyl | S | 3 | > 50 | NA | 2 | > 50 | NA | N/A | NT |
| 7 | CH$_2$CH$_2$-4-Br-phenyl | S | 3 | >50 | NA | 2 | < 1.6 | NA | NA | 3.28 |
| 8 | CH$_2$CH$_2$-4-Me-phenyl | S | 3 | >50 | NA | 2 | < 1.6 | NA | NA | 3.95 |
| 9 | CH$_2$CH$_2$-4-CF$_3$-phenyl | S | 3 | >50 | NA | 2 | 116.1 | ± 0.7 | NA | 0.57 |
| 10 | CH$_2$-2-Br-phenyl | S | 3 | >50 | NA | 2 | 8.21 | ± 0.17 | N/A | NT |
| 11 | CH$_2$-3-Br-phenyl | S | 3 | 2.24 | ± 0.09 | 2 | 3.76 | ± 0.38 | 1.7 | NT |
| 12 | CH$_2$-4-Br-phenyl | S | 6 | 0.85 | ± 0.15 | 4 | 98.85 | ± 8.70 | 118.9 | 4.07 |
| 13 | CH$_2$-2-F-phenyl | S | 3 | >50 | NA | 2 | 7.63 | ± 0.97 | N/A | NT |
| 14 | CH$_2$-4-F-phenyl | S | 3 | 5.05 | ± 0.37 | 2 | 7.57 | ± 0.22 | 1.5 | NT |

P = purchased; S = synthesized; NA = not applicable; NT = not tested

FIG. 3

| Entry | R | P or S | CPE Assay Potency (μM) mean (n = # replicates) | | | Cytotoxicity Assay Potency (μM) mean (n = # replicates) | | | Selectivity Index (CC$_{50}$/EC$_{50}$) | Plaque Reduction Assay (log reduction) at 10 μM |
|---|---|---|---|---|---|---|---|---|---|---|
| | | | n | EC$_{50}$ μM | EC$_{50}$ STDEV | n | CC$_{50}$ μM | CC$_{50}$ STDEV | | |
| 15 | CH$_2$-4-Cl-phenyl | S | 6 | 6.71 | ± 1.92 | 4 | 120.50 | ± 7.78 | 17.9 | 3.12 |
| 16 | CH$_2$-4-MeO-phenyl | S | 6 | 2.02 | ± 0.91 | 4 | 96.60 | ± 1.56 | 48.5 | 2.72 |
| 17 | CH$_2$-4-NO$_2$-phenyl | S | 6 | 0.60 | ± 0.03 | 4 | 106.00 | ± 4.24 | 175.8 | 4.94 |
| 18 | CH$_2$-4-NO$_2$-phenyl | S | 3 | 0.54 | ± 0.03 | 2 | >150 | NA | 278.0 | > 6.18 |
| 19 | CH$_2$-4-CF$_3$-phenyl | S | 6 | 1.32 | ± 0.06 | 4 | 103.65 | ± 10.39 | 78.8 | 2.66 |
| 20 | CH$_2$-4-CN-phenyl | S | 3 | 1.62 | ± 0.15 | 2 | 12.54 | ± 1.19 | 7.7 | 9.90 |
| 21 | CH$_2$-4-ethyl-phenyl | S | 3 | 1.00 | ± 0.05 | 2 | 94.85 | ± 3.75 | 94.9 | 5.90 |
| 22 | CH$_2$-4-$i$-Pr-phenyl | S | 3 | 0.81 | ± 0.75 | 2 | > 200 | NA | >247 | 6.70 |
| 23 | CH$_2$-(5-(benzooxa-diazole) | S | 9 | 4.92 | ± 0.70 | 4 | 126.50 | ± 7.78 | 26.1 | 2.05 |
| 24 | CH$_2$-3-(5-methylisoxa-zole) | S | 3 | >50 | NA | 2 | 7.73 | ± 0.7 | NA | NT |
| 25 | CH$_2$-3-CF$_3$,4-Me-phenyl | S | 6 | 1.49 | ± 0.91 | 4 | 79.60 | ± 2.40 | 57.1 | 2.37 |
| 26 | CH$_2$-2-pyridyl | S | 3 | >50 | NA | 2 | 16.00 | ± 0.33 | NA | 0.12 |
| 27 | CH$_2$-3-pyridyl | S | 3 | >50 | NA | 2 | 8.00 | ± 0.32 | NA | 0.85 |

P = purchased; S = synthesized; NA = not applicable; NT = not tested

FIG. 3 (cont'd)

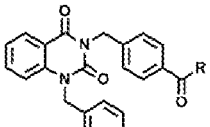

| Entry | R | P or S | CPE Assay Potency (μM) mean (n = # replicates) | | | Cytotoxicity Assay Potency (μM) mean (n = # replicates) | | | Selectivity Index (CC$_{50}$/EC$_{50}$) | Plaque Reduction Assay (log reduction) at 10 μM |
|---|---|---|---|---|---|---|---|---|---|---|
| | | | n | EC$_{50}$ μM | EC$_{50}$ STDEV | n | CC$_{50}$ μM | CC$_{50}$ STDEV | | |
| 1 | NH(CH$_2$)$_3$OCH$_3$ | P | 3 | 1.77 | ± 0.08 | 2 | >50 | NA | 28.22 | NT |
| 2 | NH(CH$_2$)$_3$OCH$_3$ | S | 3 | 2.5 | ± 0.75 | 2 | 69 | ± 3.0 | 27.60 | 4.15 |
| 3 | NH(CH$_2$)$_3$OCH$_2$CH$_3$ | S | 3 | 1.92 | ± 0.18 | 2 | 8.47 | ± 0.25 | 4.44 | NT |
| 4 | NH(CH$_2$)$_3$OCH(CH$_3$)$_2$ | S | 3 | 1.99 | ± 0.15 | 2 | 19.28 | ± 0.85 | 9.75 | NT |
| 5 | NH(CH$_2$)$_3$NMe$_2$ | S | 3 | 9.46 | ± 0.44 | 2 | 16.63 | ± 1.48 | 1.76 | NT |
| 6 | NH(CH$_2$)$_4$OCH$_3$ | S | 3 | 0.83 | ± 0.05 | 2 | 6.50 | ± 0.30 | 7.83 | 2.10 |
| 7 | NH(CH$_2$)$_2$OCH$_3$ | S | 3 | 2.21 | ± 1.40 | 2 | >50 | NA | 22.70 | NT |
| 8 | NHCH$_2$-(3-oxetane) | S | 3 | 0.71 | ± 0.13 | 2 | 46.96 | ± 1.9 | 66.14 | 5.10 |
| 9 | NHCH$_2$-cyclobutane | S | 3 | 0.96 | ± 0.08 | 2 | 7.57 | ± 0.30 | 7.89 | 1.20 |
| 10 | morpholine | S | 3 | >50 | NA | 2 | 17.5 | ± 1.13 | NA | NT |
| 11 | pyrrolidine | S | 3 | >50 | NA | 2 | 5.37 | ± 0.33 | NA | NT |
| 12 | piperidine | S | 3 | >50 | NA | 2 | 7.34 | ± 1.25 | NA | NT |
| 13 | NHCH$_3$ | S | 3 | 2.15 | ± 0.91 | 2 | 45.3 | ± 1.7 | 21.10 | NT |
| 14 | N(CH$_3$)$_2$ | S | 3 | >50 | NA | 2 | 10.06 | ± 0.2 | NA | NT |

P = purchased; S = synthesized; NA = not applicable; NT = not tested

FIG. 4

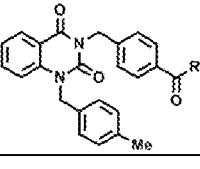

| Entry | R | P or S | CPE Assay Potency (µM) mean (n = # replicates) | | | Cytotoxicity Assay Potency (µM) mean (n = # replicates) | | | Selectivity Index (CC₅₀/EC₅₀) | Plaque Reduction Assay (log reduction) at 10 µM |
|---|---|---|---|---|---|---|---|---|---|---|
| | | | n | EC₅₀ µM | EC₅₀ STDEV | n | CC₅₀ µM | CC₅₀ STDEV | | |
| 15 | NH-*tert*-butyl | S | 3 | 0.70 | ± 0.03 | 2 | 8.42 | ± 0.28 | 12.09 | 5.54 |
| 16 | NH-cyclohexyl | S | 3 | >50 | NA | 2 | >50 | NA | NA | NT |
| 17 | NH-phenyl | S | 3 | >50 | NA | 2 | >50 | NA | NA | NT |
| 18 | NHCH₂-phenyl | S | 3 | >50 | NA | 2 | 41.8 | ± 7.92 | NA | NT |
| 19 | NHCH₂-2-furyl | S | 3 | >50 | NA | 2 | >50 | NA | NA | NT |
| 20 | NH-4-(2-methylquinoline) | S | 3 | >50 | NA | 2 | >50 | NA | 1.00 | 0.61 |
| 21 | NH-2-thiazole | S | 3 | >50 | NA | 2 | >50 | NA | 1.00 | 0.01 |
| 22 | NH-4-pyridyl | S | 3 | 1.04 | ± 0.04 | 2 | >50 | NA | 48.21 | 3.50 |

P = purchased; S = synthesized; NA = not applicable; NT = not tested

FIG. 4 (cont'd)

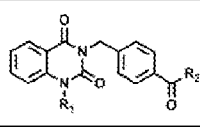

| Entry | R₁ | R₂ | P or S | n | EC$_{50}$ μM | EC$_{50}$ STDEV | n | CC$_{50}$ μM | CC$_{50}$ STDEV | Selectivity Index (CC$_{50}$/EC$_{50}$) | Plaque Reduction Assay (log reduction) at 10 μM | Media Solubility and PBS Solubility μM |
|---|---|---|---|---|---|---|---|---|---|---|---|---|
| 1[a] | CH$_2$-4-Me-phenyl | NH(CH$_2$)$_3$-OCH$_3$ | P | 3 | 1.77 | ± 0.08 | 2 | >50 | NA | 28.22 | NT | 2.54 / 0.13 |
| 2[a] | CH$_2$-4-Me-phenyl | NH(CH$_2$)$_3$-OCH$_3$ | S | 3 | 2.5 | ± 0.75 | 2 | 69 | ± 3.0 | 27.60 | 4.15 | NT |
| 3 | CH$_2$-4-NO$_2$-phenyl | NHCH$_2$-3-oxetane | S | 3 | 1.32 | ± 0.05 | 2 | >50 | ± 2.9 | 37.88 | > 6.18 | 7.19 / 1.44 |
| 4 | CH$_2$-4-CO$_2$H-phenyl | NHCH$_2$-3-oxetane | S | 3 | >50 | NA | 2 | >150 | NA | NA | NT | NT / 98.1 |
| 5 | CH$_2$-4-i-propyl-phenyl | NHCH$_2$-3-oxetane | S | 3 | 0.40 | ± 0.01 | 2 | 3.6 | 0.08 | 9.00 | 5.75 | NT |
| 6 | CH$_2$-4-tert-butyl-phenyl | NHCH$_2$-3-oxetane | S | 3 | 1.65 | ± 0.08 | 2 | 3.73 | 0.28 | 2.26 | 3.40 | NT |
| 7 | CH$_2$-4-NMe$_2$-phenyl | NHCH$_2$-3-oxetane | S | 3 | 1.07 | ± 0.22 | 2 | 44.73 | 7.2 | 41.80 | > 6.18 | 18.45 / 11.23 |
| 8 | CH$_2$-4-Cl-phenyl | NHCH$_2$-2-furyl | P | 3 | 0.82 | ± 0.01 | 2 | 151.62 | ± 11.78 | 184.90 | NT | 10.20 / NT |
| 9 | CH$_2$-4-i-propyl-phenyl | NHCH$_2$-2-furyl | S | 3 | 1.23 | ± 0.11 | 2 | >150 | NA | 122.00 | 2.83 | NT / 0.26 |
| 10 | CH$_2$-4-Br-phenyl | NH-4-pyridyl | S | 3 | 1.28 | NA | 2 | < 1.56 | NA | NA | 1.00 | NT / 0.52 |
| 11 | CH$_2$-4-i-propyl-phenyl | NH-3-MeO-4-pyridyl | S | 3 | 0.48 | ± 0.06 | 2 | <1.56 | NA | NA | NT | NT |

P = purchased; S = synthesized; NA = not applicable; NT = not tested

FIG. 5

INHIBITORS OF RESPIRATORY SYNCYTIAL VIRUS

CROSS-REFERENCE TO RELATED APPLICATIONS

This application claims priority to U.S. Provisional Patent Application No. 61/655,778, filed on Jun. 5, 2012, and U.S. Provisional Patent Application No. 61/655,781, filed on Jun. 5, 2012, the entire contents of each of which are hereby incorporated by reference.

STATEMENT REGARDING FEDERALLY SPONSORED RESEARCH

This invention was made with U.S. Government support awarded by the National Institutes of Health, Grant Nos. U54-HG005031, U54-HG005034-01, and 1-R03-MH082403-01A1. The U.S. Government has certain rights in this invention.

BACKGROUND

Respiratory Syncytial Virus (RSV) was discovered approximately 40 years ago, and was initially isolated from chimpanzees during an epizootic upper respiratory tract disease outbreak. RSV, which belongs to the family Paramyxoviridae, was subsequently found to be the most important cause of infectious pulmonary disease in human infants, and is a major causative agent of respiratory tract infections among children worldwide. Most children will be infected with RSV prior to their second birthday, leading to 75,000-125,000 hospitalizations and medical costs exceeding $650 million annually. Infants, immunocompromised children, or those with underlying respiratory disorders are at a particularly high risk of developing severe and lethal RSV respiratory tract infections that can be complicated by the resultant viral pneumonia and respiratory distress. Elderly and immune-compromised individuals are also susceptible to severe respiratory infections, thereby highlighting the importance of medical intervention in the form of early diagnosis and implementation of supportive or antiviral therapies.

There are only two FDA-approved drugs for use in patients having or at risk of RSV infection. Ribavirin is a nucleoside analog used for therapeutic intervention, which suffers from toxic liabilities that limit its use particularly in infants and children. SYNAGIS® (palivizumab) is a humanized monoclonal antibody to RSV. However it is expensive, used only for prophylaxis, and requires monthly injections. It is generally limited to use in high-risk pediatric patients. Due to the lack of a vaccine and the presence of toxicological limitations in existing therapies, there is substantial need for effective treatments with an improved profile.

While several small molecules have been developed for potential use in the treatment of RSV, all to date have failed to yield positive clinical results. Most of these small molecules appear to fall under the category of entry inhibitors which may result in the emergence of resistance. Therefore, the identification of a novel chemotype with an improved profile of efficacy and safety as compared to ribavirin may provide a stage for further development and better treatment options.

SUMMARY

In one aspect, the disclosure provides a method of treating a respiratory syncytial virus infection, comprising administering to a subject in need of treatment a therapeutically effective amount of a compound of formula (I):

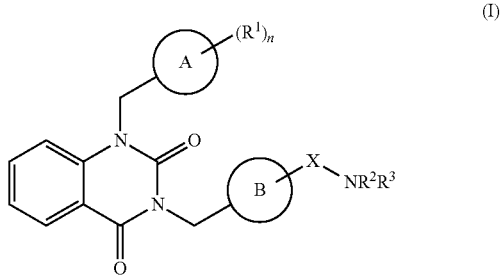

wherein:
A and B are each independently aryl, heteroaryl, cycloalkyl or heterocycle;
n is 0, 1, 2, 3, 4 or 5;
$R^1$ is selected from the group consisting of alkyl, halo, nitro, cyano, haloalkyl, amino, alkoxy, —$SO_2H$, —$SO_2NHR'$, $CONHR'$, aryl, heteroaryl, cycloalkyl and heterocycle;
each R' is independently selected from the group consisting of hydrogen and alkyl;
X is a bond, —C(O)—, $CH_2$ and $SO_2$; and
$R^2$ and $R^3$ are independently selected from the group consisting of hydrogen, alkyl, aryl, heteroaryl, cycloalkyl, heterocycle, haloalkyl, arylalkyl, heteroarylalkyl, cycloalkylalkyl, heterocycloalkyl, alkoxyalkyl and aminoalkyl, or $R^2$ and $R^3$ are taken together with the atom to which they are attached to form a heterocyclic ring.

In another aspect, the disclosure provides a method of inhibiting replication of respiratory syncytial virus in a sample, comprising contacting the sample with an effective amount of a compound of formula (I):

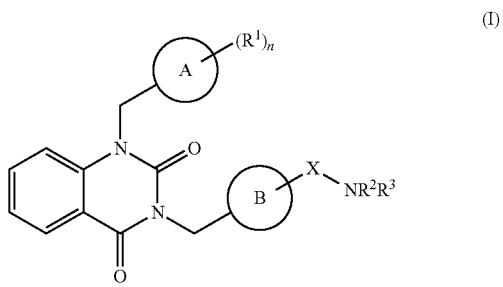

wherein:
A and B are each independently aryl, heteroaryl, cycloalkyl or heterocycle;
n is 0, 1, 2, 3, 4 or 5;
$R^1$ is selected from the group consisting of alkyl, halo, nitro, cyano, haloalkyl, amino, alkoxy, —$SO_2H$, —$SO_2NHR'$, $CONHR'$, aryl, heteroaryl, cycloalkyl and heterocycle;
each R' is independently selected from the group consisting of hydrogen and alkyl;
X is a bond, —C(O)—, $CH_2$ and $SO_2$; and
$R^2$ and $R^3$ are independently selected from the group consisting of hydrogen, alkyl, aryl, heteroaryl, cycloalkyl, heterocycle, haloalkyl, arylalkyl, heteroarylalkyl, cycloalkylalkyl, heterocycloalkyl, alkoxyalkyl and aminoalkyl, or $R^2$ and $R^3$ are taken together with the atom to which they are attached to form a heterocyclic ring.

In another aspect, the disclosure provides a pharmaceutical composition comprising a compound of formula (II):

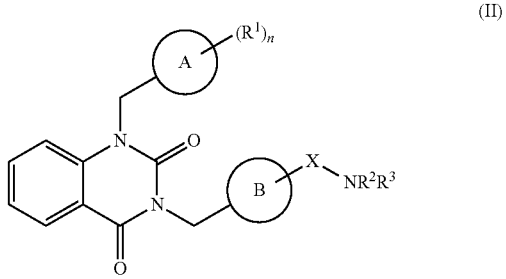

(II)

wherein:
A and B are each independently aryl, heteroaryl, cycloalkyl or heterocycle;
n is 0, 1, 2, 3, 4 or 5;
$R^1$ is selected from the group consisting of alkyl, halo, nitro, cyano, haloalkyl, amino, alkoxy, —$SO_2H$, —$SO_2NHR'$, $CONHR'$, aryl, heteroaryl, cycloalkyl and heterocycle;
each R' is independently selected from the group consisting of hydrogen and alkyl;
X is a bond, —C(O)—, $CH_2$ and $SO_2$; and
$R^2$ and $R^3$ are independently selected from the group consisting of hydrogen, alkyl, haloalkyl, heterocycloalkyl, alkoxyalkyl and aminoalkyl, or $R^2$ and $R^3$ are taken together with the atom to which they are attached to form a heterocyclic ring;
and a pharmaceutically acceptable carrier.

In another aspect, the disclosure provides a compound of formula (III):

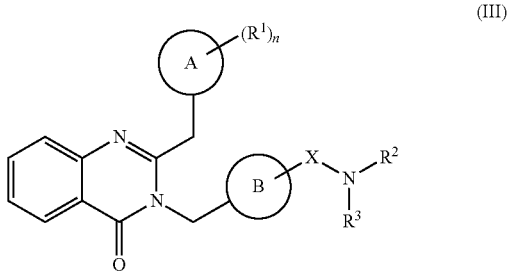

(III)

wherein:
A and B are each independently aryl, heteroaryl, cycloalkyl or heterocycle;
n is 0, 1, 2, 3, 4 or 5;
$R^1$ is selected from the group consisting of $C_2$-$C_6$ alkyl, halo, cyano, haloalkyl, amino, alkoxy, —$SO_2H$, —$SO_2NHR'$, $CONHR'$, aryl, heteroaryl, cycloalkyl and heterocycle;
each R' is independently selected from the group consisting of hydrogen and alkyl;
X is a bond, —C(O)—, $CH_2$ and $SO_2$; and
$R^2$ and $R^3$ are independently selected from the group consisting of hydrogen, alkyl, haloalkyl, heterocycloalkyl, alkoxyalkyl and aminoalkyl, or $R^2$ and $R^3$ are taken together with the atom to which they are attached to form a heterocyclic ring.

In another aspect, the disclosure provides a compound selected from the group consisting of:
4-((1-(4-isopropylbenzyl)-2,4-dioxo-1,2-dihydroquinazolin-3(4H)-yl)methyl)-N-(3-methoxypropyl)benzamide;
4-((1-(4-bromobenzyl)-2,4-dioxo-1,2-dihydroquinazolin-3(4H)-yl)methyl)-N-(3-methoxypropyl)benzamide;
4-((1-(4-ethylbenzyl)-2,4-dioxo-1,2-dihydroquinazolin-3(4H)-yl)methyl)-N-(3-methoxypropyl)benzamide;
4-((1-(4-methylbenzyl)-2,4-dioxo-1,2-dihydroquinazolin-3(4H)-yl)methyl)-N-(oxetan-3-ylmethyl)benzamide; and
4-((1-(4-(dimethylamino)benzyl)-2,4-dioxo-1,2-dihydroquinazolin-3(4H)-yl)methyl)-N-(oxetan-3-ylmethyl)benzamide.

Other aspects and embodiments will become apparent in light of the following disclosure and drawings.

BRIEF DESCRIPTION OF THE DRAWINGS

FIG. 3 is a table of data for various compounds.
FIG. 4 is a table of data for various compounds.
FIG. 5 is a table of data for various compounds.

DETAILED DESCRIPTION

Figure 1:
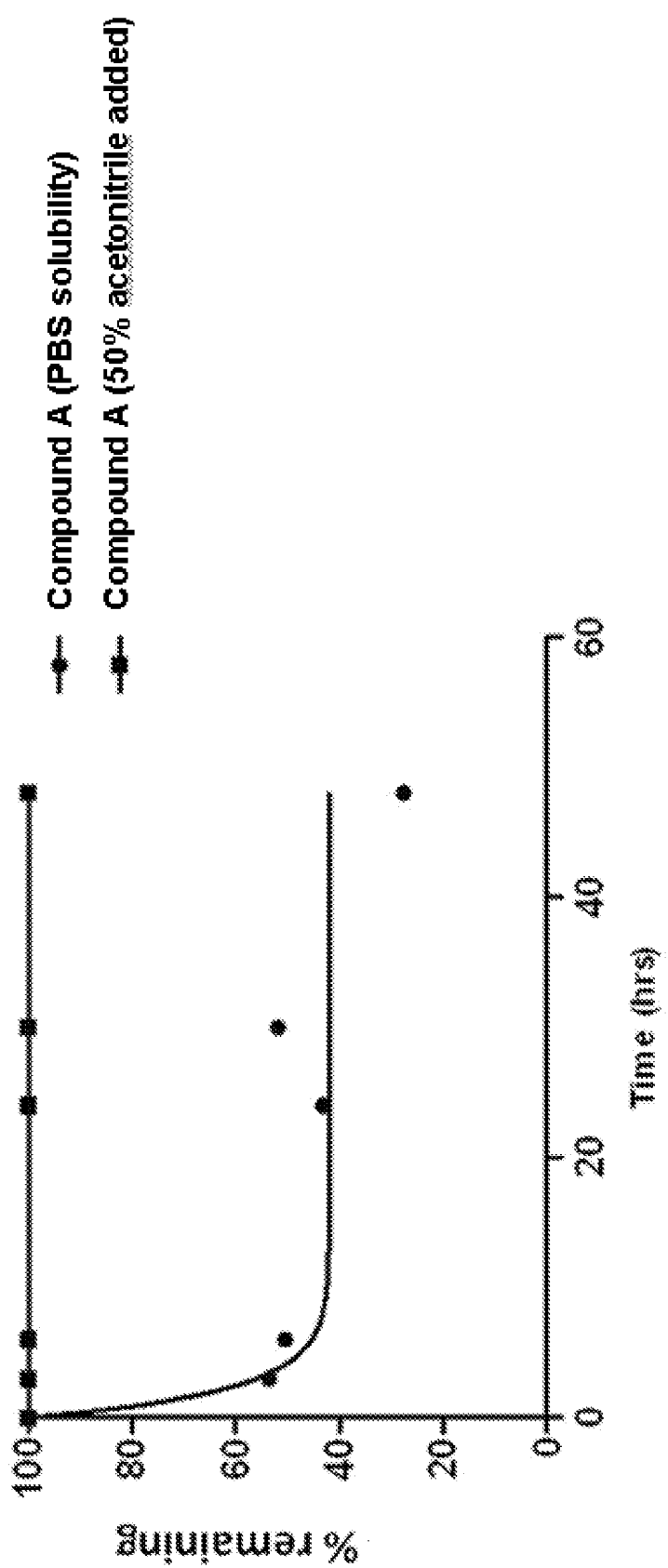
FIG. 1 is a graph of the stability of Compound A in over 48 hours under two different conditions.

Described herein are compounds, pharmaceutical compositions and methods for inhibiting replication of respiratory syncytial virus (RSV), and for treating an RSV infection in a subject.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

Section headings as used in this section and the entire disclosure herein are not intended to be limiting.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" is used synonymously with the term "approximately." Illustratively, the use of the term "about" indicates that values slightly outside the cited values, namely, plus or minus 10%. Such values are thus encompassed by the scope of the claims reciting the terms "about" and "approximately."

The terms "administer", "administering", "administered" or "administration" refer to any manner of providing a compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Contacting" as used herein, e.g., as in "contacting a sample" refers to contacting a sample directly or indirectly in vitro, ex vivo, or in vivo (i.e. within a subject as defined herein). Contacting a sample may include addition of a compound to a sample (e.g., a sample containing cells infected with RSV), or administration to a subject. Contacting encompasses administration to a solution, cell, tissue, mammal, subject, patient, or human. Further, contacting a cell includes adding an agent to a cell culture.

"Effective amount," as used herein, refers to a dosage of a compound or a composition effective for eliciting a desired effect. This term as used herein may also refer to an amount effective at bringing about a desired in vivo effect in an animal, mammal, or human, such as treating an RSV infection.

As used herein, the term "inhibit" refers to a reduction or decrease in a quality or quantity, compared to a baseline. For example, in the context of the present disclosure, inhibition of viral replication refers to a decrease in viral replication as compared to baseline. In some embodiments there is a reduction of about 30%, about 40%, about 50%, about 60%, about 70%, about 75%, about 80%, about 85%, about 90%, about 95%, about 99%, or about 100%. Those of ordinary skill in the art can readily determine whether or not viral replication has been inhibited and to what extent.

As used herein, the term "subject" is intended to include human and non-human animals. Exemplary human subjects include a human patient having a disorder, e.g., an RSV infection, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "treat" or "treating" a subject having a disorder refers to administering a compound or a composition described herein to the subject, such that at least one symptom of the disorder is cured, healed, alleviated, relieved, altered, remedied, ameliorated, or improved. Treating includes administering an amount effective to alleviate, relieve, alter, remedy, ameliorate, cure, improve or affect the disorder or the symptoms of the disorder. The treatment may inhibit deterioration or worsening of a symptom of a disorder.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "acyl" refers to an alkylcarbonyl, cycloalkylcarbonyl, heterocyclecarbonyl, arylcarbonyl or heteroarylcarbonyl substituent, any of which may be further substituted (e.g., with one or more substituents).

The term "alkyl" refers to a straight or branched saturated hydrocarbon chain. Alkyl groups may include a specified number of carbon atoms. For example, $C_1$-$C_{12}$ alkyl indicates that the alkyl group may have 1, 2, 3, 4, 5, 6, 7, 8, 9, 10, 11 or 12 carbon atoms. An alkyl group may be, e.g., a $C_1$-$C_{12}$ alkyl group, a $C_1$-$C_{10}$ alkyl group, a $C_1$-$C_8$ alkyl group, a $C_1$-$C_6$ alkyl group or a $C_1$-$C_4$ alkyl group. For example, exemplary $C_1$-$C_4$ alkyl groups include methyl, ethyl, n-propyl, isopropyl, n-butyl, sec-butyl, isobutyl and tert-butyl groups. An alkyl group may be optionally substituted with one or more substituents.

The term "alkenyl" refers to a straight or branched hydrocarbon chain having one or more double bonds. Alkenyl groups may include a specified number of carbon atoms. For example, $C_2$-$C_{12}$ alkenyl indicates that the alkenyl group may have 2, 3, 4, 5, 6, 7, 8, 9, 10, 11 or 12 carbon atoms. An alkenyl group may be, e.g., a $C_2$-$C_{12}$ alkenyl group, a $C_2$-$C_{10}$ alkenyl group, a $C_2$-$C_8$ alkenyl group, a $C_2$-$C_6$ alkenyl group or a $C_2$-$C_4$ alkenyl group. Examples of alkenyl groups include but are not limited to allyl, propenyl, 2-butenyl, 3-hexenyl and 3-octenyl groups. One of the double bond carbons may optionally be the point of attachment of the alkenyl substituent. An alkenyl group may be optionally substituted with one or more substituents.

The term "alkynyl" refers to a straight or branched hydrocarbon chain having one or more triple bonds. Alkynyl groups may include a specified number of carbon atoms. For example, $C_2$-$C_{12}$ alkynyl indicates that the alkynyl group may have 2, 3, 4, 5, 6, 7, 8, 9, 10, 11 or 12 carbon atoms. An alkynyl group may be, e.g., a $C_2$-$C_{12}$ alkynyl group, a $C_2$-$C_{10}$ alkynyl group, a $C_2$-$C_8$ alkynyl group, a $C_2$-$C_6$ alkynyl group or a $C_2$-$C_4$ alkynyl group. Examples of alkynyl groups include but are not limited to ethynyl, propargyl, and 3-hexynyl. One of the triple bond carbons may optionally be the point of attachment of the alkynyl substituent. An alkynyl group may be optionally substituted with one or more substituents.

The term "amino" refers to a group of the formula —NR$^a$R$^b$, wherein R$^a$ and R$^b$ are each independently selected from, for example, hydrogen, alkyl, alkenyl, alkynyl, cycloalkyl, heterocycle, aryl and heteroaryl, or R$^a$ and R$^b$, together with the nitrogen to which they are attached, may form a ring structure. Examples of amino groups include but are not limited to —NH$_2$, alkylamino groups such as —NHCH$_3$, —NHCH$_2$CH$_3$ and —NHCH(CH$_3$)$_2$, dialkylamino groups such as —N(CH$_3$)$_2$ and —N(CH$_2$CH$_3$)$_2$, and arylamino groups such as —NHPh. Examples of cyclic amino groups include but are not limited to aziridinyl, azetidinyl, pyrrolidinyl, piperidino, piperazinyl, perhydrodiazepinyl, morpholino, and thiomorpholino. The groups R$^a$ and R$^b$ may be optionally substituted with one or more substituents.

The term "aryl" refers to an aromatic monocyclic, bicyclic, or tricyclic hydrocarbon ring system, wherein any ring atom capable of substitution can be substituted (e.g., with one or more substituents). Examples of aryl moieties include but are not limited to phenyl, naphthyl, and anthracenyl. Aryl groups may be optionally substituted with one or more substituents.

The term "arylalkyl" refers to an alkyl moiety in which at least one alkyl hydrogen atom is replaced with an aryl group. Arylalkyl includes groups in which more than one hydrogen atom has been replaced with an aryl group. Examples of arylalkyl groups include but are not limited to benzyl, 2-phenylethyl, 3-phenylpropyl, 9-fluorenyl, benzhydryl, and trityl groups. Arylalkyl groups may be optionally substituted with one or more substituents, on either the aryl moiety or the alkyl moiety.

The term "cycloalkyl" as used herein refers to non-aromatic, saturated or partially unsaturated cyclic, bicyclic, tricyclic or polycyclic hydrocarbon groups having 3 to 12 carbons. Any ring atom can be substituted (e.g., with one or more substituents). Cycloalkyl groups can contain fused rings. Fused rings are rings that share one or more common carbon atoms. Examples of cycloalkyl groups include but are not limited to cyclopropyl, cyclobutyl, cyclopentyl, cyclohexyl, cyclohexenyl, cyclohexadienyl, methylcyclohexyl, adamantyl, norbornyl, norbornenyl, tetrahydronaphthalenyl and dihydroindenyl. Cycloalkyl groups may be optionally substituted with one or more substituents.

The term "cycloalkylalkyl", as used herein, refers to an alkyl group in which at least one hydrogen atom is replaced with a cycloalkyl group. Cycloalkylalkyl groups include those in which more than one hydrogen atom of the alkyl group is replaced with a cycloalkyl group. Examples of cycloalkylalkyl groups include but are not limited to cyclohexylmethyl, cyclopentylmethyl, cyclobutylmethyl and cyclopropylmethyl. Cycloalkylalkyl groups can be optionally substituted with one or more substituents, on either the cycloalkyl moiety or the alkyl moiety.

The term "halo" or "halogen" as used herein refers to any radical of fluorine, chlorine, bromine or iodine.

The term "haloalkyl" as used herein refers to an alkyl group as defined herein, in which one or more hydrogen atoms are replaced with halogen atoms, and includes alkyl moieties in which all hydrogens have been replaced with halogens (e.g., perfluoroalkyl such as $CF_3$).

"Heteroalkyl" refers to an alkyl group as defined herein, wherein at least one carbon atom of the alkyl group is replaced by a heteroatom. Heteroalkyl groups may contain from 1 to 18 non-hydrogen atoms (carbon and heteroatoms) in the chain, or 1 to 12 atoms, or 1 to 6 atoms, or 1 to 4 atoms. Heteroalkyl groups may be straight or branched, and saturated or unsaturated. Unsaturated heteroalkyl groups have one or more double bonds and/or one or more triple bonds. Heteroalkyl groups may be unsubstituted or substituted. Exemplary heteroalkyl groups include but are not limited to alkoxyalkyl (e.g., methoxymethyl), and aminoalkyl (e.g., alkylaminoalkyl and dialkylaminoalkyl). Heteroalkyl groups may be optionally substituted with one or more substituents.

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include but are not limited to radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines. Heteroaryl groups may be optionally substituted with one or more substituents.

The term "heteroarylalkyl" refers to an alkyl moiety in which at least one alkyl hydrogen atom is replaced with a heteroaryl group. Heteroarylalkyl includes groups in which more than one hydrogen atom has been replaced with a heteroaryl group. Examples of heteroarylalkyl groups include but are not limited to imidazolylmethyl (e.g., 1H-imidazol-2-ylmethyl and 1H-imidazol-4-ylmethyl), pyridinylmethyl (e.g., pyridin-3-ylmethyl and pyridin-4-ylmethyl), pyrimidinylmethyl (e.g., pyrimidin-5-ylmethyl), furylmethyl (e.g., fur-2-ylmethyl and fur-3-ylmethyl), and thienylmethyl (e.g., thien-2-ylmethyl and thien-3-ylmethyl) groups. Heteroarylalkyl groups may be optionally substituted with one or more substituents, on either the heteroaryl moiety or the alkyl moiety.

The term "heteroatom", as used herein, refers to a non-carbon or hydrogen atom such as a nitrogen, sulfur, oxygen, silicon or phosphorus atom. Groups containing more than one heteroatom may contain different heteroatoms.

The term "heterocycle", as used herein, refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocycle groups can contain fused rings, which are rings that share one or more common atoms. Examples of heterocycle groups include but are not limited to radicals of tetrahydrofuran, tetrahydrothiophene, tetrahydropyran, oxetane, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like. Heterocycle groups may be optionally substituted with one or more substituents.

The term "heterocycloalkyl" refers to an alkyl moiety in which at least one alkyl hydrogen atom is replaced with a heterocycle group. Heterocyclealkyl includes groups in which more than one hydrogen atom has been replaced with a heterocycle group. Examples of heterocycloalkyl groups include but are not limited to oxetanylmethyl, morpholinomethyl, and pyrrolidinylmethyl groups, and the like. Heterocyclealkyl groups may be optionally substituted with one or more substituents, on either the heterocycle moiety or the alkyl moiety.

The term "hydroxy" refers to an —OH radical. The term "alkoxy" refers to an —O-alkyl radical. The term "aryloxy" refers to an —O-aryl radical.

The term "oxo" refers to an oxygen atom, which forms a carbonyl when attached to carbon, an N-oxide when attached to nitrogen, and a sulfoxide or sulfone when attached to sulfur (i.e. =O).

The term "mercapto" or "thiol" refers to an —SH radical. The term "thioalkoxy" or "thioether" refers to an —S-alkyl radical. The term "thioaryloxy" refers to an —S-aryl radical.

The term "substituents" refers to a group "substituted" on an alkyl, alkenyl, alkynyl, cycloalkyl, heterocycle, aryl, arylalkyl, heteroaryl or heteroarylalkyl group at any atom of that group. Any atom can be substituted. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein. For example, the abbreviations Me, Et and Ph represent methyl, ethyl and phenyl, respectively. A more comprehensive list of standard abbreviations used by organic chemists appears in a table entitled Standard List of Abbreviations of the Journal of Organic Chemistry. The abbreviations contained in said list are hereby incorporated by reference.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

In accordance with a convention used in the art, the group:

is used in structural formulae herein to depict the bond that is the point of attachment of the moiety or substituent to the core or backbone structure.

2. Compounds

Compounds that may be used in the methods and pharmaceutical compositions described herein include those having the following formula (I):

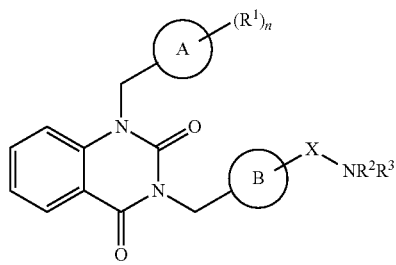

wherein:
A and B are each independently aryl, heteroaryl, cycloalkyl or heterocycle;
n is 0, 1, 2, 3, 4 or 5;
$R^1$ is selected from the group consisting of alkyl, halo, nitro, cyano, haloalkyl, amino, alkoxy, —SO$_2$H, —SO$_2$NHR', CONHR', aryl, heteroaryl, cycloalkyl and heterocycle;
each R' is independently selected from the group consisting of hydrogen and alkyl;
X is a bond, —C(O)—, CH$_2$ and SO$_2$; and
$R^2$ and $R^3$ are independently selected from the group consisting of hydrogen, alkyl, aryl, heteroaryl, cycloalkyl, heterocycle, haloalkyl, arylalkyl, heteroarylalkyl, cycloalkylalkyl, heterocycloalkyl, alkoxyalkyl and aminoalkyl, or $R^2$ and $R^3$ are taken together with the atom to which they are attached to form a heterocyclic ring.

In some embodiments, A is aryl (e.g., phenyl). In some embodiments, n is 1. In some embodiments, $R^1$ is alkyl, such as C$_1$-C$_4$ alkyl (e.g., methyl, ethyl or isopropyl). In some embodiments, the group A and its substituent group —(R$^1$)$_n$ have the following formula:

In some embodiments, $R^1$ is halo, such as bromo. In some embodiments, $R^1$ is nitro. In some embodiments, $R^1$ is amino (e.g., dimethylamino).

In some embodiments, B is aryl (e.g., phenyl). In some embodiments, the group B and its substituent group —X—NR$^2$R$^3$ have the following formula:

In some embodiments, X is —C(O)—. In some embodiments, one of $R^2$ and $R^3$ is hydrogen and the other is alkoxyalkyl (e.g., 3-methoxypropyl) or heterocycloalkyl (e.g., oxetan-3-ylmethyl).

Suitable compounds of formula (I) include those found in Table 1.

TABLE 1

Representative Compounds

| Compound | Name | Structure |
|---|---|---|
| A | 4-((1-(4-isopropylbenzyl)-2,4-dioxo-1,2-dihydroquinazolin-3(4H)-yl)methyl)-N-(3-methoxypropyl)benzamide | 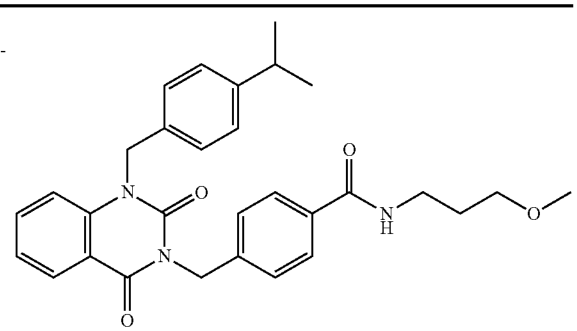 |

TABLE 1-continued

Representative Compounds

| Compound | Name | Structure |
|---|---|---|
| B | N-(3-methoxypropyl)-4-((1-(4-nitrobenzyl)-2,4-dioxo-1,2-dihydroquinazolin-3(4H)-yl)methyl)benzamide | 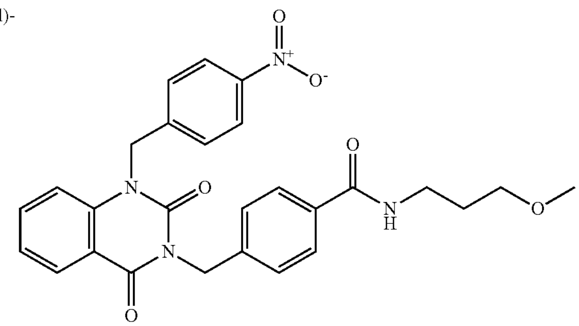 |
| C | 4-((1-(4-bromobenzyl)-2,4-dioxo-1,2-dihydroquinazolin-3(4H)-yl)methyl)-N-(3-methoxypropyl)benzamide | 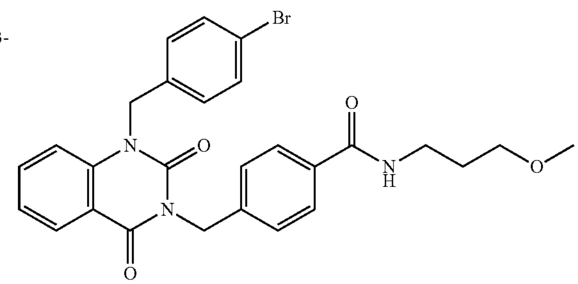 |
| D | 4-((1-(4-ethylbenzyl)-2,4-dioxo-1,2-dihydroquinazolin-3(4H)-yl)methyl)-N-(3-methoxypropyl)benzamide | 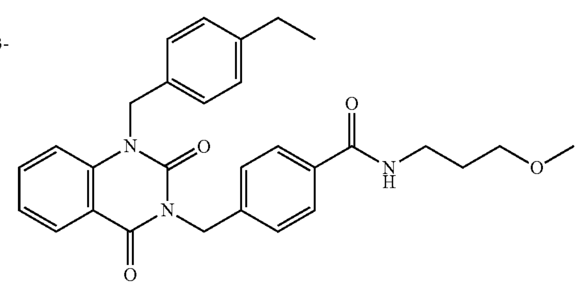 |
| E | 4-((1-(4-(dimethylamino)benzyl)-2,4-dioxo-1,2-dihydroquinazolin-3(4H)-yl)methyl)-N-(oxetan-3-ylmethyl)benzamide | 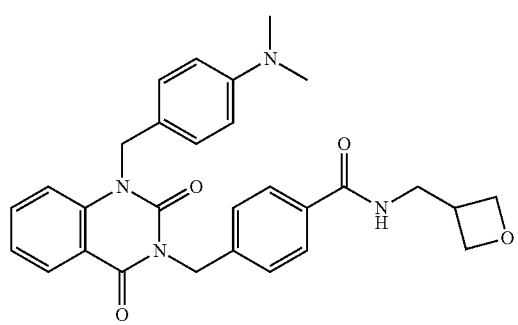 [SMILES: CN(C)c1ccc(Cn2c(=O)n(Cc3ccc(C(=O)NCC4COC4)cc3)c(=O)c3ccccc32)cc1] |
| F | 4-((1-(4-methylbenzyl)-2,4-dioxo-1,2-dihydroquinazolin-3(4H)-yl)methyl)-N-(oxetan-3-ylmethyl)benzamide | 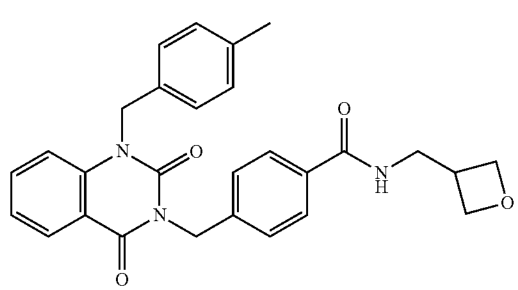 [SMILES: Cc1ccc(Cn2c(=O)n(Cc3ccc(C(=O)NCC4COC4)cc3)c(=O)c3ccccc32)cc1] |

The disclosure also provides compounds having the following formula (II):

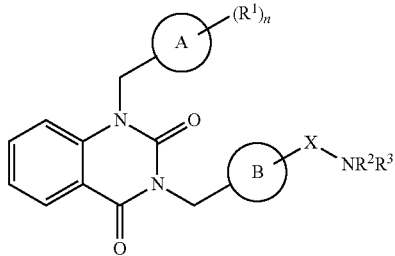
(II)

wherein:
A and B are each independently aryl, heteroaryl, cycloalkyl or heterocycle;
n is 0, 1, 2, 3, 4 or 5;
$R^1$ is selected from the group consisting of alkyl, halo, nitro, cyano, haloalkyl, amino, alkoxy, —$SO_2H$, —$SO_2NHR'$, CONHR', aryl, heteroaryl, cycloalkyl and heterocycle;
each R' is independently selected from the group consisting of hydrogen and alkyl;
X is a bond, —C(O)—, $CH_2$ and $SO_2$; and
$R^2$ and $R^3$ are independently selected from the group consisting of hydrogen, alkyl, haloalkyl, heterocycloalkyl, alkoxyalkyl and aminoalkyl, or $R^2$ and $R^3$ are taken together with the atom to which they are attached to form a heterocyclic ring.

In some embodiments, A is aryl (e.g., phenyl). In some embodiments, n is 1. In some embodiments, the group A and its substituent group —$(R^1)_n$ have the following formula:

In some embodiments, $R^1$ is $C_1$-$C_4$ alkyl (e.g., methyl, ethyl or isopropyl). In some embodiments, $R^1$ is halo, such as bromo. In some embodiments, $R^1$ is nitro. In some embodiments, $R^1$ is amino (e.g., dimethylamino).

In some embodiments, B is aryl (e.g., phenyl). In some embodiments, the group B and its substituent group —X—$NR^2R^3$ have the following formula:

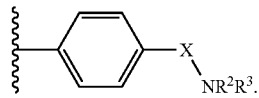

In some embodiments, X is —C(O)—. In some embodiments, one of $R^2$ and $R^3$ is hydrogen and the other is alkoxyalkyl (e.g., 3-methoxypropyl) or heterocycloalkyl (e.g., oxetan-3-ylmethyl).

Suitable compounds of formula (II) include:
4-((1-(4-isopropylbenzyl)-2,4-dioxo-1,2-dihydroquinazolin-3(4H)-yl)methyl)-N-(3-methoxypropyl)benzamide;
N-(3-methoxypropyl)-4((1-(4-nitrobenzyl)-2,4-dioxo-1,2-dihydroquinazolin-3(4H)-yl)methyl)benzamide;
4-((1-(4-bromobenzyl)-2,4-dioxo-1,2-dihydroquinazolin-3(4H)-yl)methyl)-N-(3-methoxypropyl)benzamide;
4-((1-(4-ethylbenzyl)-2,4-dioxo-1,2-dihydroquinazolin-3(4H)-yl)methyl)-N-(3-methoxypropyl)benzamide;
4-((1-(4-methylbenzyl)-2,4-dioxo-1,2-dihydroquinazolin-3(4H)-yl)methyl)-N-(oxetan-3-ylmethyl)benzamide; and
4-((1-(4-(dimethylamino)benzyl)-2,4-dioxo-1,2-dihydroquinazolin-3(4H)-yl)methyl)-N-(oxetan-3-ylmethyl)benzamide.

Other compounds encompassed by this disclosure include compounds of formula (III):

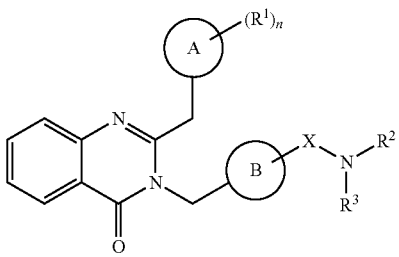
(III)

wherein:
A and B are each independently aryl, heteroaryl, cycloalkyl or heterocycle;
n is 0, 1, 2, 3, 4 or 5;
$R^1$ is selected from the group consisting of $C_2$-$C_6$ alkyl, halo, cyano, haloalkyl, amino, alkoxy, —$SO_2H$, —$SO_2NHR'$, CONHR', aryl, heteroaryl, cycloalkyl and heterocycle;
each R' is independently selected from the group consisting of hydrogen and alkyl;
X is a bond, —C(O)—, $CH_2$ and $SO_2$; and
$R^2$ and $R^3$ are independently selected from the group consisting of hydrogen, alkyl, haloalkyl, heterocycloalkyl, alkoxyalkyl and aminoalkyl, or $R^2$ and $R^3$ are taken together with the atom to which they are attached to form a heterocyclic ring.

In some embodiments, A is aryl (e.g., phenyl). In some embodiments, n is 1. In some embodiments, the group A and its substituent group —$(R^1)_n$ have the following formula:

In some embodiments, $R^1$ is $C_2$-$C_4$ alkyl (e.g., ethyl or isopropyl). In some embodiments, $R^1$ is halo, such as bromo. In some embodiments, $R^1$ is amino (e.g., dimethylamino).

In some embodiments, B is aryl (e.g., phenyl). In some embodiments, the group B and its substituent group —X—$NR^2R^3$ have the following formula:

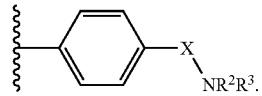

In some embodiments, X is —C(O)—. In some embodiments, one of $R^2$ and $R^3$ is hydrogen and the other is alkoxyalkyl (e.g., 3-methoxypropyl) or heterocycloalkyl (e.g., oxetan-3-ylmethyl).

Suitable compounds of formula (III) include:
4-((1-(4-isopropylbenzyl)-2,4-dioxo-1,2-dihydroquinazo-lin-3(4H)-yl)methyl)-N-(3-methoxypropyl)benzamide;
4-((1-(4-bromobenzyl)-2,4-dioxo-1,2-dihydroquinazolin-3(4H)-yl)methyl)-N-(3-methoxypropyl)benzamide;
4-((1-(4-ethylbenzyl)-2,4-dioxo-1,2-dihydroquinazolin-3(4H)-yl)methyl)-N-(3-methoxypropyl)benzamide; and
4-((1-(4-(dimethylamino)benzyl)-2,4-dioxo-1,2-dihydro-quinazolin-3(4H)-yl)methyl)-N-(oxetan-3-ylmethyl)benzamide.

Figure 7:
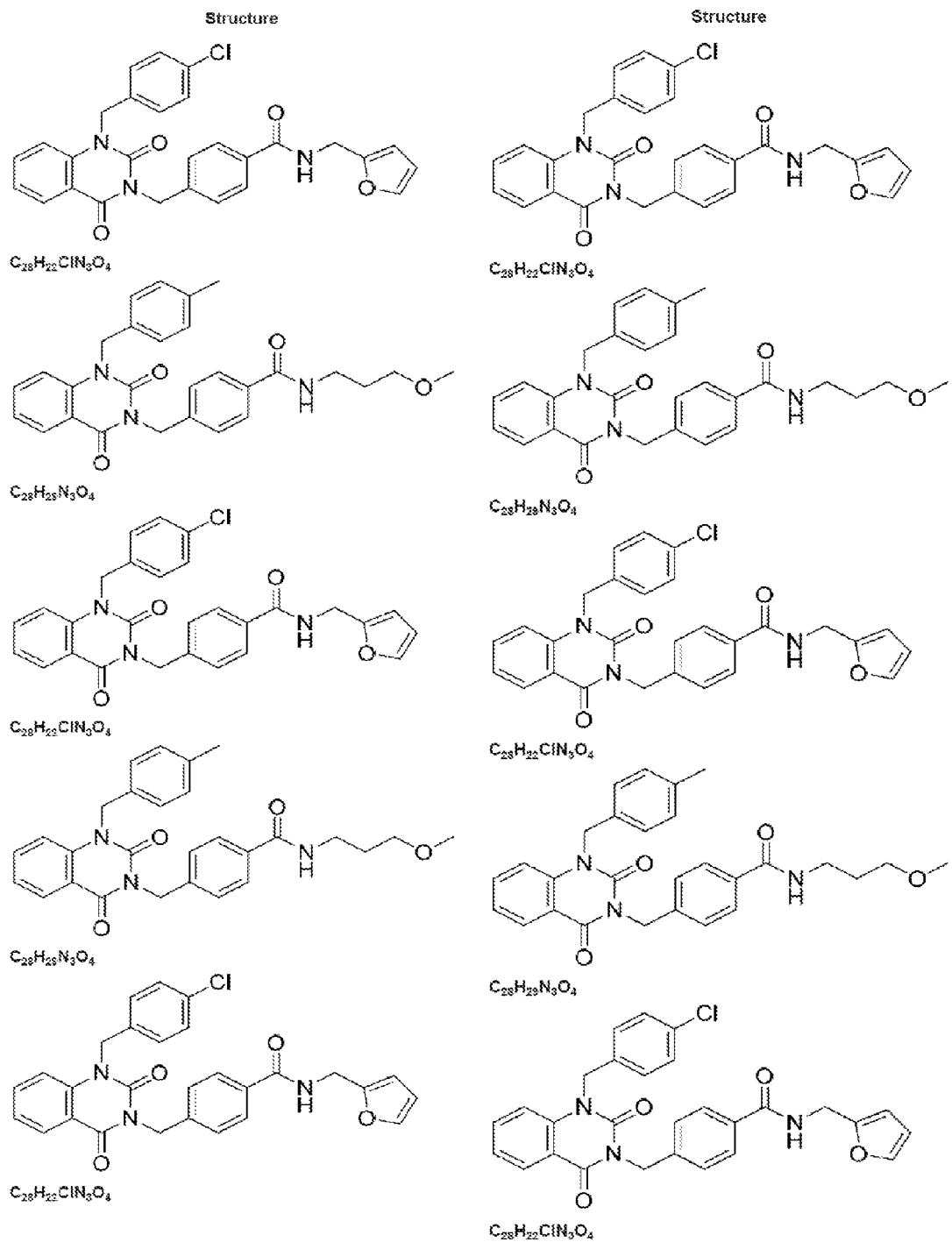
FIG. 7 illustrates exemplary compounds.
Figure 7:
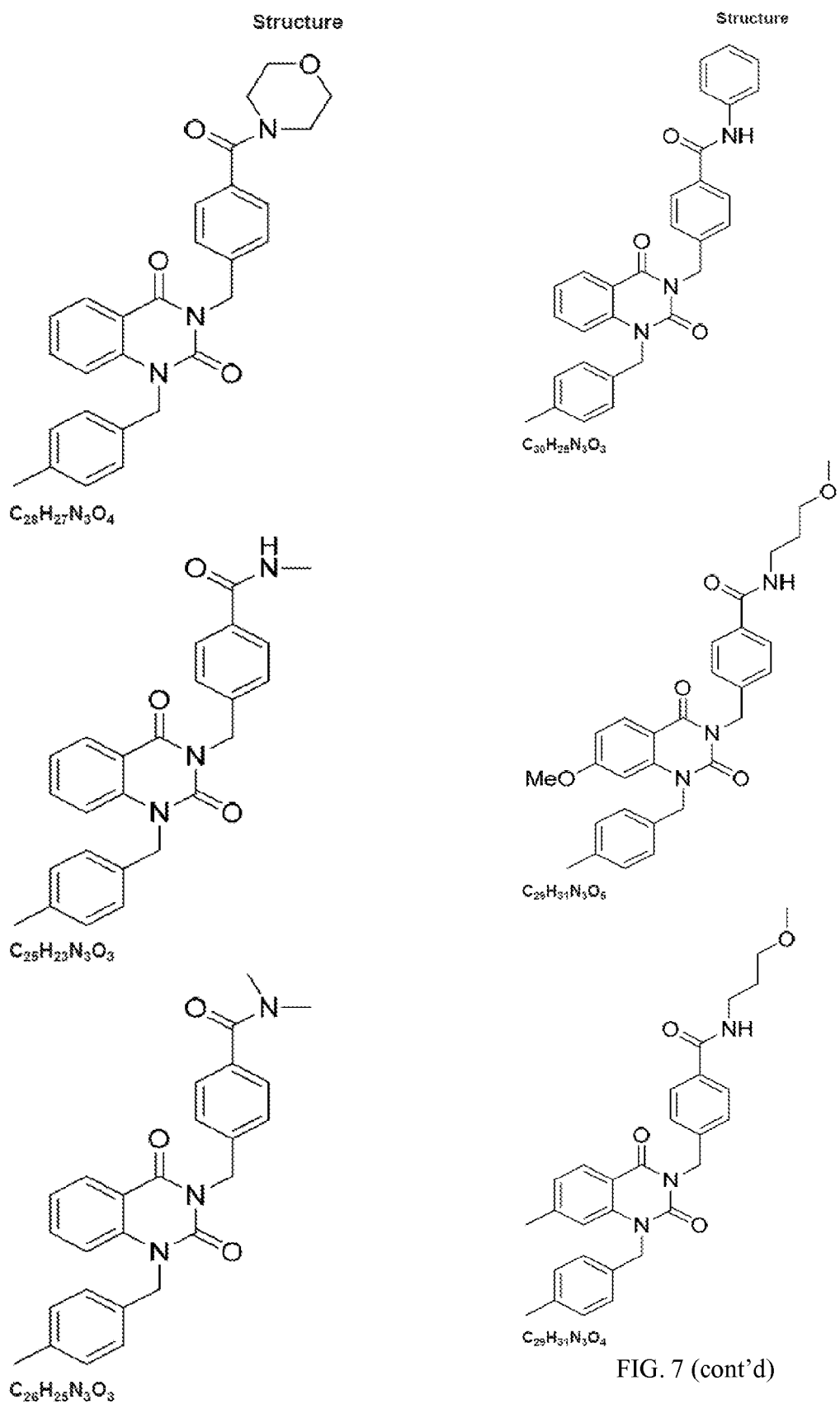
Figure 7:
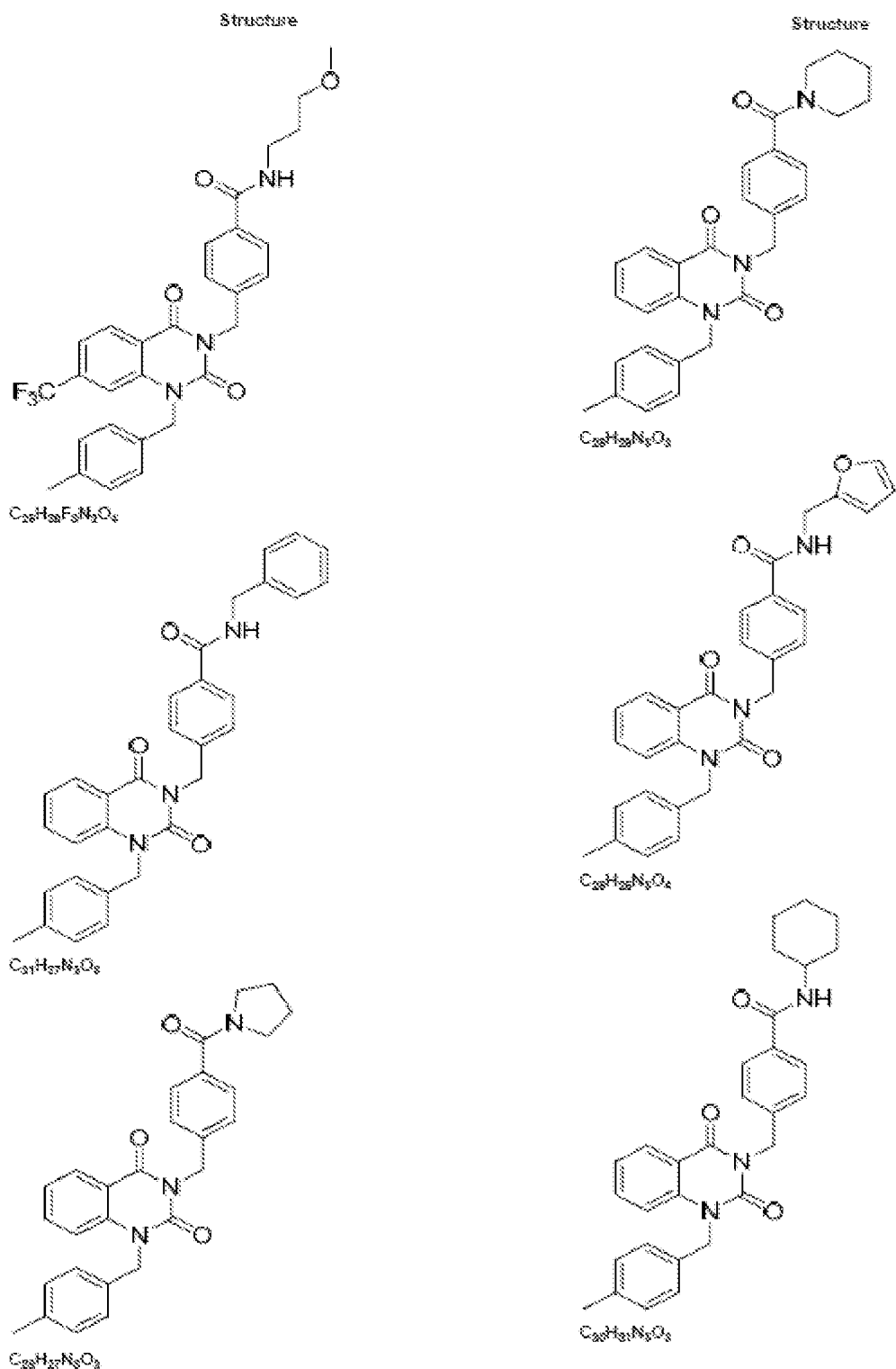
Figure 7:
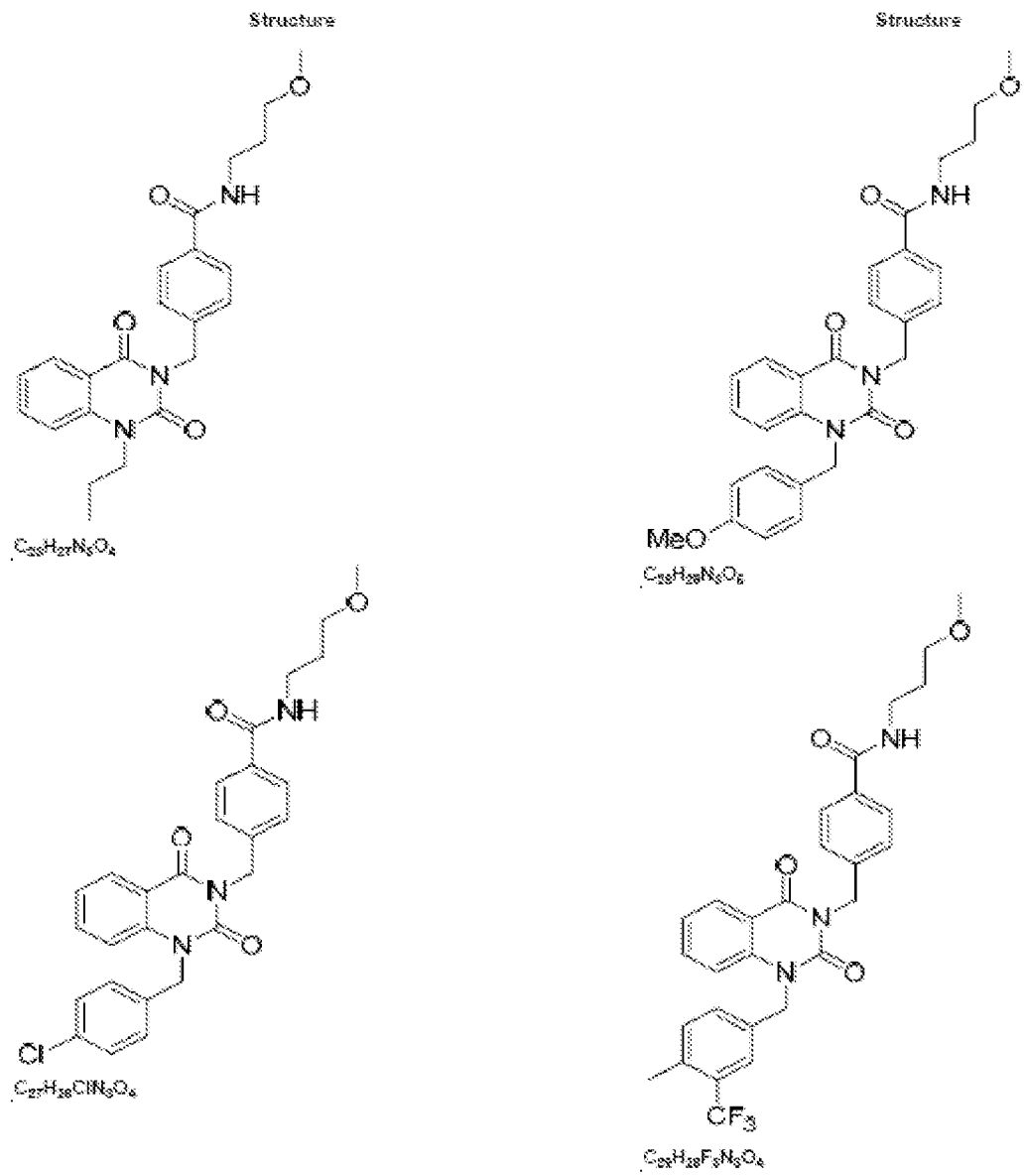
Figure 7:
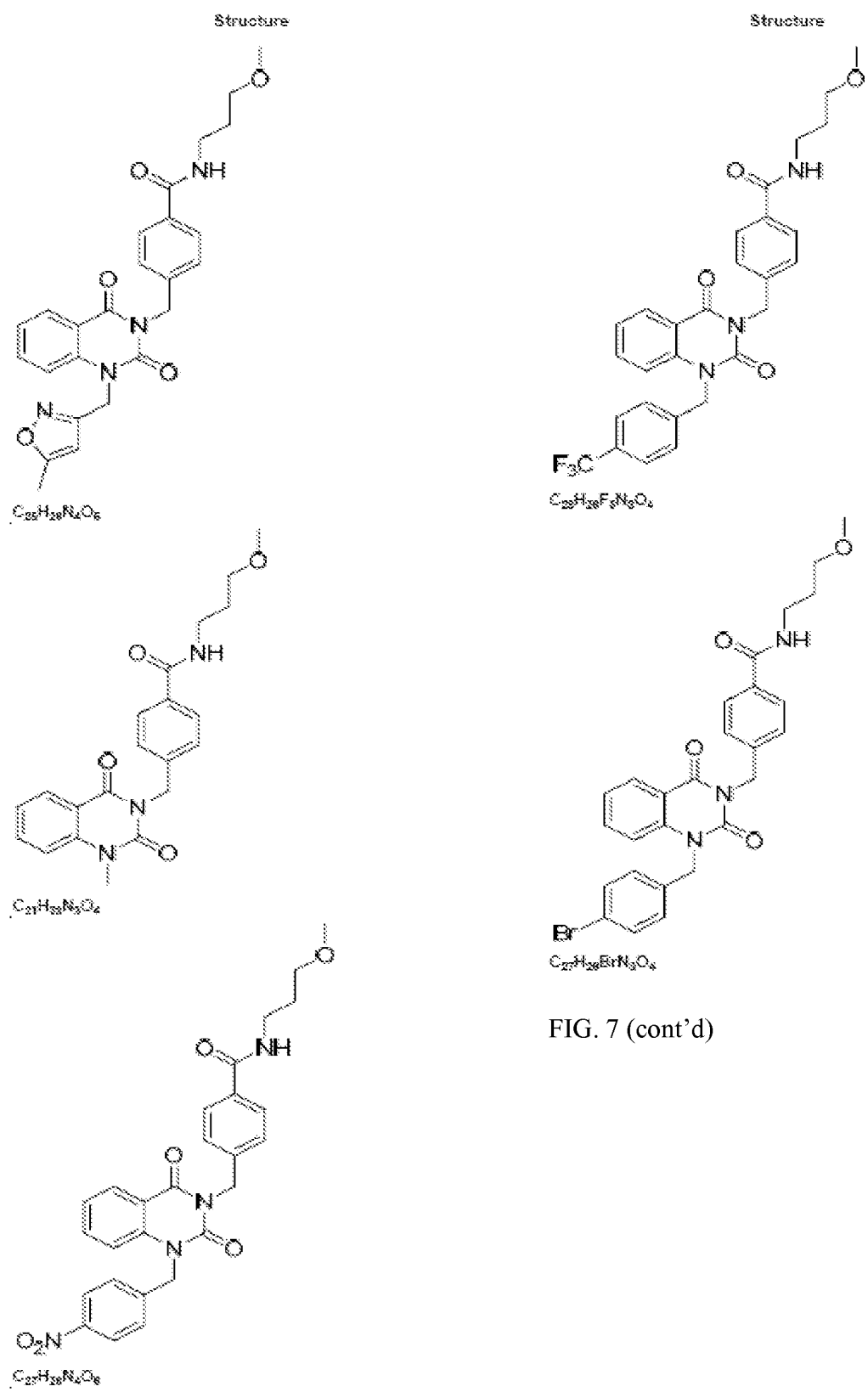
Figure 7:
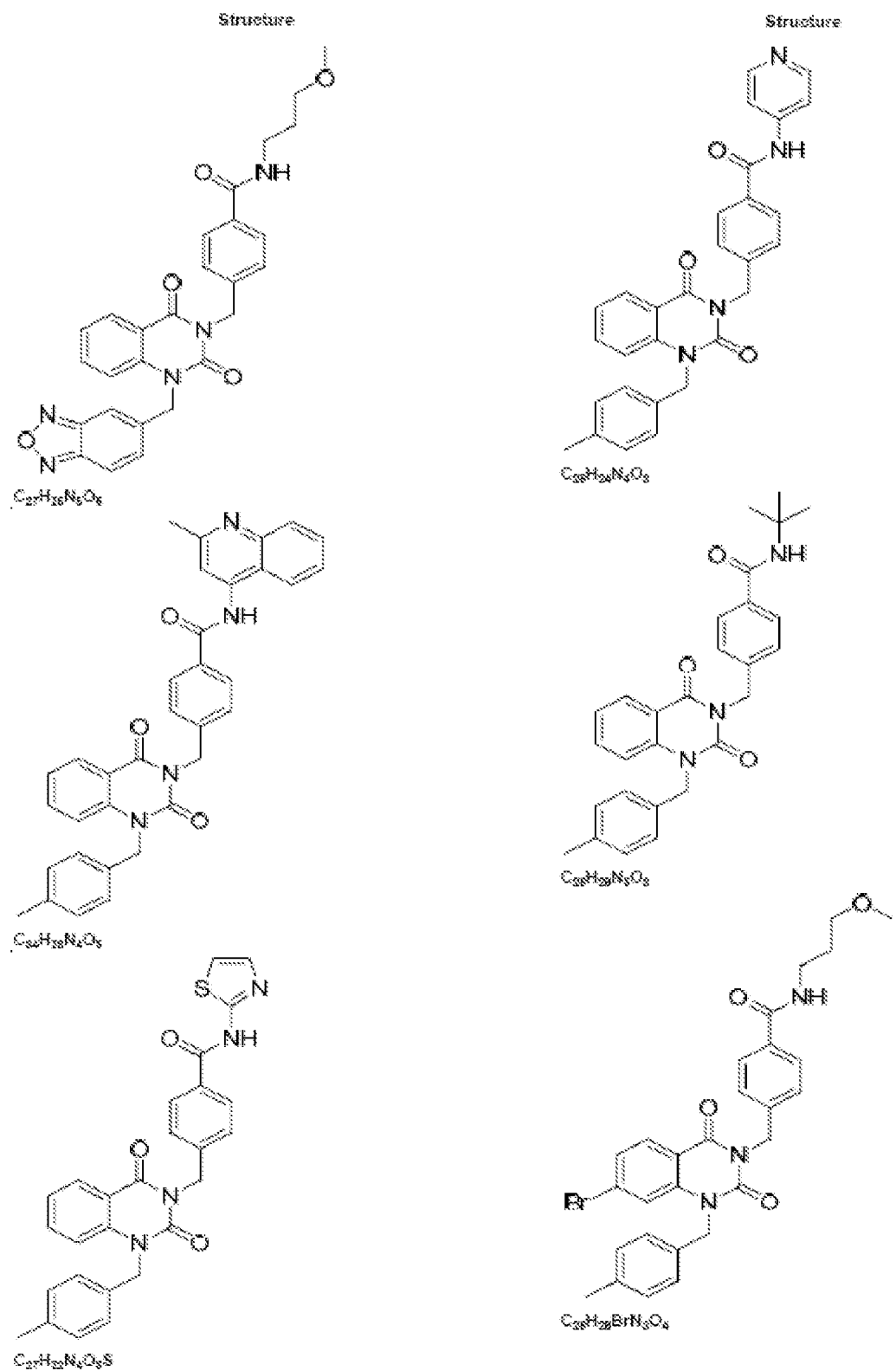
Figure 7:
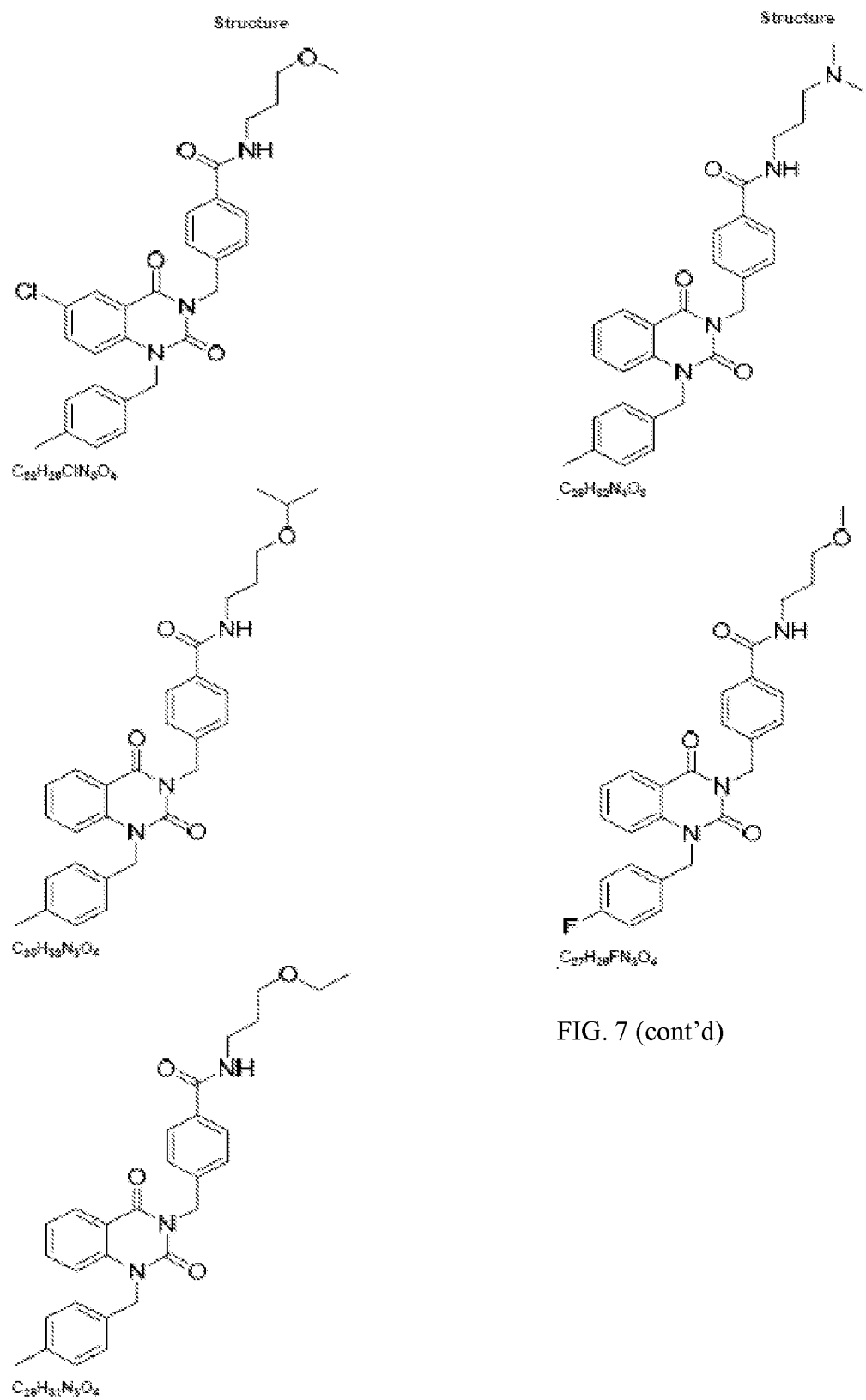
Figure 7:
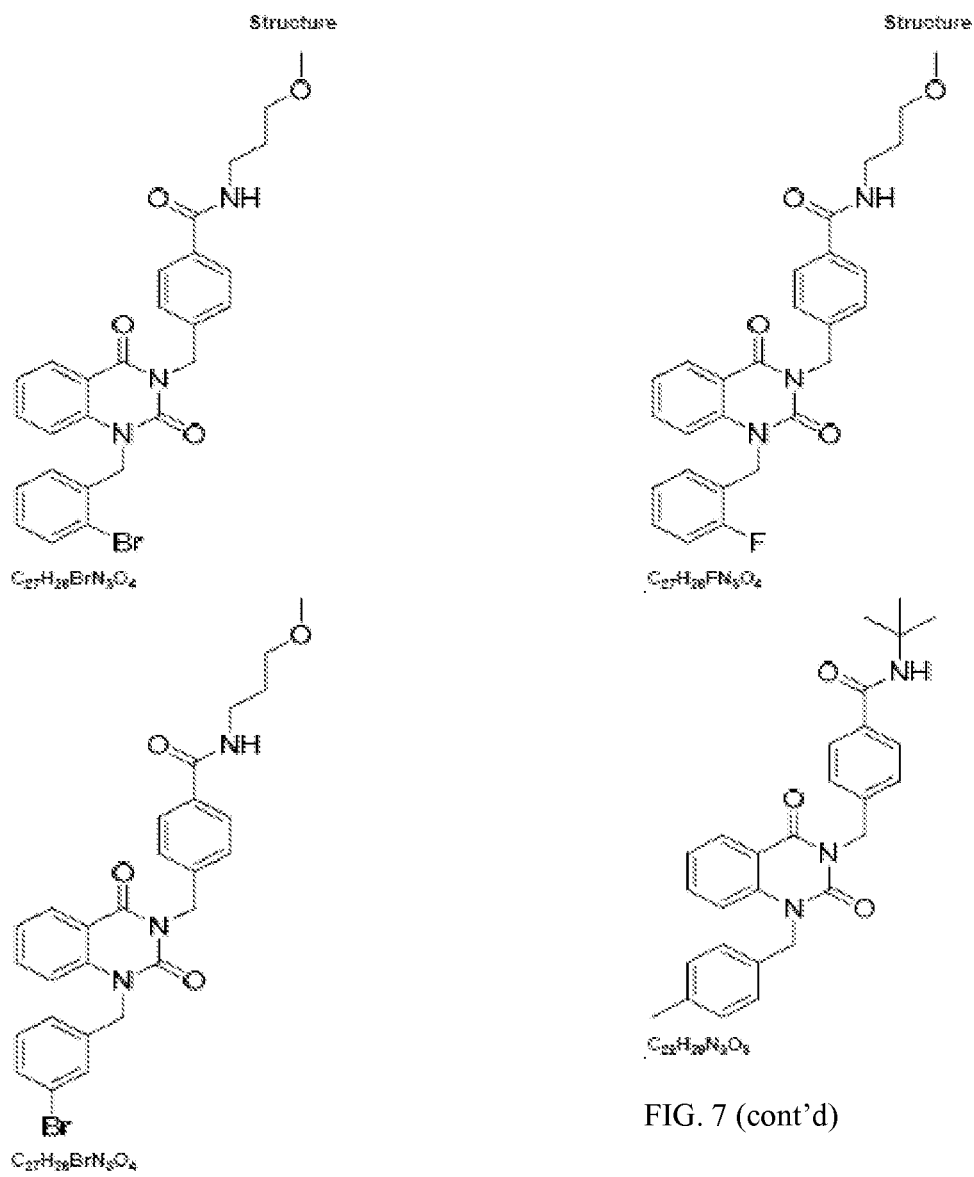
Figure 7:
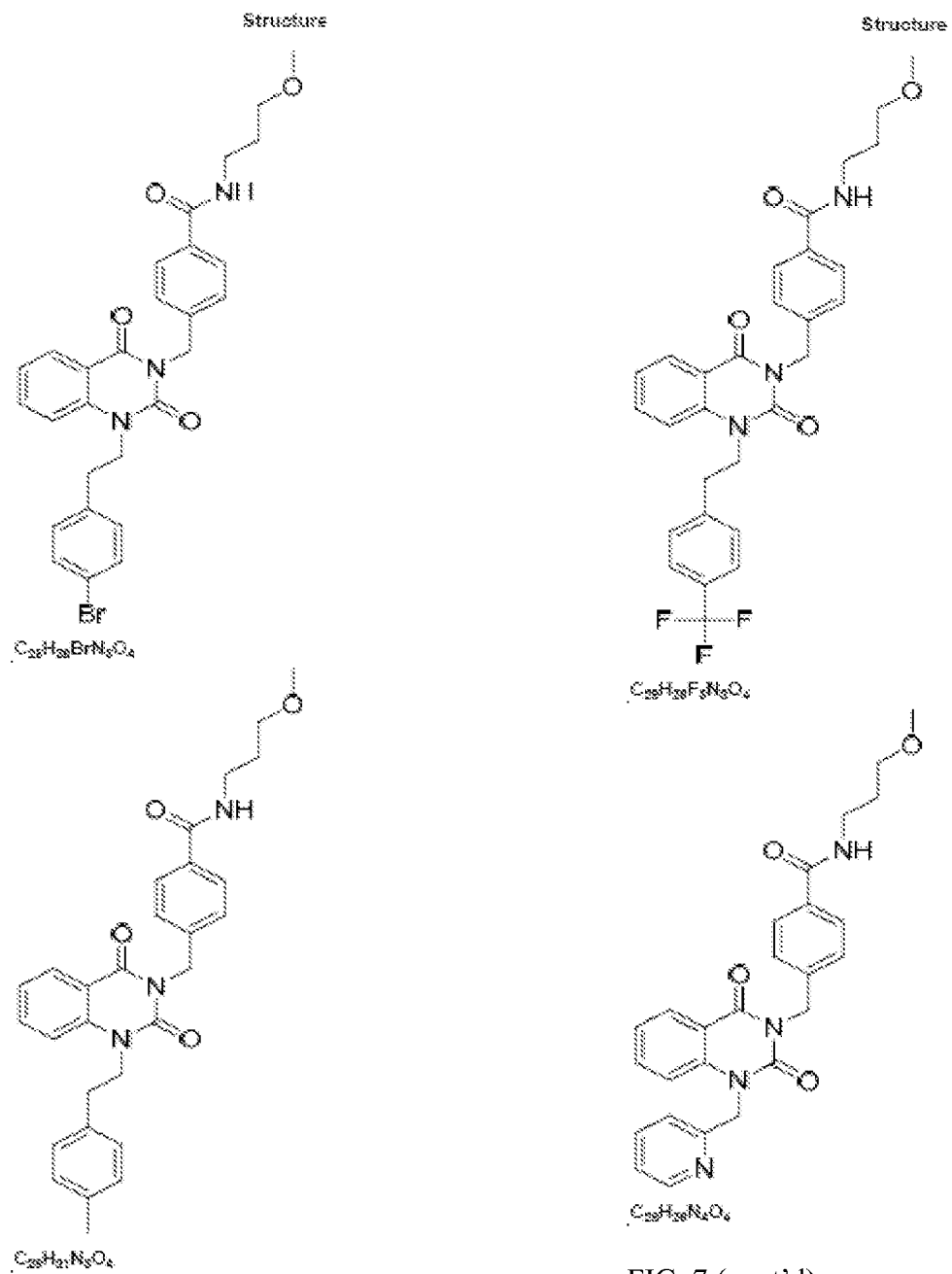
Figure 7:
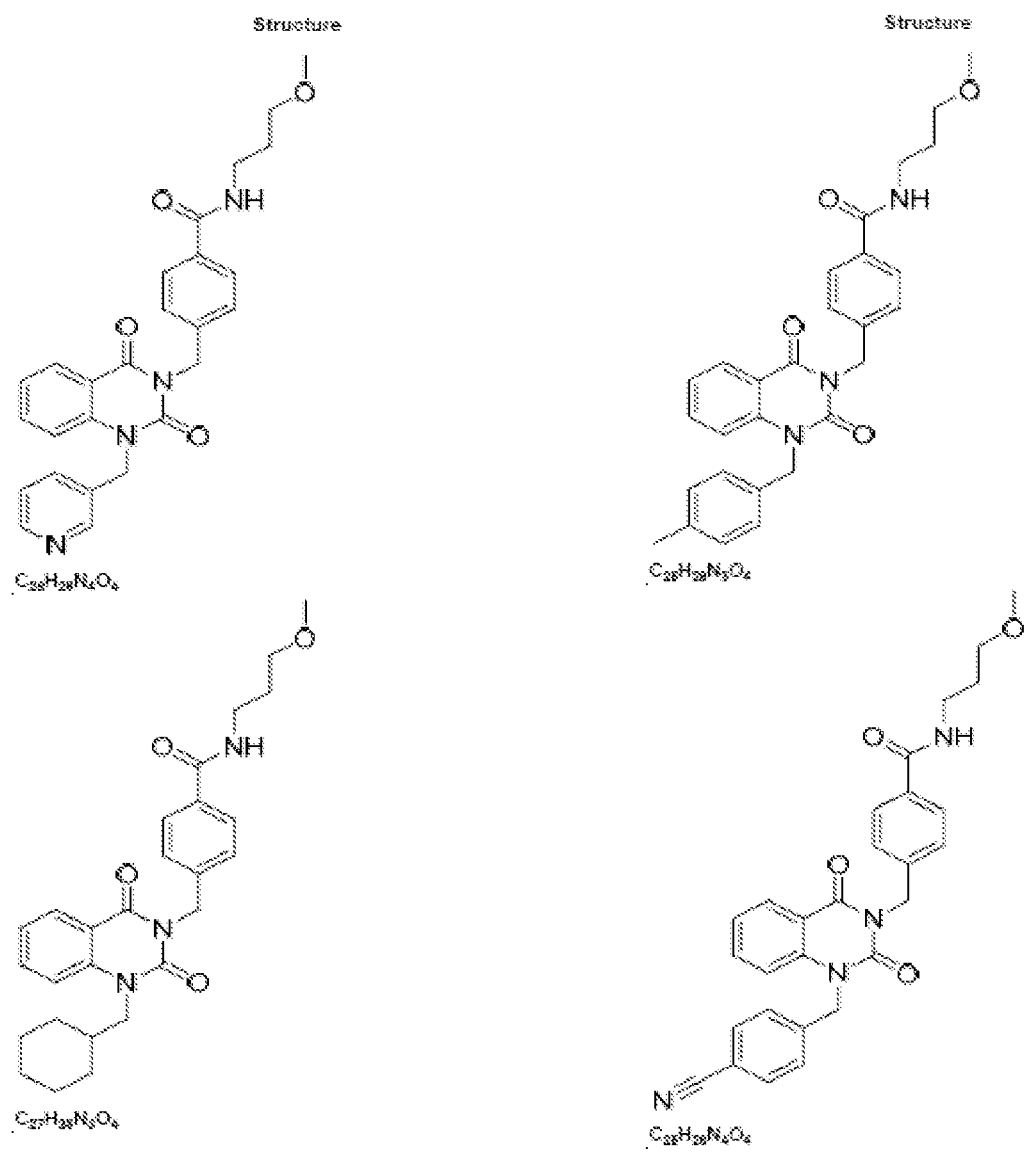
Figure 7:
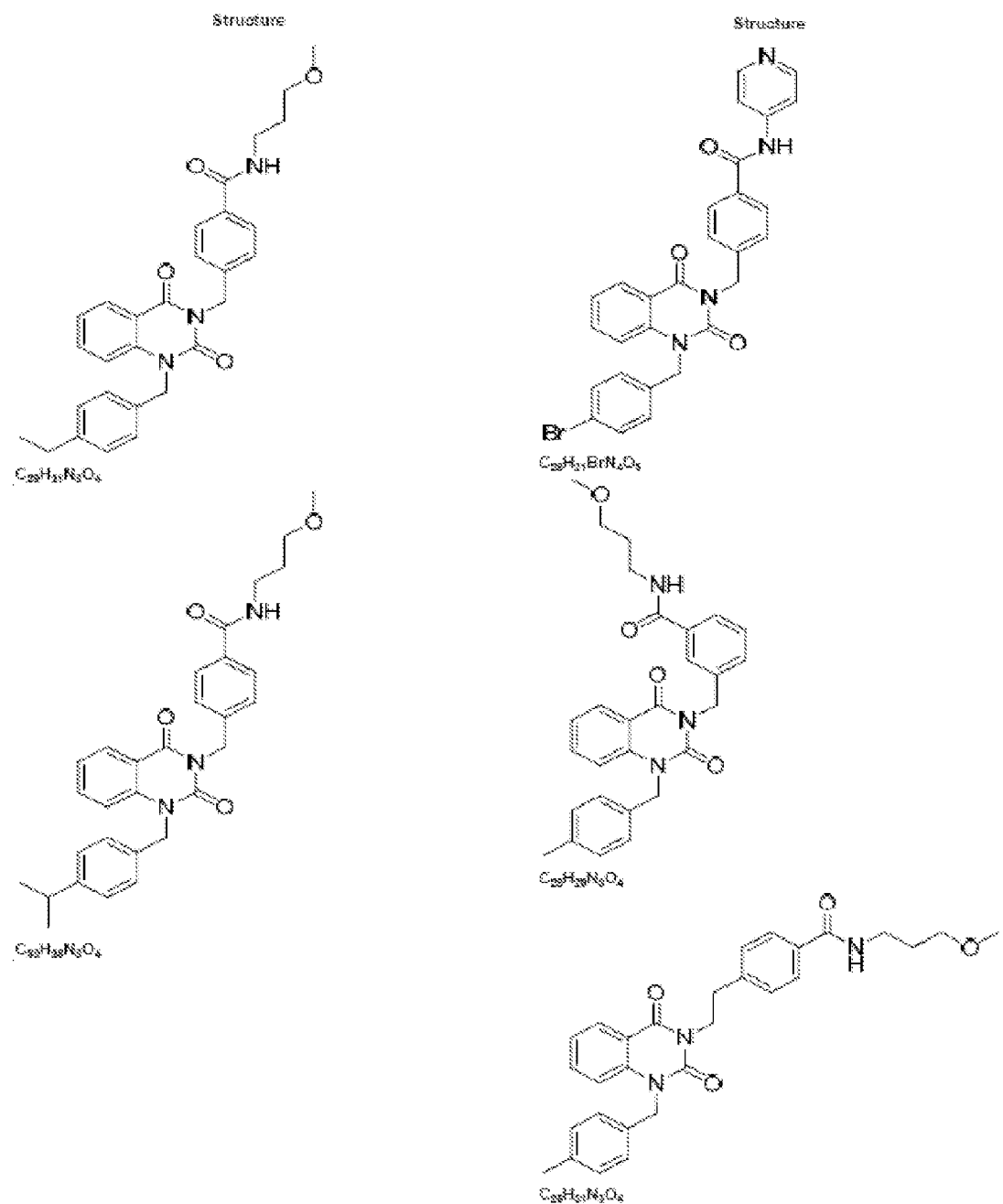
Figure 7:
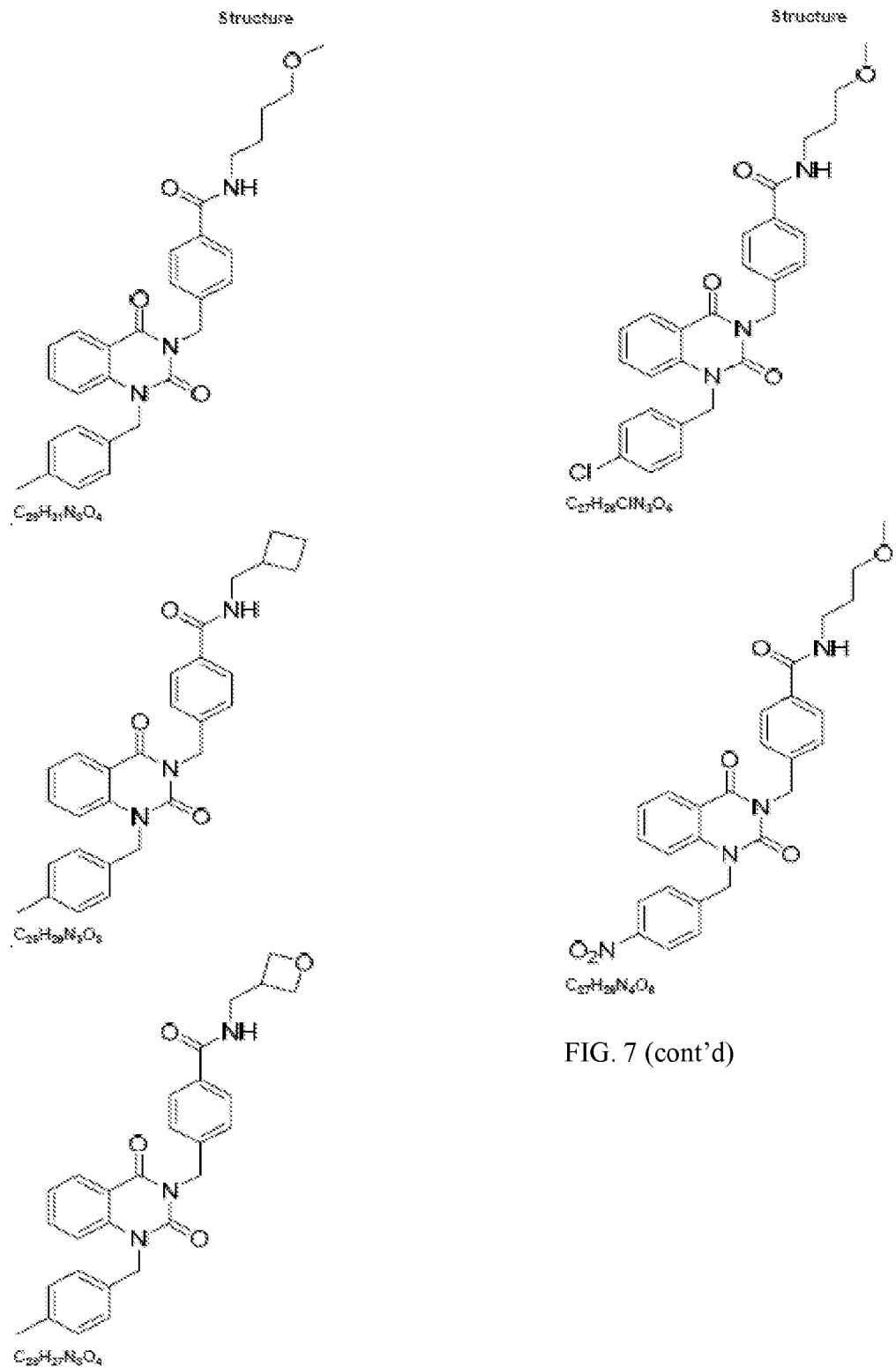
Figure 7:
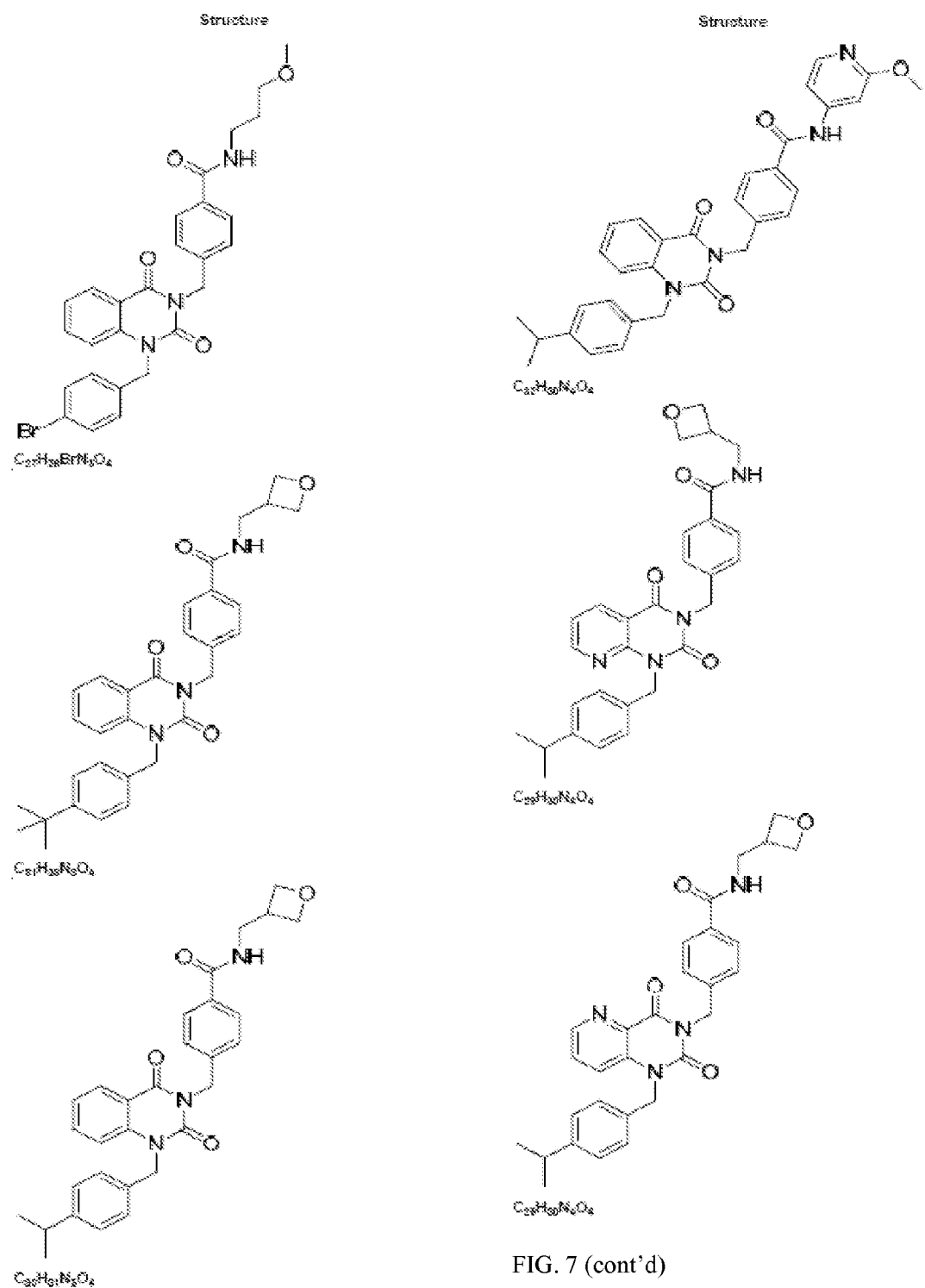
Figure 7:
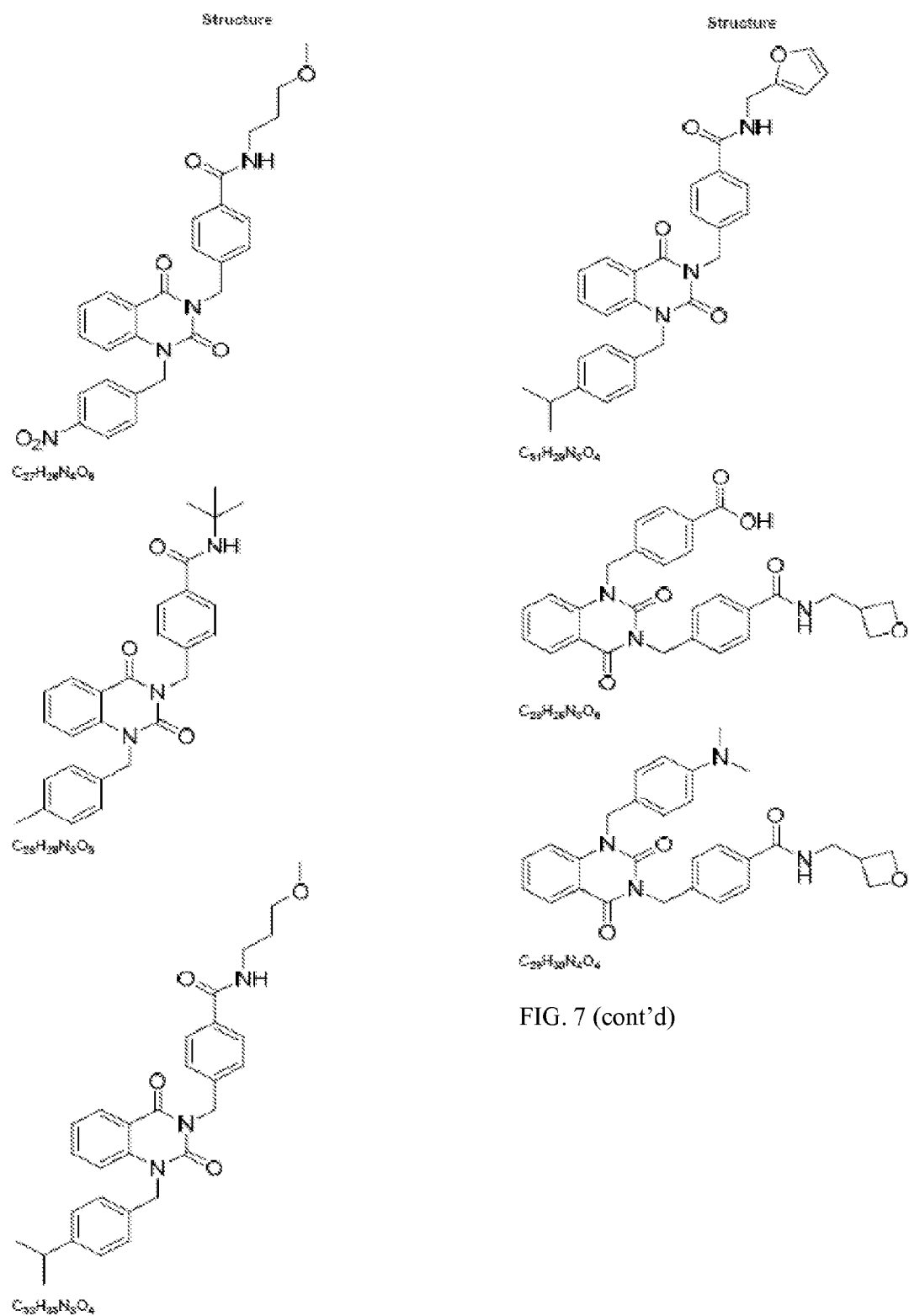
Figure 7:
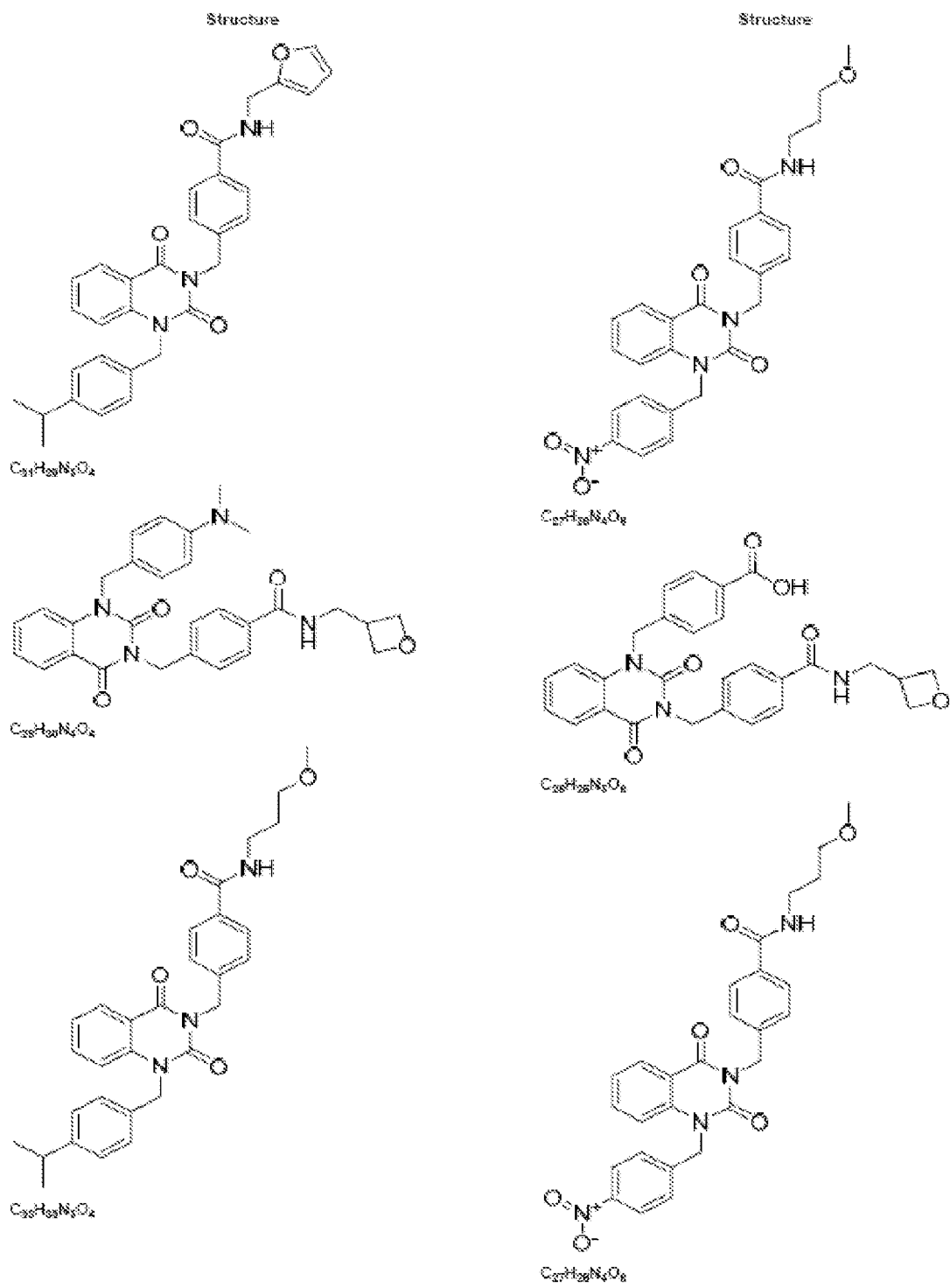
Figure 7:
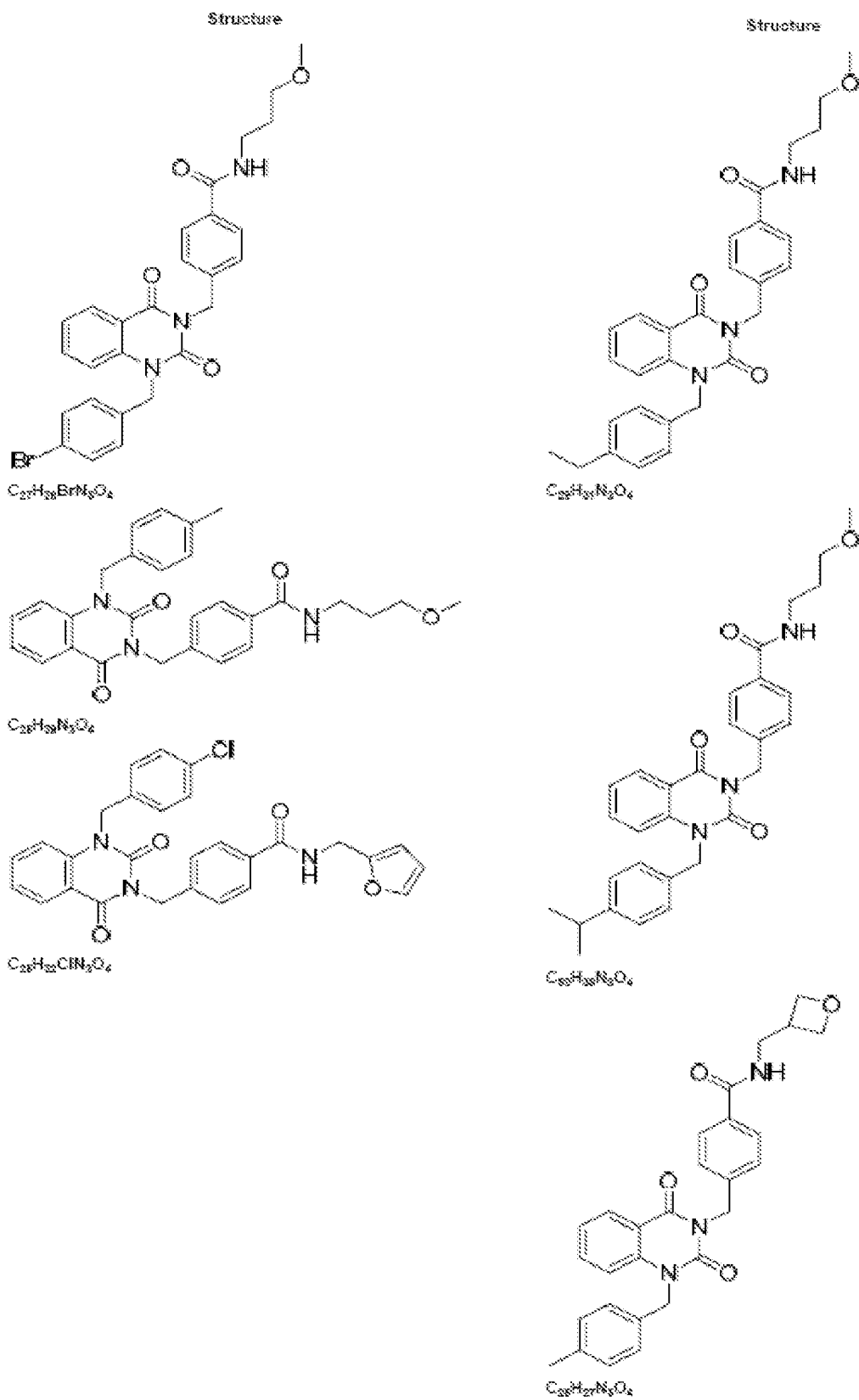
Figure 7:
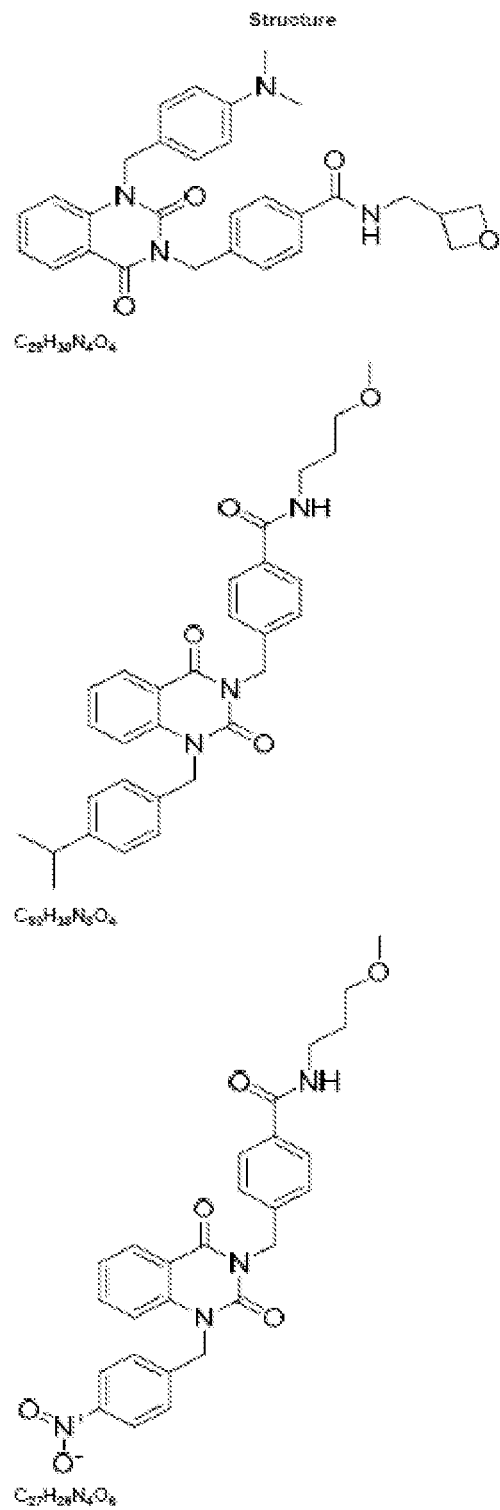

Other compounds include those compounds described herein. For example, compounds include those illustrated in FIG. 7.

a. Preparation of Compounds

Certain compounds described herein may be commercially available. These and other compounds described herein may also be prepared according to the methods set forth in Schemes 1-3.

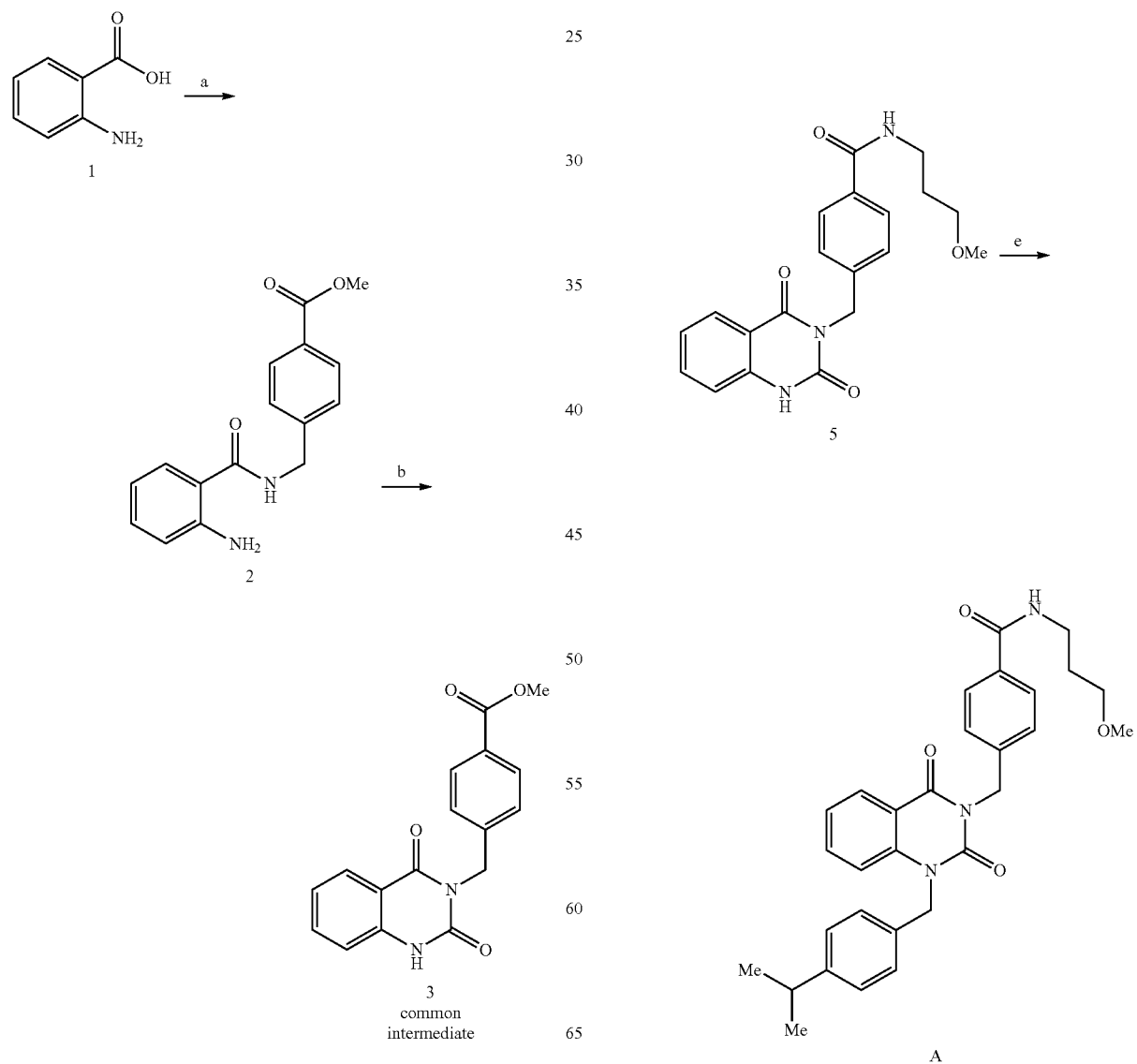

Scheme 3. Synthesis of Compound F

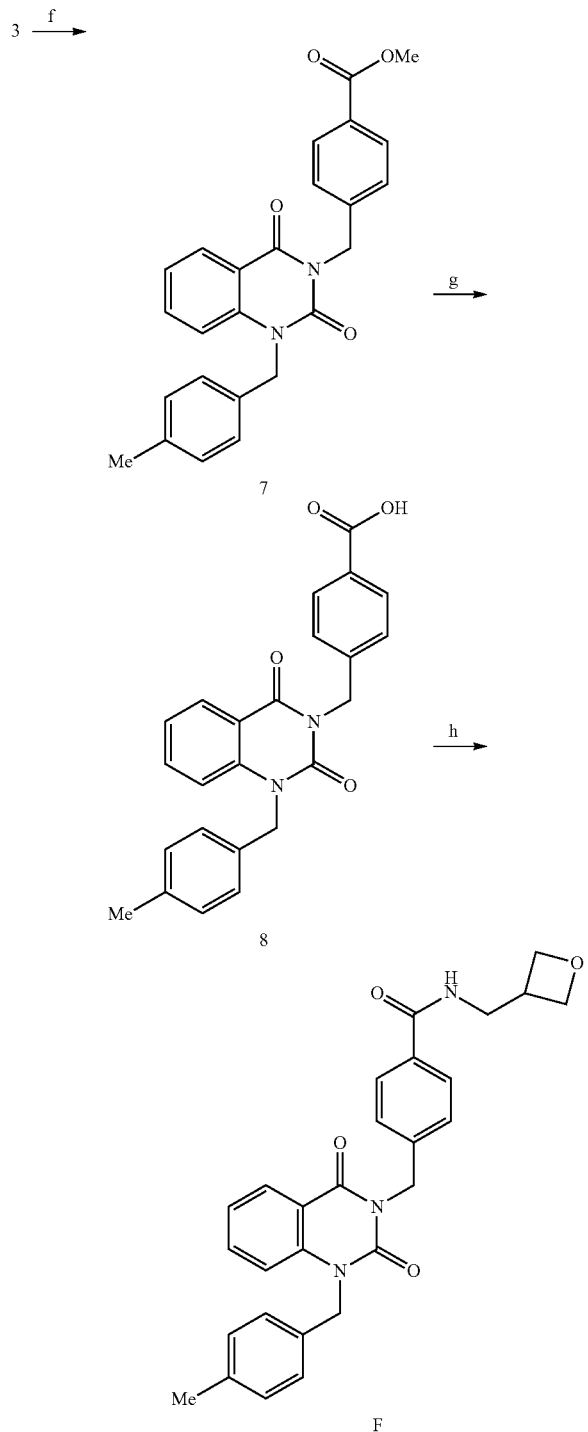

In Schemes 1-3, the indicated reagents and conditions are: (a) N,N-diisopropylethylamine (DIPEA), 2-(7-Aza-1H-benzotriazole-1-yl)-1,1,3,3-tetramethyluronium hexafluorophosphate (HATU), methyl 4-(aminomethyl)benzoate hydrochloride, dimethylformamide (DMF), rt, 2 h; (b) DIPEA, 1,1-carbonyldiimidazole, dichloromethane (DCM), reflux, 16 h; (c) LiOH.H$_2$O, tetrahydrofuran (THF), 40° C., 1 h; (d) DIPEA, HATU, 3-methoxypropylamine, DMF, rt, 2 h; (e) K$_2$CO$_3$, 4-isopropylbenzyl bromide or other aromatic halide for analogs, DMF, 40° C., 16 h; (f) K$_2$CO$_3$, 4-methylbenzyl bromide or other aromatic halide for similar analogs, DMF, 40° C., 16 h; (g) LiOH.H$_2$O, THF, 40° C., 3 h; (h) 4-dimethylaminopyridine (DMAP), 1-ethyl-3-(3-dimethylaminopropyl)carbodiimide hydrochloride (EDCI.HCl), 3-aminomethyloxetane, DCM, rt, 16 h.

As illustrated in Scheme 1, commercially available 2-aminobenzoic acid 1, coupled to the requisite benzylamine, affords aminoamide 2 which can be cyclized with CDI to provide quinazolinedione intermediate 3. Intermediate 3 can be used to generate the compounds through two related methods, each offering selective, orthogonal, late stage diversification of key functionality. Some compounds can be afforded by the protocol illustrated in Scheme 2, which involves hydrolysis of the ester, subsequent coupling with the desired alkylamine (e.g., 5), and installation of the core N-alkyl appendage to generate final compounds (e.g., A). For analogs bearing a cyclic moiety such as an oxetane, it may be advantageous to incorporate that structural entity late-stage (Scheme 3). The core N-alkyl appendage can be introduced (e.g., 7) from intermediate 3, followed by routine coupling manipulation to deliver final compounds (e.g., F). Specific experimental details are described in the Examples.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents or Organic Synthesis, John Wiley and Sons (1995), and subsequent editions thereof.

b. Isomers

Certain compounds may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half chair-forms; and combinations thereof, hereinafter collectively referred to as "isomers" (or "isomeric forms").

In one embodiment, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Compounds may be prepared in racemic form or as individual enantiomers or diastereomers by either stereo-specific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_3$-alkyl or propyl includes n-propyl and iso-propyl; $C_4$-alkyl or butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

c. Salt Forms

A compound described herein can be in the form of a salt, e.g., a pharmaceutically acceptable salt. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds or separately by reacting a compound with a suitable acid or base, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts." J. Pharm. Sci. Vol. 66, pp. 1-19.

Representative acid addition salts can be prepared using various suitable acids for example, including, but are not limited to, acetic, adipic, alginic, citric, aspartic, benzoic, benzenesulfonic, butyric, camphoric, camphorsulfonic, carbonic, digluconic, glycerophosphoric, heptanoic, hexanoic, fumaric, hydrochloric, hydrobromic, hydroiodic, 2-hydroxyethansulfonic (isethionic), lactic, maleic, methanesulfonic, nicotinic, 2-naphthalenesulfonic, oxalic, pamoic, pectinic, persulfuric, 3-phenylpropionic, picric, pivalic, propionic, succinic, sulfuric, tartaric, thiocyanic, phosphoric, glutamatic, p-toluenesulfonic, and undecanoic acids.

Particular examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, tartaric acid, and citric acid.

Basic addition salts can be prepared in situ during the final isolation and purification of compounds by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Unless otherwise specified, a reference to a particular compound also includes salt forms thereof.

d. Chemically Protected Forms

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(O)CH$_3$, —OAc).

An aldehyde or ketone group may be protected as an acetal (RCH(OR)$_2$) or ketal (R$_2$C(OR)$_2$), respectively, in which the carbonyl group (R$_2$C=O) is converted to a diether (R$_2$C(OR)$_2$), by reaction with, for example, a primary alcohol. The aldehyde or ketone group is readily regenerated by hydrolysis using an excess of water in the presence of acid.

An amine group may be protected, for example, as an amide (—NRC(O)R) or a urethane (—NRC(O)OR), for example, as: a methyl amide (—NHC(O)CH$_3$); a benzyloxy amide (—NHC(O)OCH$_2$C$_6$H$_5$, —NH-Cbz); as a t-butoxy amide (—NHC(O)OC(CH$_3$)$_3$, —NH-Boc); a 2-biphenyl-2-propoxy amide (—NHCO(O)C(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2-(phenylsulfonyl)ethyloxy amide (—NH-Psec); or, in suitable cases (e.g., cyclic amines), as a nitroxide radical.

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; or an acetamidomethyl ether (—S—CH$_2$NHC(O)CH$_3$).

e. Prodrugs and Other Modifications

In addition to salt forms, the present disclosure may also provide compounds that are in a prodrug form. Prodrugs of the compounds described herein are those compounds that readily undergo chemical changes under physiological conditions to provide the compounds described herein. The term "pharmaceutically acceptable prodrug" or "prodrug," as used herein, represents those prodrugs of the compounds which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the disclosure can be rapidly transformed in vivo to a parent compound, for example, by hydrolysis. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include but are not limited to esterification with polyethylene glycols, derivatization with pivolates or fatty acid substituents, conversion to carbamates, hydroxylation of aromatic rings, and heteroatom substitution in aromatic rings.

f. Evaluation of Compounds

Compounds can be evaluated by determining their ability to inhibit the virus-induced cytopathic effect (CPE) by reducing respiratory syncytial virus replication. Specifically, compounds can be evaluated using an in vitro human cell/virus infection model. Compounds can also be screened using a simple, phenotypic, cytoprotection high-throughput screening (HTS) assay.

For example, the inhibition of the CPE caused by RSV infection in HEp-2 cells can be used as an primary assay to identify the antiviral effects of compounds screened. The phenotypic end-point assay measures the luminescence generated by cellular ATP as a marker of cell viability. Confirmed, non-toxic compounds can be further investigated and subjected to chemical optimization, followed by secondary assay evaluation. Secondary assays can be used to closely characterize the ability of the compounds to reduce RSV replication and to examine the mechanism of action of the compounds by determining their point of intervention in the viral life cycle. The combination of primary assay (to measure cytoprotection), counter assay (for general eukaryotic cell toxicity) and secondary assay (to measure reduction in viral replication rates and point of intervention) combine to allow for a determination of probe efficacy, selectivity, and specificity.

Once the point of intervention for the probe is determined as either entry or post-entry inhibition, optimal compound criteria can be set as: CPE EC$_{50}$<1 µM for entry inhibitors; CPE EC$_{50}$<5 µM for post-entry inhibitors; a selective index >30× the EC$_{50}$ for the dose-response assay versus the observed cytotoxicity; titer reduction ≥1 log in virus reduction; and a differential response over time in the time of addition assay. Compounds meeting these criteria would represent an improvement over ribavirin.

For example, as is further detailed in the Examples, Compound A is a post-entry inhibitor with a CPE assay $EC_{50}=0.81\pm0.75$ μM, a selectivity index (SI) of >247 for antiviral activity over HEp-2 cell cytotoxicity, and a 6.7 log reduction in viral titer at 10 μM. Compound A has an $IC_{50}$ in the sub-micromolar range, a selective index >200, and >one million-fold reduction in viral titer. Data for Compounds A, B, C, D, E and F are illustrated in Table 2.

compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions can be administered to subjects (e.g., humans and other mammals) orally, rectally, parenterally, intracisternally, intravaginally, intraperitoneally, topically (as by powders, ointments or drops), bucally or as an oral or nasal spray. The term "parenterally," as used

TABLE 2

Selected Data for Compounds A-F.[i]

| Compound | CPE Assay $EC_{50}$ μM | $CC_{50}$ μM | Selectivity Index ($CC_{50}/EC_{50}$) | Plaque Reduction Assay (log reduction) | PBS Solubility (μg/mL and μM)[b] | CPE Assay Media Solubility (μg/mL and μM)[b] | Stability in PBS (% parent remaining after 48 h)[c] | PAMPA Permeability ($\times 10^{-6}$ cm/s)[d] | Hepatocyte Toxicity[e] $LC_{50}$ |
|---|---|---|---|---|---|---|---|---|---|
| A | 0.18 ± 0.75 | >200 | >247.0 | 6.70 | 0.18 μg/mL = 0.36 μM | 5.1 μg/mL = 10.21 μM | 27% (PBS); 100% (with acetonitrile) | 718/631/703 (see note)[g] | >30 μM |
| B | 0.57 ± 0.030[a] | >128 ± 31[a] | >224.0[a] | >5.56[a] | 0.63 μg/mL = 1.25 μM | 1.4 μg/mL = 2.79 μM | 83.4% (PBS); 94.9% (with acetonitrile) | 364/349/356 (see note)[h] | >50 μM |
| C | 0.85 ± 0.15 | 98.85 ± 8.70 | 118.9 | 4.07 | 0.31 μg/mL = 0.58 μM | 2.7 μg/mL = 5.03 μM | 57.5% (PBS); 100% (with acetonitrile) | NT | NT |
| D | 1.00 ± 0.05 | 94.85 ± 3.75 | 94.9 | 5.90 | NT | 1.5 μg/mL = 3.09 μM | NT | NT | NT |
| E | 1.07 ± 0.22 | 44.73 ± 7.22 | 41.8 | >6.18 | 5.60 μg/mL = 11.23 μM | 9.2 μg/mL = 18.45 μM | NT | NT | NT |
| F | 0.71 ± 0.13 | 46.96 ± 1.90 | 66.1 | 5.1 | 4.50 μg/mL = 0.75 μM | 4.5 μg/mL = 9.58 μM | NT | NT | NT |

NT = not tested;
[a]Average values reported.
[b]For complete conditions, see Example 2;
[c]Stability assessment was done independently in PBS or with 50% acetonitrile, the latter to account for solubility limitations affecting the PBS results;
[d]PAMPA done with Donor pH: 5.0/6.2/7.4, Acceptor pH: 7.4; controls: Verapamil (222/1097/1936 - highly permeable), Metoprolol (14//60/472 - moderately permeable), Ranitidine (<10/<10/<10 - poorly permeable);
[e]Fa2N-4 Immortalized Human Hepatocytes.
[g]PAMPA experiment done with 20% acetonitrile added to compensate for PBS solubility limitations;
[h]PAMPA experiment done with PBS, no additives.
[i]The RSV CPE assay was repeated for Compounds A and B, and provided values of 0.34 μM and 0.20 μM respectively.

Further description of methods used to evaluate compounds can be found in the Examples.

3. Pharmaceutical Compositions

The disclosure also provides pharmaceutical compositions comprising a compound of formula (I), (II) and/or (III), and a pharmaceutically acceptable carrier. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like.

Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Dosage forms for topical or transdermal administration of a compound include ointments, pastes, creams, lotions, gels, powders, solutions, sprays, inhalants or patches. A desired compound is admixed under sterile conditions with a pharmaceutically acceptable carrier and any needed preservatives or buffers as may be required. Ophthalmic formulation, eardrops, eye ointments, powders and solutions are also contemplated as being within the scope of this disclosure.

The ointments, pastes, creams and gels may contain, in addition to an active compound, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds, lactose, talc, silicic acid, aluminum hydroxide, calcium silicates and polyamide powder, or mixtures of these substances. Sprays can additionally contain customary propellants such as chlorofluorohydrocarbons.

Compounds also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

Dosage forms for topical administration of a compound described herein include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this disclosure. Aqueous liquid compositions may also be useful.

4. Methods of Use

The methods described herein include methods of treating of treating a respiratory syncytial virus infection in a subject in need of treatment, comprising administering to the subject a therapeutically effective amount of a compound described herein, such as a compound of formula (I), (II) or (III). Also described herein are methods inhibiting replication of respiratory syncytial virus, comprising contacting a sample comprising respiratory syncytial virus with an effective amount of a compound described herein, such as a compound of formula (I), (II) or (III).

It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

The present disclosure has multiple aspects, some of which are illustrated by the following non-limiting examples.

Example 1

Synthesis of Compounds

General Experimental and Analytical Details $^{1}$H and $^{13}$C NMR spectra were recorded on a Bruker AM 400 spectrometer (operating at 400 and 101 MHz respectively) or a Bruker AVIII spectrometer (operating at 500 and 126 MHz respectively) in CDCl$_3$ with 0.03% TMS as an internal standard or DMSO-d$_6$. The chemical shifts (δ) reported are given in parts per million (ppm) and the coupling constants (J) are in Hertz (Hz). The spin multiplicities are reported as s=singlet, br. s=broad singlet, d=doublet, t=triplet, q=quartet, dd=doublet of doublet and m=multiplet. The LCMS analysis was performed on an Agilent 1200 RRL chromatograph with photodiode array UV detection and an Agilent 6224 TOF mass spectrometer. The chromatographic method utilized the following parameters: a Waters Acquity BEH C-18 2.1×50 mm, 1.7 um column; UV detection wavelength=214 nm; flow rate=0.4 ml/min; gradient=5-100% acetonitrile over 3 minutes with a hold of 0.8 minutes at 100% acetonitrile; the aqueous mobile phase contained 0.15% ammonium hydroxide (v/v). The mass spectrometer utilized the following parameters: an Agilent multimode source which simultaneously acquires ESI+/APCI+; a reference mass solution consisting of purine and hexakis(1H, 1H, 3H-tetrafluoropropoxy)phosphazine; and a make-up solvent of 90:10:0.1 MeOH:Water:Formic Acid which was introduced to the LC flow prior to the source to assist ionization. Melting points were determined on a Stanford Research Systems OptiMelt apparatus.

Methyl 4-((2-aminobenzamido)methyl)benzoate

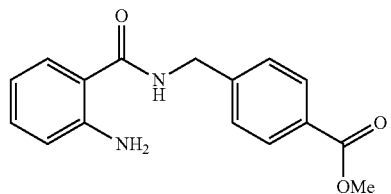 [SMILES: COC(=O)c1ccc(CNC(=O)c2ccccc2N)cc1]

To a solution of 2-aminobenzoic acid (1.50 g, 10.94 mmol) in N,N-dimethylformamide (12 mL) was added methyl 4-(aminomethyl)benzoate hydrochloride (2.21 g, 10.94 mmol), HATU (4.57 g, 12.03 mmol) and N,N-diisopropylethylamine (5.42 mL, 32.80 mmol). The reaction mixture was stirred for 16 h at room temperature, then diluted with dichloromethane (50 mL) and washed sequentially with 1M HCl (40 mL), sat. aqueous NaHCO$_3$ (40 mL) and water (2×200 mL). The separated organic extract was dried (MgSO$_4$), filtered, and concentrated under reduced pressure to afford a crude product which was purified by silica gel flash column chromatography (0-60% v/v EtOAc/Hexane), yielding the product as a white solid (1.88 g, 6.61 mmol, 61% yield). ¹H NMR (400 MHz; CDCl₃): δ (ppm) 8.01 (d, J=8.4 Hz, 2H), 7.41 (d, J=8.6 Hz, 2H), 7.35 (dd, J=7.9 and 1.4 Hz, 1H), 7.25-7.19 (m, 1H), 6.70 (dd, J=8.3 and 0.9 Hz, 1H), 6.67-6.61 (m, 1H), 6.43 (broad s, 1H), 5.56 (broad s, 2H), 4.66 (d, J=5.9 Hz, 2H), 3.91 (s, 3H).

Methyl 4-((2,4-dioxo-1,2-dihydroquinazolin-3(4H)-yl)methyl)benzoate

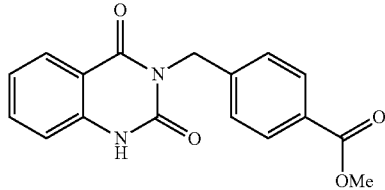 [SMILES: COC(=O)c1ccc(Cn2c(=O)[nH]c3ccccc3c2=O)cc1]

After stirring a solution of methyl 4-((2-aminobenzamido)methyl)benzoate (3.05 g, 10.73 mmol) and N,N-diisopropylethylamine (8.87 ml, 53.60 mmol) in CH₂Cl₂ (125 mL) for 10 minutes at room temperature under nitrogen, 1,1'-carbonyldiimidizaole (5.22 g, 32.20 mmol) was added, and the reaction mixture was heated 16 h at reflux. The formed precipitate was filtered, dried under vacuum and the desired product was furnished as a white solid without further purification (3.16 g, 10.18 mmol, 95% yield). ¹H NMR (400 MHz; DMSO): δ (ppm) 11.58 (s, 1H), 7.94 (dd, J=8.3 and 1.4 Hz, 1H), 7.90 (d, J=8.4 Hz, 2H), 7.72-7.64 (m, 1H), 7.43 (d, J=8.4 Hz, 2H), 7.26-7.18 (m, 2H), 5.15 (s, 2H), 3.83 (s, 3H).

4-((2,4-dioxo-1,2-dihydroquinazolin-3(4H)-yl)methyl)benzoic acid

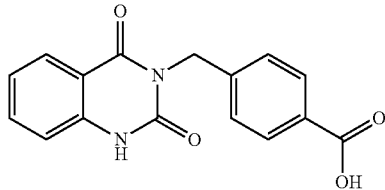 [SMILES: O=C(O)c1ccc(Cn2c(=O)[nH]c3ccccc3c2=O)cc1]

To a solution of methyl 4-((2,4-dioxo-1,2-dihydroquinazolin-3(4H)-yl)methyl)benzoate (1.00 g, 3.23 mmol) in THF (20 mL) was added 1 M lithium hydroxide in water (19.35 mL, 19.35 mmol). The reaction mixture was stirred at 40° C. for 1 hr, at which point TLC confirmed reaction completion. Then 1 M HCl was cautiously added until the reaction mixture reached pH 2, at which point the product precipitated out of solution. The precipitate was collected by filtration, washed with water (2×25 mL), dried under high vacuum to afford the desired product as a white solid (0.84 g, 2.84 mmol, 88% yield). ¹H NMR (400 MHz; DMSO): δ (ppm) 12.90 (broad s, 1H), 11.58 (s, 1H), 7.95 (d, J=7.3 Hz, 1H), 7.88 (d, J=8.3 Hz, 2H), 7.74-7.65 (m, 1H), 7.40 (d, J=8.3 Hz, 2H), 7.28-7.18 (m, 2H), 5.15 (s, 2H).

4-((2,4-dioxo-1,2-dihydroquinazolin-3(4H)-yl)methyl)-N-(3-methoxypropyl)benzamide

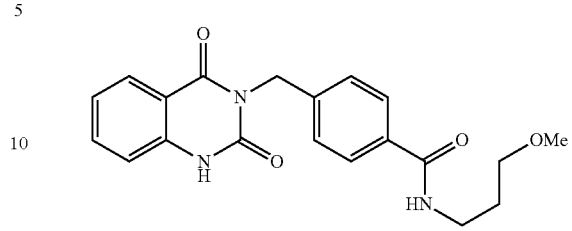

To a solution of 4-((2,4-dioxo-1,2-dihydroquinazolin-3(4H)-yl)methyl)benzoic acid (1.00 g, 3.38 mmol) in N,N-dimethylformamide (15 mL) was added 3-methoxypropylamine (0.35 mL, 3.38 mmol), HATU (1.41 g, 3.71 mmol) and N,N-diisopropylethylamine (1.67 mL, 10.13 mmol). The reaction mixture was stirred for 16 h at room temperature, then diluted with CH₂Cl₂ (90 ml) and washed sequentially with 1 M HCl (60 mL), sat. aqueous NaHCO₃ (60 mL) and water (2×180 mL). The organic extract was separated, dried (MgSO₄), filtered, and concentrated under reduced pressure to afford a crude product which was purified by silica gel flash column chromatography (0-5% v/v MeOH/CH₂Cl₂) yielding the desired product as a white solid (0.91 g, 2.48 mmol, 73% yield). ¹H NMR (400 MHz; DMSO): δ (ppm) 11.56 (s, 1H), 8.40 (t, J=5.6 Hz, 1H), 7.95 (d, J=7.3 Hz, 1H), 7.76 (d, J=8.4 Hz, 2H), 7.71-7.63 (m, 1H), 7.36 (d, J=8.4 Hz, 2H), 7.26-7.17 (m, 2H), 5.13 (s, 2H), 3.35 (t, J=6.3 Hz, 2H), 3.31-3.24 (m, 2H), 3.22 (s, 3H), 1.78-1.67 (m, 2H).

4-((1-(4-isopropylbenzyl)-2,4-dioxo-1,2-dihydroquinazolin-3(4H)-yl)methyl)-N-(3-methoxypropyl)benzamide (Compound A)

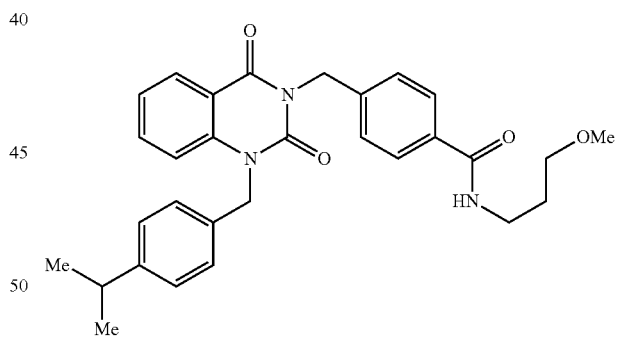

To a solution of 4-((2,4-dioxo-1,2-dihydroquinazolin-3(4H)-yl)methyl)-N-(3-methoxypropyl)benzamide (0.050 g, 0.14 mmol) in N,N-dimethylformamide (2 mL) was added 4-isopropylbenzyl bromide (0.028 mL, 0.16 mmol) and potassium carbonate (0.056 g, 0.41 mmol). The resulting reaction mixture was stirred at 40° C. for 16 h. The formed residue was dissolved in CH₂Cl₂ (6 mL) and sequentially washed with 1 M HCl (4 mL), water (3×20 mL) and brine (8 mL). The organic layer was separated, dried (MgSO₄), filtered, and concentrated under reduced pressure to give a crude product which was purified by silica gel flash column chromatography (0-5% v/v MeOH/DCM) yielding 4-((1-(4-isopropylbenzyl)-2,4-dioxo-1,2-dihydroquinazolin-3(4H)-yl)methyl)-N-(3-methoxypropyl)benzamide as a white solid (0.030 g, 0.060 mmol, 44% yield). $^1$H NMR (500 MHz; CDCl$_3$): δ (ppm) 8.24 (dd, J=7.9 and 1.6 Hz, 1H), 7.71 (d, J=8.3 Hz, 2H), 7.61-7.53 (m, 3H), 7.22 (apparent t, J=7.5 Hz, 1H), 7.20-7.13 (m, 5H), 6.89 (t, J=4.5 Hz, 1H), 5.36 (s, 2H), 5.33 (broad s, 2H), 3.60-3.52 (m, 4H), 3.37 (s, 3H), 2.92-2.81 (m, 1H), 1.87 (quintet, J=5.9 Hz, 2H), 1.21 (d, J=6.9 Hz, 6H). $^{13}$C NMR (126 MHz; CDCl$_3$): δ (ppm) 166.98, 161.89, 151.45, 148.51, 140.38, 140.13, 135.36, 134.12, 132.86, 129.22, 129.07, 127.15, 127.14, 126.53, 123.26, 115.71, 114.65, 72.55, 59.06, 47.31, 44.90, 39.27, 33.84, 28.91, 24.01. LCMS retention time: 3.422 min. LCMS purity at 214 nm: 98.8%. HRMS: m/z calcd for C$_{30}$H$_{33}$N$_3$O$_4$ (M+H$^+$) 500.2544. found 500.2540. Melting point: 171-173° C.

N-(3-methoxypropyl)-4-((1-(4-nitrobenzyl)-2,4-dioxo-1,2-dihydroquinazolin-3(4H)-yl)methyl)benzamide (Compound B)

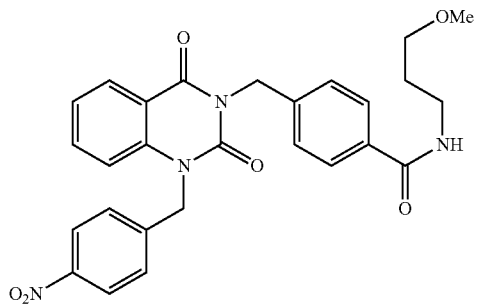 [SMILES: COCCCNC(=O)c1ccc(Cn2c(=O)c3ccccc3n(Cc3ccc([N+](=O)[O-])cc3)c2=O)cc1]

To a solution of 4-((2,4-dioxo-1,2-dihydroquinazolin-3(4H)-yl)methyl)-N-(3-methoxypropyl)benzamide (0.032 g, 0.087 mmol) in DMF (1.6 mL) was added 4-nitrobenzyl chloride (0.018 g, 0.10 mmol) and potassium carbonate (0.036 g, 0.26 mmol). The resulting reaction mixture was stirred at 40° C. for 16 h. The residue thus formed was dissolved in CH$_2$Cl$_2$ (5 mL) and washed sequentially with 1M HCl (3 mL), water (3×15 mL) and brine (6 mL). The separated organic layer was dried (MgSO$_4$), filtered, and concentrated under reduced pressure to give the crude product which was purified by silica gel flash column chromatography (0-5% v/v MeOH/CH$_2$Cl$_2$), yielding N-(3-methoxypropyl)-4-((1-(4-nitrobenzyl)-2,4-dioxo-1,2-dihydroquinazolin-3(4H)-yl)methyl)benzamide as a pale yellow solid (0.021 g, 0.042 mmol, 48% yield). $^1$H NMR (500 MHz; CDCl$_3$): δ (ppm) 8.29 (dd, J=7.9 and 1.5 Hz, 1H), 8.20 (d, J=8.8 Hz, 2H), 7.72 (d, J=8.4 Hz, 2H), 7.61-7.54 (m, 3H), 7.40 (d, J=8.8 Hz, 2H), 7.28 (apparent t, J=7.3 Hz, 1H), 6.98 (d, J=8.4 Hz, 1H), 6.90 (t, J=4.5 Hz, 1H), 5.46 (broad s, 2H), 5.36 (s, 2H), 3.60-3.52 (m, 4H), 3.38 (s, 3H), 1.87 (quintet, J=5.9 Hz, 2H). $^{13}$C NMR (126 MHz; CDCl$_3$): δ (ppm) 166.88, 161.61, 151.40, 147.68, 143.13, 140.05, 139.56, 135.62, 134.36, 129.73, 129.20, 127.38, 127.22, 124.46, 123.85, 115.87, 113.96, 72.64, 59.09, 47.10, 45.05, 39.36, 28.92. LCMS retention time: 2.973 min. LCMS purity at 214 nm: 97.8%. HRMS: m/z calcd for C$_{27}$H$_{26}$N$_4$O$_6$ (M+H$^+$) 503.1925. found 503.1951.

4-((1-(4-bromobenzyl)-2,4-dioxo-1,2-dihydroquinazolin-3(4H)-yl)methyl)-N-(3-methoxypropyl)benzamide (Compound C)

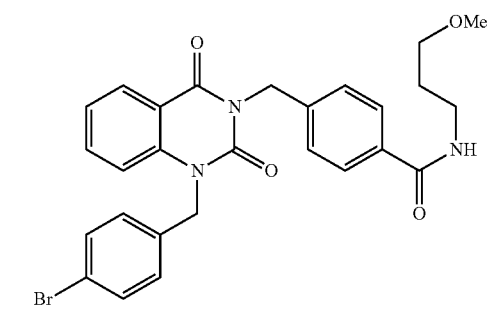 [SMILES: COCCCNC(=O)c1ccc(Cn2c(=O)c3ccccc3n(Cc3ccc(Br)cc3)c2=O)cc1]

To a solution of 4-((2,4-dioxo-1,2-dihydroquinazolin-3(4H)-yl)methyl)-N-(3-methoxypropyl)benzamide (0.032 g, 0.087 mmol) in DMF (1.6 mL) were added 4-bromobenzyl bromide (0.026 g, 0.10 mmol) and potassium carbonate (0.036 g, 0.26 mmol). The resulting reaction mixture was stirred at 40° C. for 16 h. The residue thus formed was dissolved in CH$_2$Cl$_2$ (5 mL) and sequentially washed with 1M HCl (3 mL), water (3×15 mL) and brine (6 mL). The separated organic layer was dried (MgSO$_4$), filtered, and concentrated under reduced pressure to give the crude product which was purified by silica gel flash column chromatography (0-5% v/v MeOH/CH$_2$Cl$_2$), yielding 4-((1-(4-bromobenzyl)-2,4-dioxo-1,2-dihydroquinazolin-3(4H)-yl)methyl)-N-(3-methoxypropyl)benzamide as a white solid (0.023 g, 0.043 mmol, 49% yield). $^1$H NMR (500 MHz; CDCl$_3$): δ (ppm) 8.25 (dd, J=7.9 and 1.6 Hz, 1H), 7.71 (d, J=8.3 Hz, 2H), 7.60-7.53 (m, 3H), 7.45 (d, J=8.4 Hz, 2H), 7.24 (apparent t, J=7.3 Hz, 1H), 7.11 (d, J=8.5 Hz, 2H), 7.05 (d, J=8.4 Hz, 1H), 6.89 (t, J=4.6 Hz, 1H), 5.35 (s, 2H), 5.31 (broad s, 2H), 3.59-3.53 (m, 4H), 3.37 (s, 3H), 1.87 (quintet, J=5.9 Hz, 2H). $^{13}$C NMR (126 MHz; CDCl$_3$): δ (ppm) 166.95, 161.77, 151.45, 140.25, 139.83, 135.49, 134.72, 134.26, 132.29, 129.47, 129.16, 128.32, 127.20, 123.56, 121.79, 115.81, 114.34, 72.62, 59.11, 47.06, 44.99, 39.33, 28.95. LCMS retention time: 3.208 min. LCMS purity at 214 nm: 99%. HRMS: m/z calcd for C$_{27}$H$_{26}$BrN$_3$O$_4$ (M+H$^+$) 538.1163. found 538.1191.

4-((1-(4-ethylbenzyl)-2,4-dioxo-1,2-dihydroquinazolin-3(4H)-yl)methyl)-N-(3-methoxypropyl)benzamide (Compound D)

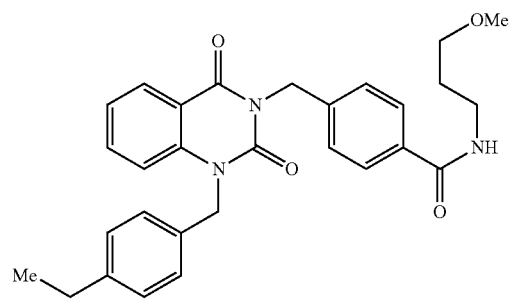 [SMILES: CCc1ccc(Cn2c(=O)n(Cc3ccc(C(=O)NCCCOC)cc3)c(=O)c3ccccc32)cc1]

To a solution of 4-((2,4-dioxo-1,2-dihydroquinazolin-3(4H)-yl)methyl)-N-(3-methoxypropyl)benzamide (0.100 g, 0.27 mmol) in DMF (4 mL) were added 4-ethylbenzyl chloride (0.049 ml, 0.33 mmol) and potassium carbonate (0.11 g, 0.82 mmol). The resulting reaction mixture was stirred at 40° C. for 16 h. The residue thus formed was dissolved in CH$_2$Cl$_2$ (12 mL) and washed sequentially with 1M HCl (8 mL), water (3×40 mL) and brine (16 mL). The separated organic layer was dried (MgSO$_4$), filtered, and concentrated under reduced pressure to give the crude product which was purified by silica gel flash column chromatography (0-5% v/v MeOH/CH$_2$Cl$_2$), yielding 4-((1-(4-ethylbenzyl)-2,4-dioxo-1,2-dihydroquinazolin-3(4H)-yl)methyl)-N-(3-methoxypropyl)benzamide as a white solid (0.088 g, 0.18 mmol, 67% yield). $^1$H NMR (500 MHz; CDCl$_3$): δ (ppm) 8.24 (dd, J=7.9 and 1.5 Hz, 1H), 7.71 (d, J=8.3 Hz, 2H), 7.61-7.51 (m, 3H), 7.22 (apparent t, J=7.3 Hz, 1H), 7.18-7.11 (m, 5H), 6.90 (t, J=4.6 Hz, 1H), 5.36 (s, 2H), 5.34 (broad s, 2H), 3.60-3.51 (m, 4H), 3.37 (s, 3H), 2.61 (q, J=7.6 Hz, 2H), 1.87 (quintet, J=5.9 Hz, 2H), 1.20 (t, J=7.6 Hz, 3H). $^{13}$C NMR (126 MHz; CDCl$_3$): δ (ppm) 166.98, 161.89, 151.46, 143.90, 140.38, 140.10, 135.36, 134.13, 132.77, 129.22, 129.08, 128.59, 127.15, 126.56, 123.26, 115.72, 114.64, 72.55, 59.06, 47.34, 44.91, 39.26, 28.93, 28.57, 15.58. LCMS retention time: 3.324 min. LCMS purity at 214 nm: 99.1%. HRMS: m/z calcd for C$_{29}$H$_{31}$N$_3$O$_4$ (M+H$^+$) 486.2387. found 486.2394.

Methyl 4-((1-(4-methylbenzyl)-2,4-dioxo-1,2-dihydroquinazolin-3(4H)-yl)methyl)benzoate

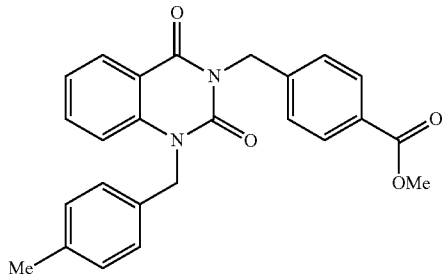 [SMILES: COC(=O)c1ccc(Cn2c(=O)c3ccccc3n(Cc3ccc(C)cc3)c2=O)cc1]

To a solution of methyl 4-((2,4-dioxo-1,2-dihydroquinazolin-3(4H)-yl)methyl)benzoate (0.30 g, 0.96 mmol) in DMF (12 mL) were added 4-methylbenzyl bromide (0.21 g, 1.16 mmol) and potassium carbonate (0.40 g, 2.89 mmol). The resulting reaction mixture was stirred at 40° C. for 16 h. The residue thus formed was dissolved in CH$_2$Cl$_2$ (32 mL) and washed sequentially with 1M HCl (20 mL), water (3×100 mL) and brine (40 mL). The organic layer was dried (MgSO$_4$), filtered, and concentrated under reduced pressure to afford the crude product which was purified by silica gel flash column chromatography (0-5% v/v MeOH/CH$_2$Cl$_2$), yielding the desired product as a white solid (0.28 g, 0.68 mmol, 70% yield). $^1$H NMR (400 MHz; CDCl$_3$): δ (ppm) 8.24 (dd, J=7.9 and 1.5 Hz, 1H), 7.99 (d, J=8.4 Hz, 2H), 7.61-7.51 (m, 3H), 7.25-7.19 (m, 1H), 7.17-7.10 (m, 5H), 5.38 (s, 2H), 5.33 (broad s, 2H), 3.90 (s, 3H), 2.31 (s, 3H).

4-((1-(4-methylbenzyl)-2,4-dioxo-1,2-dihydroquinazolin-3(4H)-yl)methyl)benzoic acid

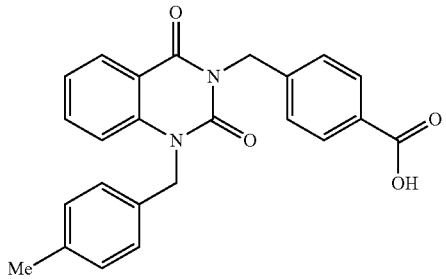 [SMILES: Cc1ccc(Cn2c(=O)n(Cc3ccc(C(=O)O)cc3)c(=O)c3ccccc32)cc1]

To a solution of methyl 4((1-(4-methylbenzyl)-2,4-dioxo-1,2-dihydroquinazolin-3(4H)-yl)methyl)benzoate (0.37 g, 0.90 mmol) in THF (6 mL) was added 1M lithium hydroxide (5.4 mL, 5.40 mmol). The reaction mixture was stirred at 40° C. for 3 hr, at which point TLC confirmed completion of reaction. Then 1M HCl was cautiously added until the reaction mixture was at pH 2, at which point the product precipitated out of solution. The precipitate was filtered, washed with H$_2$O (2×10 mL), collected and dried under high vacuum to afford the desired product as a white solid (0.32 g, 0.80 mmol, 89% yield). $^1$H NMR (400 MHz; DMSO): δ (ppm) 12.90 (s, 1H), 8.09 (dd, J=7.8 and 1.5 Hz, 1H), 7.90 (d, J=8.3 Hz, 2H), 7.73-7.65 (m, 1H), 7.45 (d, J=8.3 Hz, 2H), 7.35-7.25 (m, 2H), 7.19 (d, J=8.1 Hz, 2H), 7.13 (d, J=8.1 Hz, 2H), 5.34 (s, 2H), 5.27 (s, 2H), 2.25 (s, 3H).

4-((1-(4-methylbenzyl)-2,4-dioxo-1,2-dihydroquinazolin-3(4H)-yl)methyl)-N-(oxetan-3-ylmethyl)benzamide (Compound F)

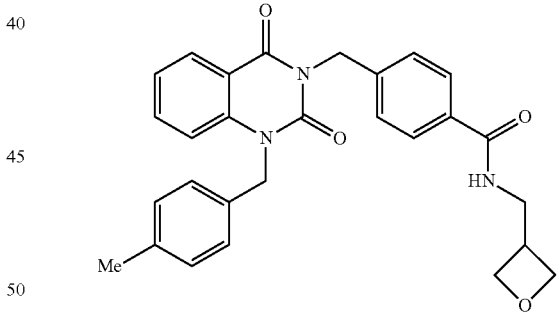

To a solution of 4-((1-(4-methylbenzyl)-2,4-dioxo-1,2-dihydroquinazolin-3(4H)-yl)methyl)benzoic acid (0.030 g, 0.075 mmol) in DCM (1.5 mL) was added 3-aminomethyl-oxetane (9.79 mg, 0.112 mmol) followed by 4-dimethylaminopyridine (0.037 g, 0.300 mmol) and 1-(3-dimethylaminopropyl)-3-ethylcarbodiimide hydrochloride (0.029 g, 0.15 mmol). The reaction was stirred for 16 h at rt. The mixture was sequentially washed with 1M HCl (1 mL) and saturated aqueous NaHCO$_3$ (1 mL). The separated organic layer was dried (MgSO$_4$), filtered and concentrated under reduced pressure to give the crude product which was purified by silica gel flash column chromatography (0-5% v/v MeOH/CH$_2$Cl$_2$), yielding 4-((1-(4-methylbenzyl)-2,4-dioxo-1,2-dihydroquinazolin-3(4H)-yl)methyl)-N-(oxetan-3-ylmethyl)benzamide as a white solid (0.024 g, 0.051 mmol, 68% yield). ¹H NMR (500 MHz; CDCl₃): δ (ppm) 8.23 (dd, J=7.9 and 1.6 Hz, 1H), 7.71 (d, J=8.3 Hz, 2H), 7.58 (d, J=8.3 Hz, 2H), 7.57-7.52 (m, 1H), 7.22 (apparent t, J=7.6 Hz, 1H), 7.17-7.09 (m, 5H), 6.36 (t, J=5.5 Hz, 1H), 5.36 (s, 2H), 5.33 (broad s, 2H), 4.82 (dd, J=7.6 and 6.4 Hz, 2H), 4.46 (apparent t, J=6.1 Hz, 2H), 3.73 (apparent t, J=6.3 Hz, 2H), 3.33-3.23 (m, 1H), 2.31 (s, 3H). ¹³C NMR (126 MHz; CDCl₃): δ (ppm) 167.80, 161.90, 151.47, 140.90, 140.09, 137.60, 135.42, 133.64, 132.53, 129.80, 129.23, 129.20, 127.23, 126.51, 123.33, 115.71, 114.65, 75.18, 47.36, 44.91, 42.55, 35.13, 21.22. LCMS retention time: 3.038 min. LCMS purity at 214 nm: 96.9%. HRMS: m/z calcd for $C_{28}H_{27}N_3O_4$ (M+H⁺) 470.2074. found 470.2070.

(4-dimethylamino)benzyl) 4-methyl)benzenesulfonate

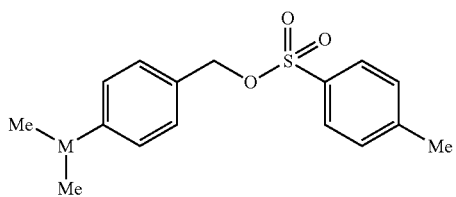

To a mixture of 4-(dimethylamino)benzyl alcohol (0.47 mL, 3.34 mmol) and triethylamine (0.93 mL, 6.68 mmol) in dry $CH_2Cl_2$ (8 mL) at 0° C. was added 4-toluenesulfonyl chloride (0.64 g, 3.34 mmol). The mixture was allowed to warm to rt and stirred for 2 hr, at which point TLC confirmed completion of reaction. The reaction mixture was washed sequentially with sat. aqueous $NaHCO_3$ (3×12 ml) and brine (12 ml). The separated organic layer was dried ($MgSO_4$), filtered and concentrated under reduced pressure. The crude product was carried into the next step without further purification.

Methyl 4-((1-(4-dimethylamino)benzyl)-2,4-dioxo-1,2-dihydroquinazolin-3(4H)-yl)methyl)benzoate

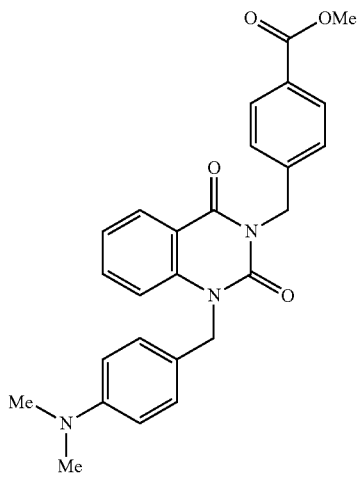 [SMILES: COC(=O)c1ccc(Cn2c(=O)c3ccccc3n(Cc3ccc(N(C)C)cc3)c2=O)cc1]

To a stirred suspension of sodium hydride (0.076 g, 1.89 mmol) in dry DMF (2.5 mL) at 0° C. was added methyl 4-((2,4-dioxo-1,2-dihydroquinazolin-3(4H)-yl)methyl)benzoate (0.24 g, 0.76 mmol) and the mixture was stirred for 15 min at 0° C. Then 4-(dimethylamino)benzyl 4-methylbenzenesulfonate (0.25 g, 0.83 mmol) in DMF (2.5 mL) was added to this suspension and the mixture heated at 80° C. for 16 hr. The mixture was then cooled to 0° C., quenched with water (5 mL), extracted with $CH_2Cl_2$ (3×8 mL). The organic extracts were washed with water (3×25 mL), brine (12 mL) and dried ($MgSO_4$), filtered and concentrated under reduced pressure to afford the crude product which was purified by reverse phase column chromatography (0-100% v/v MeCN/$H_2O$) yielding the desired product as a pale green solid (0.036 g, 0.081 mmol, 11% yield). ¹H NMR (400 MHz; CDCl₃): δ (ppm) 8.22 (dd, J=7.9 and 1.5 Hz, 1H), 8.04-7.95 (m, 2H), 7.61-7.52 (m, 3H), 7.26-7.18 (m, 2H), 7.14 (d, J=8.8 Hz, 2H), 6.66 (d, J=8.8 Hz, 2H), 5.37 (s, 2H), 5.27 (broad s, 2H), 3.90 (s, 3H), 2.91 (s, 6H).

4-((1-(4-dimethylamino)benzyl)-2,4-dioxo-1,2-dihydroquinazolin-3(4H)-yl)methyl)benzoic acid

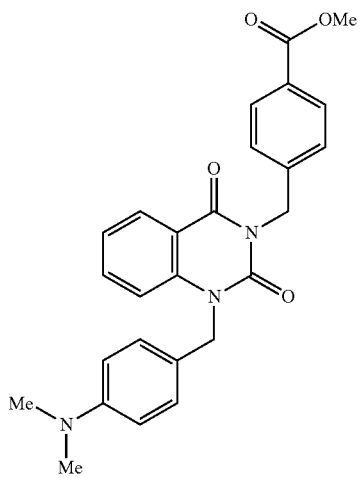 [SMILES: COC(=O)c1ccc(Cn2c(=O)c3ccccc3n(Cc3ccc(N(C)C)cc3)c2=O)cc1]

To a solution of methyl 4-((1-(4-(dimethylamino)benzyl)-2,4-dioxo-1,2-dihydroquinazolin-3(4H)-yl)methyl)benzoate (0.060 g, 0.14 mmol) in THF (1 mL) was added 1M lithium hydroxide (0.81 mL, 0.81 mmol). The reaction mixture was stirred at 40° C. for 3 hr, at which point TLC confirmed completion of reaction. Then 1M HCl was cautiously added until the reaction mixture was at pH 7 (isoelectric point), at which point the product precipitated out of solution. The precipitate was filtered, washed with $H_2O$ (2×6 mL), collected and dried under high vacuum to afford the desired product as a pale green solid (0.026 g, 0.061 mmol, 45% yield). ¹H NMR (400 MHz; DMSO): δ (ppm) 12.90 (s, 1H), 8.08 (d, J=7.5 Hz, 1H), 7.90 (d, J=8.2 Hz, 2H), 7.70 (apparent t, J=7.6 Hz, 1H), 7.44 (d, J=8.2 Hz, 2H), 7.40 (d, J=8.5 Hz, 1H), 7.28 (apparent t, J=7.5 Hz, 1H), 7.14 (d, J=8.6 Hz, 2H), 6.66 (d, J=8.6 Hz, 2H), 5.27 (s, 4H), 2.83 (s, 6H).

4-((1-(4-(dimethylamino)benzyl)-2,4-dioxo-1,2-dihydroquinazolin-3(4H)-yl)methyl)-N-(oxetan-3-ylmethyl)benzamide (Compound E)

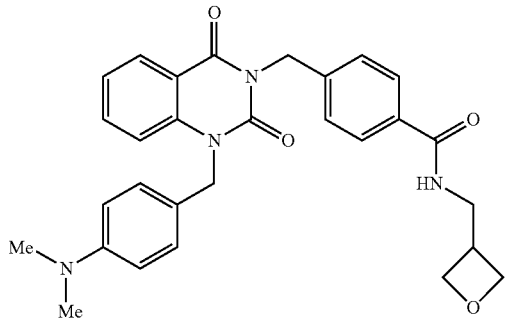 [SMILES: CN(C)c1ccc(Cn2c(=O)n(Cc3ccc(C(=O)NCC4COC4)cc3)c(=O)c3ccccc32)cc1]

To a solution of 4-((1-(4-(dimethylamino)benzyl)-2,4-dioxo-1,2-dihydroquinazolin-3(4H)-yl)methyl)benzoic acid (0.052 g, 0.12 mmol) in DMF (1 mL) were added 3-aminomethyl-oxetane (10.55 mg, 0.12 mmol), HBTU (0.051 g, 0.13 mmol) and N,N-diisopropylethylamine (0.060 mL, 0.36 mmol). The reaction mixture was stirred for 2 hr at rt, at which point TLC and LC-MS confirmed completion of reaction. The reaction mixture was diluted with $CH_2Cl_2$ (5 ml) and washed with sat. aqueous $NaHCO_3$ (2×5 mL) and water (2×30 mL). The separated organic layer was dried ($MgSO_4$), filtered, and concentrated under reduced pressure to afford the crude product which was purified by silica gel flash column chromatography (0-5% v/v $MeOH/CH_2Cl_2$), yielding 4-((1-(4-(dimethylamino)benzyl)-2,4-dioxo-1,2-dihydroquinazolin-3(4H)-yl)methyl)-N-(oxetan-3-ylmethyl) benzamide as a pale green solid (0.043 g, 0.086 mmol, 71% yield). $^1$H NMR (400 MHz; $CDCl_3$): δ (ppm) 8.21 (dd, J=7.9 and 1.5 Hz, 1H), 7.71 (d, J=8.3 Hz, 2H), 7.58 (d, J=8.3 Hz, 2H), 7.57-7.52 (m, 1H), 7.25-7.17 (m, 2H), 7.13 (d, J=8.8 Hz, 2H), 6.66 (d, J=8.8 Hz, 2H), 6.35 (t, J=5.7 Hz, 1H), 5.36 (s, 2H), 5.26 (broad s, 2H), 4.82 (dd, J=7.7 and 6.3 Hz, 2H), 4.46 (apparent t, J=6.0 Hz, 2H), 3.73 (apparent t, J=6.3 Hz, 2H), 3.33-3.22 (m, 1H), 2.91 (s, 6H). $^{13}$C NMR (126 MHz; $CDCl_3$): δ (ppm) 167.84, 161.98, 151.50, 150.19, 141.02, 140.24, 135.36, 133.59, 129.18, 129.15, 127.88, 127.23, 123.18, 123.03, 115.71, 114.80, 112.85, 75.20, 47.15, 44.88, 42.58, 40.64, 35.15. LCMS retention time: 3.054 min. LCMS purity at 214 nm: 91.3%. HRMS: m/z calcd for $C_{29}H_{30}N_4O_4$ (M+H$^+$) 499.2340. found 499.2338.

Example 2

Compound Screening Assays

1. Using Frozen Infected Cells-Based Assay for Evaluation of RSV Inhibitors

This cell-based assay measured the inhibition of RSV-induced cytopathic effect (CPE) in cells using luminescent cell viability assay readout.

The assay is sensitive and robust, with Z values >0.8, signal to background, S/B>35, and signal to noise, S/N>24. Various parameters were optimized and validated including cell density, viral concentration, DMSO tolerance for compound dilution, incubation time for virus-induced CPE and effective control drug concentration. Additional parameters, such as day to day assay variability, reagent and read stability, edge effects, and $EC_{50}$ stability were also examined during validation. The following is the statistical analysis report of screening a small pilot library.

Cell Culture:

HEp-2 cells (ATCC CCL-23, American Tissue Culture Type) were maintained as adherent cell lines in Optimem® 1 with 2 mM L-glutamine and 10% fetal bovine serum (FBS) at 37° C., 5% $CO_2$ atmosphere. Cells were passaged as needed and harvested from flasks using 0.05% trypsin-EDTA.

Assay Media—Preparation of Complete DMEM/F12®:

50 mL Pen/Strep/Glutamine (Gibco, Cat #10378) was added to four liters of room temperature DMEM/F12® (Sigma, Cat #D6434) and the pH adjusted to 7.5 using 1M NaOH. The medium was sterile filtered through a 0.2 µm filter and 10 mL of HI-FBS was added per 500 mL of media.

Infectious material—Frozen Infected Virus Cell Preparation:

Two vials of RSV (strain Long) containing 1×10$^7$ pfu/mL was thawed using an Eppendorf thermomixer for 13 min at 15° C., with shaking at 350 rpm. Two mL of the virus stock was added to a T-225 flask containing 3.0×10$^8$ HEp-2 cells in 30 mL Complete DMEM/F12®. The cells were incubated for 18-20 h at 37° C., 5% $CO_2$, 90% relative humidity. The medium was aspirated and the cells washed with 10 mL PBS without $Mg^{2+}$ or $Ca^{2+}$. Cells were harvested from flasks using 0.25% trypsin-EDTA. The cells were resuspended in a freezing medium of 95% fetal calf serum and 5% DMSO to a final cell density of 2×10$^6$ cells/mL. One mL aliquots of this virus infected cell suspension were dispensed to cryovials and cells were rate frozen to −80° C. Frozen infected cells were then transferred to −150° C. for long term storage.

Single Dose Compound Preparation:

For single dose screening, compounds or carrier control (DMSO) were diluted to 6× in Complete DMEM/F12® and 5 µl was dispensed to assay plates (3% DMSO or 60 µM compound in 3% DMSO).

Control Drug:

The positive control drug for this assay, ribavirin [1] (#196066, MP Biomedicals, Solon, Ohio) was solubilized in DMSO. It was diluted and added to the assay plates as described for test compounds. Final concentration for ribavirin was 35 µM. All wells contained 0.5% DMSO.

Preparation of HEp-2 Cells:

Cells were harvested and resuspended to 80,000 cells/ml in complete DMEM/F12®.

Frozen Infected HEp-2 Cells:

Cells were thawed in a room temperature water bath with gentle agitation. The tube was inverted 5-10 times. Cells were diluted to 80,000 cells/ml by adding the contents of the vial to 24 ml of cold (4° C.) media.

Primary Assay Set up:

Twenty five µl of uninfected HEp-2 cells were plated in the cell control wells. Frozen infected cells were combined with uninfected HEp-2 cells at a 1:100 ratio. Twenty five µl of the cell mixture was added to the virus control and compound wells. All cell plating was conducted using a Matrix WellMate™ and cells were maintained at room temperature with stirring during the plating process. The assay plates were incubated for six days at 37° C., 5% $CO_2$ and 90% relative humidity.

Endpoint Read:

Following the six day incubation period, the assay plates were equilibrated to room temperature for 30 min and an equal volume (30 µL) of Cell Titer-Glo® reagent (Promega Inc.) was added to each well using a WellMate™ (Matrix, Hudson, N.H.) and plates were incubated for an additional 10 min at room temperature. At the end of the incubation, luminescence was measured using a Perkin Elmer Envision™ multi-label reader (PerkinElmer, Wellesley, Mass.) with an integration time of 0.1 s.

2. Compound Screening Using CPE-Based Virus Based Assay for Evaluation of RSV Inhibitors The assay is sensitive and robust, with Z values >0.8, signal to background, S/B>35, and signal to noise, S/N>24. Various parameters were optimized and validated including cell density, viral concentration, DMSO tolerance for compound dilution, incubation time for virus-induced CPE and effective control drug concentration. Additional parameters, such as day to day assay variability, reagent and read stability, edge effects, and $EC_{50}$ stability were also examined during validation.

Dose Response Compound Preparation:

For dose response screening, compounds or carrier control (DMSO) were diluted to 6× in Complete DMEM/F12® and 5 µl was dispensed to assay plates (3% DMSO). Test compounds were serially diluted in a plate to plate matrix or stacked plate matrix. All 320 compounds in a source plate were diluted together resulting in a 10 point dose response dilution series. It was visualized as a serial dilution series proceeding vertically through a stack of plates with the high dose plate on top and the low dose plate on the bottom. (Final plate well concentration ranging from 50 µM to 0.097 µM and a final DMSO concentration of 0.5%).

Control Drug:

The positive control drug for this assay, ribavirin (No. 196066, MP Biomedicals, Solon, Ohio) was solubilized in DMSO. It was diluted and added to the assay plates as described for test compounds. Final concentration for ribavirin was 35 µM. All wells contained 0.5% DMSO.

Preparation of HEp-2 Cells:

Cells were harvested and resuspended to 80,000 cells per ml in Complete DMEM/F12®.

Assay Set Up:

Twenty five µl of uninfected HEp-2 cells were plated in the cell control wells. Twenty five µl of the cell mixture was added to the virus control and compound wells. All cell plating was conducted using a Matrix WellMate™ and cells were maintained at room temperature with stirring during the plating process. The assay plates were incubated for six days at 37° C., 5% $CO_2$ and 90% relative humidity.

Endpoint Read:

Following the six day incubation period, the assay plates were equilibrated to room temperature for 30 min and an equal volume (30 µL) of Cell Titer-Glo reagent (Promega Inc.) was added to each well using a WellMate™ (Matrix, Hudson, N.H.) and plates were incubated for an additional 10 min at room temperature. At the end of the incubation, luminescence was measured using a Perkin Elmer Envision™ multi-label reader (PerkinElmer, Wellesley, Mass.) with an integration time of 0.1 s.

3. Compound Screening Using an HTS Cytotoxicity Screen to Evaluate RSV Inhibitors This cell-based assay measured the cytotoxicity of compounds in cells using luminescent cell viability assay readout.

Assay Description:

The assay is sensitive and robust, with Z values >0.8, signal to background, S/B>35, and signal to noise, S/N>24. Various parameters were optimized and validated including cell density, viral concentration, DMSO tolerance for compound dilution, incubation time for virus-induced CPE and effective control drug concentration. Additional parameters, such as day to day assay variability, reagent and read stability, edge effects, and $EC_{50}$ stability were also examined during validation.

Dose Response Compound Preparation:

For dose response screening, compounds or carrier control (DMSO) were diluted to 6× in Complete DMEM/F12® and 5 µl was dispensed to assay plates (3% DMSO). Test compounds were serially diluted in a plate to plate matrix or stacked plate matrix. All 320 compounds in a source plate were diluted together resulting in a 10 point dose response dilution series. It was visualized as a serial dilution series proceeding vertically through a stack of plates with the high dose plate on top and the low dose plate on the bottom. (Final plate well concentration ranging from 50 µM to 0.097 µM and a final DMSO concentration of 0.5%).

Control Drug:

The positive control drug for this assay, ribavirin (No. 196066, MP Biomedicals, Solon, Ohio) was solubilized in DMSO. It was diluted and added to the assay plates as described for test compounds. Final concentration for ribavirin was 35 µM. All wells contained 0.5% DMSO.

Preparation of HEp-2 Cells:

Cells were harvested and resuspended to 80,000 cells per ml in Complete DMEM/F12®.

Assay Set Up:

Twenty five µl of uninfected HEp-2 cells were plated in the cell control wells. Twenty five µl of the cell mixture was added to the virus control and compound wells. All cell plating was conducted using a Matrix WellMate™ and cells were maintained at room temperature with stirring during the plating process. The assay plates were incubated for six days at 37° C., 5% $CO_2$ and 90% relative humidity.

Endpoint Read:

Following the six day incubation period, the assay plates were equilibrated to room temperature for 30 min and an equal volume (30 µL) of Cell Titer-Glo® reagent (Promega Inc.) was added to each well using a WellMate™ (Matrix, Hudson, N.H.) and plates were incubated for an additional 10 min at room temperature. At the end of the incubation, luminescence was measured using a Perkin Elmer Envision™ multi-label reader (PerkinElmer, Wellesley, Mass.) with an integration time of 0.1 s.

4. Secondary Screen of RSV Inhibitors by a Titer Reduction Assay

This assay provided an alternative measurement of inhibitory activity on virus replication. It measured reduction in progeny virus titer by treating the infected cells with testing compounds. The assay was used to confirm antiviral activities of the selected compounds.

Assay Description:

Compounds Screened: 51 compounds were selected for $TCID_{50}$ analysis based on the criteria of activity: an efficacy $EC_{50}$ value of <10 µM and with toxicity to efficacy $SI_{50}$ of >3.

Assay Set-Up:

Titer of progeny viruses produced from the cell was measured by $TCID_{50}$ assay in 384-well plate format with 4 wells per dilution of virus (MOI of 0.12). 10 µl of 10-fold serial dilutions of progeny virus containing medium from respective samples (drug treated or untreated) were transferred to infect fresh HEp-2 cells in a 384-well format. The cell plates were incubated at 37° C., 5% $CO_2$, and high humidity for an additional 6 days.

Endpoint Read:

The Cell Titer Glo® assay was used to determine viability of the cells. The assay plates were equilibrated to room temperature for 10 minutes and then an equal volume of Cell Titer-Glo® reagent (Promega Inc.) was added to each well.

Plates were incubated for 10 min at room temperature and luminescence was measured using a multi-label plate reader with an integration time of 0.1 s. A well showing luminescence signal less than mean of non-infected control signal minus 3 times of standard deviation of the control was regarded as positive for infection.

5. Secondary Screen of RSV Inhibitors by a Time of Addition CPE Assay

Time of addition assays were performed to determine the window in the RSV lifecycle that the lead compounds inhibit.

Assay Description: HEp-2 cells were plated in 96 well black tissue culture plates at 10,000 cells per well in 80 µl and incubated 24 hours at 37° C., 5% $CO_2$. All cell plating was conducted using a Matrix WellMate™ and cells were maintained at room temperature with stirring during the plating process. Compounds were diluted in media to give a final concentration of 25 µM and added to plates at −1, 0, 1, 4, 6, 20 and 24 hours post-infection (p.i.). The cells were infected with RSV Long strain at an MOI of 3 and the assay plates were incubated for six days at 37° C., 5% $CO_2$ and 90% relative humidity.

Endpoint Read:

The Cell Titer Glo® assay was used to determine viability of the cells. The assay plates were equilibrated to room temperature for 10 minutes and then an equal volume of Cell Titer-Glo reagent (Promega Inc.) was added to each well. Plates were incubated for 10 min at room temperature and luminescence was measured using a multi-label plate reader with an integration time of 0.1 s.

6. RSV Plaque Assay

A plaque assay was developed to confirm antiviral compound effect and determine the potency of compounds.

Assay Description:

HEp-2 cells were seeded in 6 well tissue culture plates at 1,000,000 cells per well in 2 mL and incubated 24 hours at 37° C., 5% $CO_2$. The media was aspirated from the wells, 0.5 mL RSV Long strain (MOI of 0.1) was added and the plates incubated at 37° C., 5% $CO_2$, rotating every 20 min. to facilitate infection. After 2 hours, the virus supernatant was aspirated and each well was washed with 3 mL of 1×PBS. Compounds were diluted in media to give a final concentration of 25 micro-molar, added to assay plates and incubated at 37° C., 5% $CO_2$ and 90% relative humidity. After 48 hours, the supernatant (RSV/compound/media; 2 mL) was removed and frozen at −80° C.

HEp-2 cells were seeded in 24 well tissue culture plates at 400,000 cells per well in 0.5 mL and incubated 24 hours at 37° C., 5% $CO_2$. The supernatant (RSV/compound/media) was removed from −80° C. and thawed on ice. The supernatants were serially diluted in media (1E-00 to 1E-04). The media was aspirated from the 24 well plates, 0.2 mL of each dilution was added to each well and the plates incubated at 37° C., 5% $CO_2$, rotating every 20 min. to facilitate infection. After 2 hours, the virus supernatant was aspirated and each well was washed with 1 mL of 1×PBS followed by the addition of 0.5 mL 1% Avicel per well. The assay plates were incubated for six days at 37° C., 5% $CO_2$ and 90% relative humidity.

Endpoint Read:

Following the six day incubation period, the Avicel overlay was aspirated, 0.5 mL of 4% paraformaldehyde was added per well and the assay plates incubated at 4° C. After 24 hours, the wells were washed with tap water and 1 mL of 0.05% neutral red was added per well. The assay plates were stained for 4 hours at room temperature, the neutral red removed, washed with tap water and plates dried with lids off.

7. Solubility Studies

Solubility was measured in phosphate buffered saline (PBS) at room temperature (23° C.). PBS by definition is 137 mM NaCl, 2.7 mM KCl, 10 mM sodium phosphate dibasic, 2 mM potassium phosphate monobasic and a pH of 7.4 Compound A was found to have a solubility measurement of 0.18 µg/mL, or 0.36 µM, under these conditions. Solubility was also assessed in RSV CPE assay media (DMEM/F12(r) (Sigma, Cat #D6434)/1× Pen/Strep/Glutamine (Gibco, Cat #10378)/2% Heat Inactivated FBS (Gibco Cat #10082)). Compound A was determined to have an assay media solubility of 5.1 µg/mL, or 10.21 µM. The solubility in PBS buffer was limited; however, in assay media, the compound concentration was determined to be >12-fold higher than that of the measured CPE assay $EC_{50}$. The presence of fetal bovine serum in the media likely accounts for the observed solubility, though the degree of protein binding was not assessed independently.

8. Stability Studies

Stability was measured under two distinct conditions with Compound A. Stability, depicted as closed circles FIG. 1, was assessed at room temperature (23° C.) in PBS (no antioxidants or other protectants and DMSO concentration below 0.1%). Stability, illustrated with closed squares in the graph, was also assessed with 50% acetonitrile added as the solubility of the compound in PBS was 0.18 µg/mL. Stability data in each case is depicted as a graph showing the loss of compound with time over a 48 hr period with a minimum of 6 time points and providing the percent remaining compound at the end of the 48 hr. With no additives (closed circles), 27% of Compound A remains after 48 hours; however, this data is dependent on and misleading due to the solubility limitations in PBS buffer. With the addition of 50% acetonitrile to account for solubility (closed squares), 100% of Compound A remained after 48 hours.

9. Results and Discussion

An initial quinazolinedione compound of interest was identified in the initial high-throughput screen (4-((1-(4-methylbenzyl)-2,4-dioxo-1,2-dihydroquinazolin-3(4H)-yl) methyl)-N-(3-methoxypropyl)benzamide) was determined to have an averaged $EC_{50}$=2.14 µM and a $CC_{50}$ of 59.50 µM, thus possessing a SI of ~28. The compound demonstrated in vitro log reduction of viral plaques of 4.15. Solubility in PBS buffer was 0.13 µM, and as such, aqueous solubility was also a focus of optimization efforts. 71 compounds have been synthesized, and all analogs were purified and analyzed prior to assay. The SAR strategy focused on four regions of the scaffold for targeted enhancement of potency, cytotoxicity, reduction of viral plaques and improved solubility.

Analogs bearing a substituent at the core C6 or C7 position were prepared ($R_1$ and $R_2$ in the left structure below), however, all compounds in this subset were inactive. Elongation of the methylene spacer between the quinazolindione core and the benzamide moiety by one additional methylene unit or moving the amide on the phenyl ring to the meta-position was also not beneficial (right structure below).

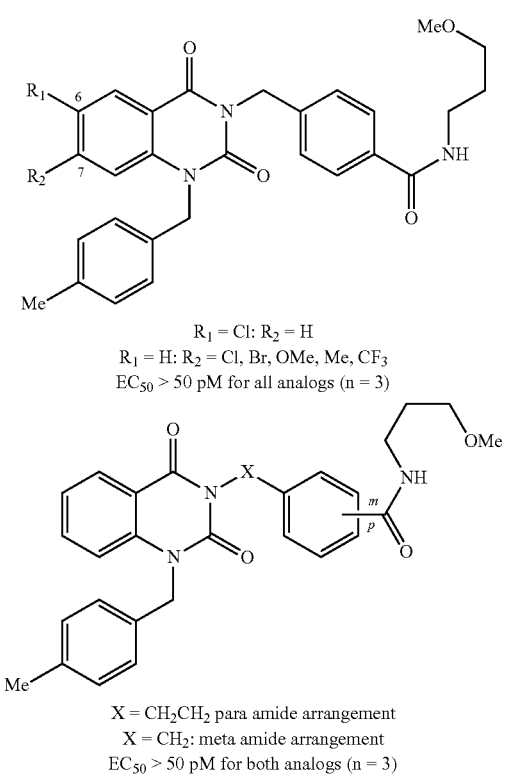

$R_1$ = Cl: $R_2$ = H
$R_1$ = H: $R_2$ = Cl, Br, OMe, Me, $CF_3$
$EC_{50}$ > 50 μM for all analogs (n = 3)

X = $CH_2CH_2$ para amide arrangement
X = $CH_2$: meta amide arrangement
$EC_{50}$ > 50 μM for both analogs (n = 3)

Tolerance was found when modifying the 4-methylbenzyl appendage (FIG. 3). The hit compound was tested as two different batches (FIG. 3, entries 1-2, average $EC_{50}$=2.14 μM; $CC_{50}$=59.50 μM; SI of ~28). Installation of non-aromatic, alkyl substituents resulted in complete loss of potency (FIG. 3, entries 3-5, $EC_{50}$>50 μM). Removal of the 4-methyl group from the phenyl substituent or elongation of the methylene linker was also found to be unacceptable (FIG. 3, entries 6-9). Generally, substitution of the phenyl ring in the 4-position was preferred, as 3-substituted phenyl derivatives lost potency, and 2-substituted phenyl analogs were inactive. Increasing steric bulk at the four phenyl position (methyl→ethyl→isopropyl) resulted in improved potency and selectivity index (FIG. 3, entries 1→21→22, where 22 is Compound A). Electron withdrawing groups in this same position were advantageous, and those that mimicked the steric character of small branched aliphatic groups, like a nitro group, were most promising (FIG. 3, entries 17 and 18, Compound B, two different batches of the same compound, averaged $EC_{50}$=0.57±0.014 μM; $CC_{50}$=128±4.24 μM). A 4-nitrile replacement of the 4-nitro group did not afford a compound with a competitive profile (FIG. 3, entry 20).

In parallel, alterations of the substituted secondary amide were surveyed (FIG. 4). The hit compound is included for reference (two batches, FIG. 4 entries 1-2, average $EC_{50}$=2.14 μM; $CC_{50}$=59.50 μM; SI of ~28). Exchange of the methyl ether for ethyl or isopropyl ether did not appreciably alter the potency; however, the cytotoxicity effects associated with those analogs increased relative to the parent (FIG. 4, entries 3-4). A tertiary amine installed in place of the ether for the purpose of enhancing solubility was not tolerated in terms of potency or toxicity (FIG. 4, entry 5). While elongation of the alkyl chain by one methylene unit enhanced potency but with a narrower therapeutic window (FIG. 4, entry 6), shortening the chain by one methylene unit produced an analog with a comparable profile to the hit compound (FIG. 4, entry 7). Using an oxetane as a cyclized version of the alkyl ether chain (FIG. 4, entry 8) produced a promising profile in which the potency was in the 700 nM range, the SI was 66 and a 5.1 log reduction in viral plaques was determined. Other modifications were explored that attempted to improve solubility or potency without effecting toxicity, but none of these offered an improved profile compared to the hit.

What was learned from modulating the individual components (summarized in FIG. 3 and FIG. 4) was used to generate hybrid analogs, and SAR and around those features was further developed (FIG. 5). At this stage, several compounds were assessed for improvement in solubility as well. Our survey of R1 groups (FIG. 3) indicated that the 4-nitrophenylmethylene and 4-i-propylphenylmethylene moieties afforded the most promising analogs in terms of potency, cytotoxicity, and plaque reduction. Work on the R2 component (FIG. 4) revealed that the use of $NHCH_2$-3-oxetane was also beneficial. When the 4-nitrophenylmethylene functionality was paired with the $NHCH_2$-3-oxetane, low micromolar potency was achieved with satisfactory selectivity; however, the compound's profile was not competitive with others that had been prepared (FIG. 5, entry 3, $EC_{50}$=1.32 μM, SI~38). Using a carboxylic acid as an isostere for the nitro group afforded a compound with much improved aqueous solubility, but rendered the compound inactive (FIG. 5, entry 4). Pairing the 4-i-propylphenylmethylene unit with the $NHCH_2$-3-oxetane enhanced potency, but also substantially reduced the selectivity index (FIG. 5, entry 5, $EC_{50}$=400 nM, SI=9).

A dimethylamine substituent was investigated as a possible steric replacement for the isopropyl or nitro group with the added feature of incorporating a solubilizing group (FIG. 5, entry 7). The aqueous solubility was greatly improved without obliterating activity. Potency was retained in the low micromolar range, the cytotoxicity effect was near 50 μM, and the compound pegged the plaque reduction assay at a maximal level of a log reduction >6. Although a furyl group is considered a metabolic liability, the functionality was used to elucidate the effect of maintaining an ether-like moiety while introducing conformational restraint which is lacking in the alkyl ether linkage. The furyl analog (FIG. 5, entry 8) with a 4-chlorophenylmethylene group at $R_1$ afforded good potency and cytotoxicity values and showed good solubility in media.

PBS solubility of Compound A was limited, and therefore, the stability studies conducted in PBS were skewed due to precipitation of the compound out of solution over a 48 hour window; however, the addition of 50% acetonitrile to compensate for solubility in PBS reflected no issues with structural stability in aqueous media.

Figure 2:
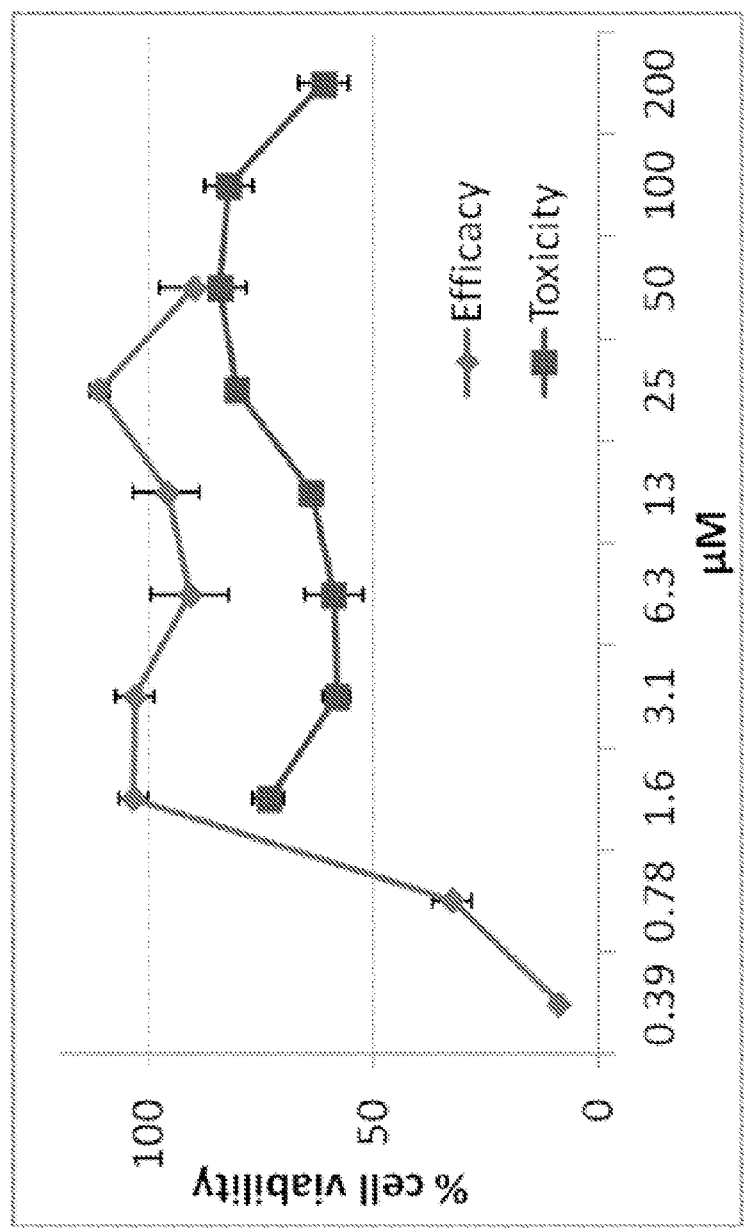
FIG. 2 is a graph of the dose response efficacy (diamonds) and cytotoxicity (squares) profile for Compound A.

The primary assay methodology was used to measure both efficacy and cytotoxicity. Compound A potency in the RSV CPE assay was determined: $EC_{50}$=0.81±0.75 μM, and the $CC_{50}$>200 μM. The calculated selectivity was determined as ($CC_{50}/EC_{50}$)>247. The Compound A dose response profiles for efficacy and cytotoxicity curves are presented in FIG. 2.

The RSV CPE assay was repeated for Compounds A and B, and provided values of 0.34 μM and 0.20 μM respectively.

Data for Compounds A-F are further summarized in the specification at Table 2.

Several compounds met the desired probe criteria for a post-entry inhibitor and possessed additional attributes considered advantageous. For compounds that met these defined criteria, two compounds were assessed for liabilities that might limit them in this capacity (FIG. 15). Hepatocyte toxicity was not an issue for either ($LC_{50}$>30 µM or >50 µM, for Compounds A and B, respectively).

Example 3

Profiling Assays

Antiviral Selectivity and Tested Cell Types:
The compounds were tested in two different human cell types. The primary assay was performed in HEp2 cells and the secondary assays were performed in HEp2 and A549 cells. Compounds were effective against RSV in both cell lines. Compound A was also tested for activity against vaccinia, influenza A, Venezuelan equine encephalitis, and dengue viruses. Compound A showed no efficacy in inhibiting these viruses, thus showing selectivity for RSV.

Broad Spectrum Target Profiling:
Compound A was submitted for assessing off-target pharmacology using a Ricerca LeadProfiling® screen made up of 67 assays. Compound A was assayed in duplicate at a concentration of 10 µM for all targets, and the responses illustrated in Table 3 were noted as ≥50% inhibition or stimulation for biochemical assays:

TABLE 3

Targets against which ML275 demonstrated >50% inhibition

| Target | Species | Percent Inhibition |
| --- | --- | --- |
| Calcium Channel L-Type, Benzothiazepine | rat | 52 |
| Calcium Channel L-Type, Dihydropyridine | rat | 70 |
| Cannabinoid CB1 | human | 86 |
| Serotonin (5-Hydroxytryptamine) 5-$HT_{2B}$ | human | 54 |
| Transporter, Norepinephrine (NET) | human | 54 |

Inhibition for the human adenosine $A_3$ receptor and human platelet activating factor was noted at 44% and 43%, respectively; however, all other inhibition levels were reported below 34 percent.

Example 4

Mechanism of Action Studies

Figure 6:
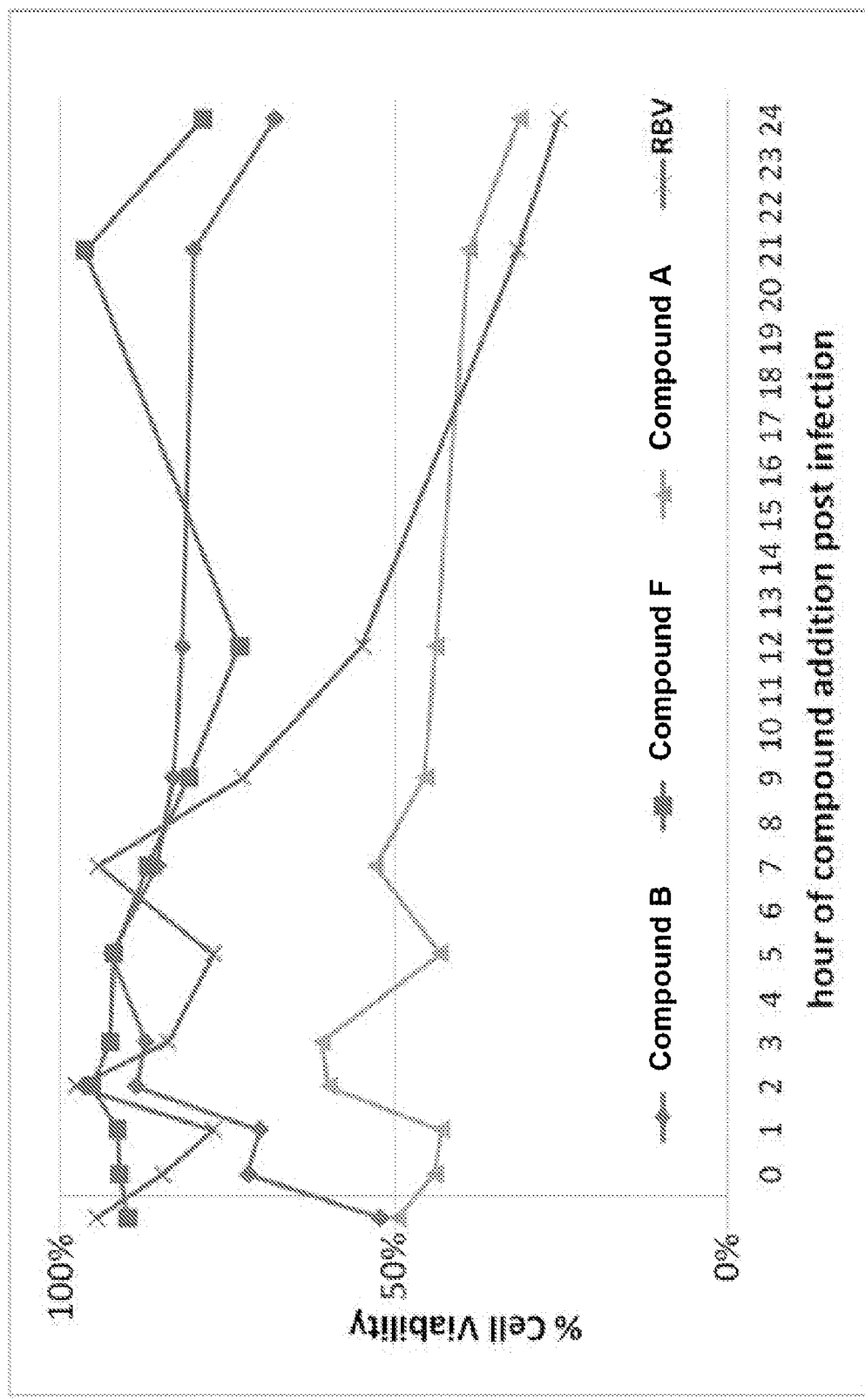
FIG. 6 is a graph of time-of-addition assay results for selected compounds.

A cell-based assay was used to determine the ability of the probe to inhibit different stages of a single round of viral replication. A known amount of RSV virus was added to the cells, and Compound A was added at −1, 0, 1, 2, 3, 5, 7, 9, 12, 21, and 24 hours post-infection. Compound-mediated inhibition of viral replication at each time point indicated that the latest effective time of addition was at the late stage of the viral life cycle, >24 hours post-infection. The graph in FIG. 6 shows the ability of Compound A (at 10 µM) to sustain cell viability during RSV infection when added at the indicated time points. Compound A is shown as triangles. Compounds B and F (diamonds and squares, respectively) are of similar chemical structure. The percent cell viability values at each time point for the respective molecules are compared with that of ribavirin (RBV). The interpretation of the data is as follows: Ribavirin treatment protected cells from CPE (approximately 100%) induced by RSV for up to 7 hours post-infection indicating that it targets the period of infection during which viral replication is in progress. This is consistent with the mode of action of ribavirin, i.e., inhibition of the cellular IMP dehydrogenase (IMPDH) resulting in depletion of the intracellular GTP pool. However, addition of Compounds A, B and F at time points between 7-24 hours post-infection does not result in a dramatic change in cell viability within this window, suggesting that these compounds act at a later stage (post-genomic replication) of the viral life cycle. This sustained efficacy may be due to the inhibition of one or more late virus life cycle steps (post-entry or late-stage infection processes), and this hypothesis is supported by an ability to affect processes later in the viral replication cycle. This indicates that the probe may be a post entry inhibitor which inhibits late infection events (characterized by viral transport, viral assembly and viral budding).

Example 5

Titer Reduction Measurements by Plaque Assay

Representative compounds with an $EC_{50}$<1.5 µM and a selectivity index >10 were further evaluated for their ability to reduce the amount of infectious virus produced in cell culture. These measurements of compound-mediated viral titer reduction were used to complement the cytoprotection assay results. A standard plaque-reduction assay was used as a secondary assay to determine the ability of the probe class compounds to reduce the amount of infectious virus produced in HEp-2 cells. HEp-2 cells were infected with RSV in the presence of 10 µM test compound. Media supernatants were removed and 10-fold serial-diluted onto a confluent field of uninfected, untreated HEp-2 cells, bound, washed, and overlaid with semi-solid media to limit the spread of infectious virus in the cell field. After a set period of time, plaques resulting from the spreading viral infection of the cell field were fixed, stained, and counted to determine the amount of infectious virus in the original, drugged supernatants. In Table 4 below, the compounds that fit the criteria are listed, along with the log reduction in viral titer produced by the compound. A clear SAR trend between the CPE assay potency and degree of plaque reduction was not obvious.

TABLE 4

Log reduction in virus titer in the presence of 10 µM test compound.

| Compound | CPE $EC_{50}$ µM | Selectivity Index ($CC_{50}/EC_{50}$) | Plaque Reduction Assay (log reduction) at 10 µM |
| --- | --- | --- | --- |
| FIG. 5, #5 | 0.40 ± 0.010 | 9.0 | 5.75 |
| Compound B | 0.57 ± 0.014 | >224.0 | >5.56 |
| FIG. 4, #15 | 0.70 ± 0.030 | 12.1 | 5.54 |
| Compound F | 0.71 ± 0.13 | 41.8 | 5.10 |
| Compound A | 0.81 ± 0.75 | >247 | 6.70 |
| FIG. 4, #6 | 0.83 ± 0.050 | 7.8 | 2.10 |
| Compound C | 0.85 ± 0.15 | 118.9 | 4.07 |
| FIG. 4, #9 | 0.96 ± 0.080 | 7.89 | 1.20 |
| Compound D | 1.00 ± 0.05 | 94.5 | 5.90 |
| FIG. 4, #22 | 1.04 ± 0.040 | 48.2 | 3.50 |
| Compound E | 1.07 ± 0.22 | 41.8 | >6.18 |
| FIG. 5, #9 | 1.23 ± 0.11 | 122.0 | 2.83 |
| FIG. 3, #19 | 1.32 ± 0.060 | 103.7 | 2.66 |
| FIG. 5, #3 | 1.32 ± 0.05 | 37.9 | >6.18 |
| FIG. 3, #25 | 1.49 ± 0.91 | 79.6 | 2.37 |

Example 6

| Name | EC$_{50}$ µM | CC$_{50}$ µM | Selectivity Index (CC$_{50}$/EC$_{50}$) | Plaque log reduction at 10 µM | MOA | Known Toxicity |
|---|---|---|---|---|---|---|
| | | Comparison of Ribavirin to Compound A | | | | |
| Compound A | 0.81 ± 0.75 | >200 | >247 | 6.70 | post-entry inhibitor | unknown |
| ribavirin | 28.37 ± 3.75 | 113.9 ± 38.52 | 3.60 | 2.47 | post-entry inhibitor | hemolytic anemia |

Compared to ribavirin, Compound A has an improved CPE EC$_{50}$ of 0.81 µM and selective index of >247 (ribavirin: 28.37 µM and 3.6, respectively). Compound A was shown to reduce viral replication in a cell-based assay by 6.7 log, intervenes at a different stage in the viral life cycle than ribavirin, and has strong potential for therapeutic use instead of as a prophylactic agent. Therefore, Compound A represents an improvement both in its therapeutic index and potential.

Example 7

Pharmacokinetic Experiments

Six cotton rats, 5 to 15 weeks of age, will be given a single-bolus dose of 10 mg/kg and six cotton rats a dose of 50 mg/kg compound intravenously (i.v.). The compound will be dissolved in an aqueous 10% 2-hydroxypropyl-cyclodextrin solution at pH 4. An additional group of six, non-treated control rats will be included. Blood samples will be taken from the orbital venous plexus of all groups of cotton rats at 15 min, 1, 4, 8, and 24 h post-dose. Blood samples will be centrifuged at 1,500×g for 10 min, and plasma separated and frozen until bioanalysis. After blood sampling, the rats will be exsanguinated from the vena femoralis under isoflurane-oxygen anesthesia and euthanized by CO$_2$ asphyxiation.

Pharmacokinetic Data Analyses:

Blood concentrations of compound as determined by LCMS will be analyzed along with sample times and dose information to determine PK parameters. Concentration-time data will be plotted and the following parameters estimated for each treated animal: (AUG) Area under concentration-time curve (AUC) will be determined by the trapezoidal method. If elimination is incomplete by the time of last data sample, AUC values will be adjusted by addition of estimated additional area to time infinity using the ratio, last concentration/ke, to complete the AUC estimates. Half-life (T ½) will be determined from slopes of log-linear terminal time data. The rate constant (ke) of compound elimination will be determined from the slope of natural log concentration vs. time plots.

Systemic clearance (Cl) will be calculated from the ratio of Dose/AUC for each animal. Volume of distribution (Vd) will be determined from the ratio of Cl/ke. Bioavailability (F) of oral dose will be determined for each dose level using mean AUC values; the ratio, oral AUC/intravenous AUC, will provide this measure of the percent of an oral dose that reaches systemic circulation. Bioavailability values will be compared across doses to determine if there is dose dependence.

Example 8

Pharmacokinetic-Pharmacodynamic Experiments

Five cohorts of six cotton rats will be given an aqueous suspension of compound in a single subcutaneous (s.c.) dose of 12.5, 25, 50, 100, or 200 mg/kg. An additional group of six, non-treated control rats will be included. Blood samples will be obtained from the orbital venous plexus 24 h after the administration of compound and centrifuged at 1,500×g for 10 min. Plasma will be separated and frozen until bioanalysis Immediately after blood collection, rats will be anesthetized with isoflurane and inoculated dropwise by the intranasal route with 10$^6$ PFU of RSV in 0.1 ml cell culture medium. The virus will be administered intranasally because this is an effective and minimally invasive route of administration (Table 5). On Day 4 rats will be euthanized via isoflurane/Co, asphyxiation. The lungs of the animals will be intubated and flushed once with 2.5 ml PBS, and the BALF centrifuged at 300×g for 10 min. The resulting supernatant will be titrated immediately for RSV infectivity by plaque assays. In addition, nasal turbinates, spleens, and blood samples will be collected for viral and immunological endpoints. Animals will be observed for clinical signs throughout the study period. All observations will be recorded with particular attention paid to signs of dyspnea, nasal and ocular discharge, weight loss, temperature, neurological signs, lethargy, and other abnormalities. We will also collect samples from rats that become moribund, when weight loss equals or exceeds 25%, or when body temperature is less than 93.2° F. One sample of each lung will be weighed, placed in individually labeled cryovials, and immediately snap-frozen in liquid nitrogen subsequent analyses viral and immunological endpoints. Lungs, nasal swabs, pharyngeal swabs, rectal swabs from infected animals will be taken and viral titers measured. Lungs will be homogenized in PBS and analyzed for the presence of infectious virus particles by plaque assay. We have also developed standard operating procedures for the determination of the tissue culture infectious dose at which 50% of the cells are infected (TCID$_{50}$). This TCID$_{50}$ assay has been compared to the agarose overlay plaque assay to determine the variation between those two assays with comparable results.

TABLE 5

General strategy to test compound
efficacy against RSV in cotton rats

| Dose Group | Drug Administered | Drug Dose Level (mg/kg/day) | Virus Challenge Volume (μL/dose) 100 μL/10⁶ PFU | Sacrifice Day 4 n = 6/group |
|---|---|---|---|---|
| 1 | Vehicle | 0 | 100 | 6 |
| 2 | compound | 12.5 | 100 | 6 |
| 3 | compound | 25 | 100 | 6 |
| 4 | compound | 50 | 100 | 6 |
| 5 | compound | 100 | 100 | 6 |
| 6 | compound | 200 | 100 | 6 |

Example 9

Pharmacokinetic-Pharmacodynamic Experiments

Compounds with structures similar to Compound A will be tested for suitability as internal standards for the assay. Rat plasma samples will be spiked with internal standard and then protein in the plasma will be precipitated with acetonitrile (ACN). Supernatant will be collected after centrifugation and dried by speedvac. Residue will be dissolved in 5% ACN/0.1% formic acid, filtered through filter, and then analyzed by Accela LC System (Thermo Scientific, San Jose, Calif.) coupled to a LTQ Orbitrap XL mass spectrometer (Thermo Scientific, San Jose, Calif.). Samples will be loaded onto a 50×2.1 mm×1.9 urn Hypersil GOLD column (Thermo Scientific, San Jose, Calif.) and eluted with binary solvent gradient (Solvent A: 55% ACN/0.1% formic acid and Solvent B: 95% ACN/0.1% formic acid) at 100 μL/min. Elutes from LC column will be ionized by electrospray ionization and Compound A and internal standard will be detected by multiple reaction monitoring. Full scan fragment spectra from precursor ions (molecular ions of Compound A and internal standard) will be acquired by Orbitrap. Compound confirmation will be obtained from fragment spectra and concentration will be calculated from peak areas of fragment ion chromatograms specific to Compound A and internal standard. A calibration curve will be prepared from control rat plasma spiked with authentic Compound A and internal standard.

Example 10

Pharmacokinetic-Pharmacodynamic Experiments

A maximum tolerated dose (MTD) was determined for Compound B using cotton rats not infected with virus. The basic premise for defining range is to extrapolate from the known in vitro data for the candidate drug and administer various concentrations of drug to determine the effects of treatment.

Six cotton rats were dosed intraperitoneally twice daily to a final 125 mg/kg and showed no overt toxicity by animal wellness or gross pathology as compared to six control animals with vehicle alone.

TABLE 6

Maximum Tolerated Dose Results

| Group | No. of animals | Drug given (i.p.) | Drug dose (mg/kg) | Drug dose volume (μL/dose) | No. of doses per day | Euthanasia on moribund or day |
|---|---|---|---|---|---|---|
| 1 | 6 | Vehicle only (1% methyl carboxy-cellulose) | 0 | 200 μL | 2 | 4 |
| 2 | 6 | Compound B | 125 | 200 μL | 2 | 4 |
| TOTAL | 12 | | | | | |

The invention claimed is:

1. A method of treating a respiratory syncytial virus infection in a subject in need of treatment, comprising administering to the subject a therapeutically effective amount of a compound of formula (I):

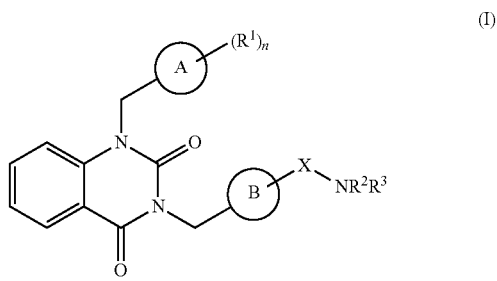

wherein:
A and B are each independently aryl, heteroaryl, cycloalkyl or heterocycle;
n is 0, 1, 2, 3, 4 or 5;
$R^1$ is selected from the group consisting of alkyl, halo, nitro, cyano, haloalkyl, amino, alkoxy, —$SO_2H$, —$SO_2NHR'$, $CONHR'$, aryl, heteroaryl, cycloalkyl and heterocycle;
each R' is independently selected from the group consisting of hydrogen and alkyl;
X is a bond, —C(O)—, $CH_2$ and $SO_2$;
$R^2$ and $R^3$ are independently selected from the group consisting of hydrogen, alkyl, aryl, heteroaryl, cycloalkyl, heterocycle, haloalkyl, arylalkyl, heteroarylalkyl, cycloalkylalkyl, heterocycloalkyl, alkoxyalkyl and aminoalkyl, or $R^2$ and $R^3$ are taken together with the atom to which they are attached to form a heterocyclic ring;
each aryl is independently selected from the group consisting of phenyl, naphthyl and anthracenyl;
each heteroaryl is independently an aromatic 5-8 membered monocyclic ring having 1-3 heteroatoms, an 8-12 membered bicyclic ring having 1-6 heteroatoms, or an aromatic 11-14 membered tricyclic ring system having 1-9 heteroatoms, said heteroatoms each independently selected from the group consisting of O, N, S, P and Si;
each cycloalkyl is independently a non-aromatic, saturated or partially unsaturated cyclic, bicyclic or tricyclic hydrocarbon group having 3 to 12 carbon atoms; and
each heterocycle is independently: a nonaromatic, saturated or partially unsaturated 3-10 membered monocyclic ring system having 1-3 heteroatoms; a nonaromatic, saturated or partially unsaturated 8-12 membered bicyclic ring system having 1-6 heteroatoms; or a nonaromatic, saturated or partially unsaturated tricyclic ring system having 1-9 heteroatoms; said heteroatoms each independently selected from the group consisting of O, N, S, P and Si.

2. The method of claim 1, wherein A is phenyl.

3. The method of claim 1, wherein n is 1.

4. The method of claim 1, wherein $R^1$ is selected from the group consisting of $C_1$-$C_4$ alkyl, halo, amino and nitro.

5. The method of claim 4, wherein $R^1$ is selected from the group consisting of methyl, ethyl, isopropyl, bromo, nitro and dimethylamino.

6. The method of claim 1, wherein B is phenyl.

7. The method of claim 1, wherein X is —C(O)—.

8. The method of claim 1, wherein one of $R^2$ and $R^3$ is hydrogen, and the other is independently selected from the group consisting of heterocycloalkyl and alkoxyalkyl.

9. The method of claim 8, wherein one of $R^2$ and $R^3$ is hydrogen, and the other is independently selected from the group consisting of 3-methoxypropyl and oxetan-3-ylmethyl.

10. The method of claim 1, wherein the compound of formula (I) is selected from the group consisting of:
    4-((1-(4-isopropylbenzyl)-2,4-dioxo-1,2-dihydroquinazolin-3(4H)-yl)methyl)-N-(3-methoxypropyl)benzamide;
    N-(3-methoxypropyl)-4-((1-(4-nitrobenzyl)-2,4-dioxo-1,2-dihydroquinazolin-3(4H)-yl)methyl)benzamide;
    4-((1-(4-bromobenzyl)-2,4-dioxo-1,2-dihydroquinazolin-3(4H)-yl)methyl)-N-(3-methoxypropyl)benzamide;
    4-((1-(4-ethylbenzyl)-2,4-dioxo-1,2-dihydroquinazolin-3(4H)-yl)methyl)-N-(3-methoxypropyl)benzamide;
    4-((1-(4-methylbenzyl)-2,4-dioxo-1,2-dihydroquinazolin-3(4H)-yl)methyl)-N-(oxetan-3-ylmethyl)benzamide; and
    4-((1-(4-(dimethylamino)benzyl)-2,4-dioxo-1,2-dihydroquinazolin-3(4H)-yl)methyl)-N-(oxetan-3-ylmethyl)benzamide.

11. The method of claim 1, wherein the subject is a human.

12. A method of inhibiting replication of respiratory syncytial virus in a sample, comprising contacting the sample with an effective amount of a compound of formula (I):

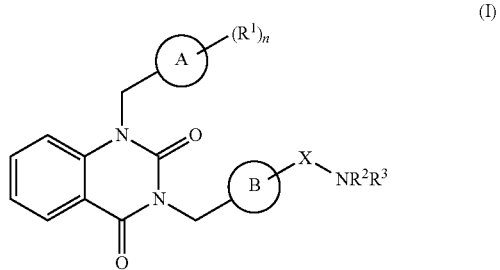

wherein:
A and B are each independently aryl, heteroaryl, cycloalkyl or heterocycle;
n is 0, 1, 2, 3, 4 or 5;
$R^1$ is selected from the group consisting of alkyl, halo, nitro, cyano, haloalkyl, amino, alkoxy, —$SO_2H$, —$SO_2NHR'$, CONHR', aryl, heteroaryl, cycloalkyl and heterocycle;

each R' is independently selected from the group consisting of hydrogen and alkyl;
X is a bond, —C(O)—, $CH_2$ and $SO_2$;
$R^2$ and $R^3$ are independently selected from the group consisting of hydrogen, alkyl, aryl, heteroaryl, cycloalkyl, heterocycle, haloalkyl, arylalkyl, heteroarylalkyl, cycloalkylalkyl, heterocycloalkyl, alkoxyalkyl and aminoalkyl, or $R^2$ and $R^3$ are taken together with the atom to which they are attached to form a heterocyclic ring;
each aryl is independently selected from the group consisting of phenyl, naphthyl and anthracenyl;
each heteroaryl is independently an aromatic 5-8 membered monocyclic ring having 1-3 heteroatoms, an 8-12 membered bicyclic ring having 1-6 heteroatoms, or an aromatic 11-14 membered tricyclic ring system having 1-9 heteroatoms, said heteroatoms each independently selected from the group consisting of O, N, S, P and Si;
each cycloalkyl is independently a non-aromatic, saturated or partially unsaturated cyclic, bicyclic or tricyclic hydrocarbon group having 3 to 12 carbon atoms; and
each heterocycle is independently: a nonaromatic, saturated or partially unsaturated 3-10 membered monocyclic ring system having 1-3 heteroatoms; a nonaromatic, saturated or partially unsaturated 8-12 membered bicyclic ring system having 1-6 heteroatoms; or a nonaromatic, saturated or partially unsaturated tricyclic ring system having 1-9 heteroatoms; said heteroatoms each independently selected from the group consisting of O, N, S, P and Si.

13. The method of claim 12, wherein A is phenyl.

14. The method of claim 12, wherein n is 1.

15. The method of claim 12, wherein $R^1$ is selected from the group consisting of $C_1$-$C_4$ alkyl, halo, amino and nitro.

16. The method of claim 15, wherein $R^1$ is selected from the group consisting of methyl, ethyl, isopropyl, bromo, nitro and dimethylamino.

17. The method of claim 12, wherein B is phenyl.

18. The method of claim 12, wherein X is —C(O)—.

19. The method of claim 12, wherein one of $R^2$ and $R^3$ is hydrogen, and the other is independently selected from the group consisting of heterocycloalkyl and alkoxyalkyl.

20. The method of claim 19, wherein one of $R^2$ and $R^3$ is hydrogen, and the other is independently selected from the group consisting of 3-methoxypropyl and oxetan-3-ylmethyl.

21. The method of claim 12, wherein the compound of formula (I) is selected from the group consisting of:
    4-((1-(4-isopropylbenzyl)-2,4-dioxo-1,2-dihydroquinazolin-3(4H)-yl)methyl)-N-(3-methoxypropyl)benzamide;
    N-(3-methoxypropyl)-4-((1-(4-nitrobenzyl)-2,4-dioxo-1,2-dihydroquinazolin-3(4H)-yl)methyl)benzamide;
    4-((1-(4-bromobenzyl)-2,4-dioxo-1,2-dihydroquinazolin-3(4H)-yl)methyl)-N-(3-methoxypropyl)benzamide;
    4-((1-(4-ethylbenzyl)-2,4-dioxo-1,2-dihydroquinazolin-3(4H)-yl)methyl)-N-(3-methoxypropyl)benzamide;
    4-((1-(4-methylbenzyl)-2,4-dioxo-1,2-dihydroquinazolin-3(4H)-yl)methyl)-N-(oxetan-3-ylmethyl)benzamide; and
    4-((1-(4-(dimethylamino)benzyl)-2,4-dioxo-1,2-dihydroquinazolin-3(4H)-yl)methyl)-N-(oxetan-3-ylmethyl) benzamide.

22. The method of claim 12, comprising contacting the sample in vitro, ex vivo, or in vivo.

23. A pharmaceutical composition comprising a compound of formula (I) and a pharmaceutically acceptable carrier:

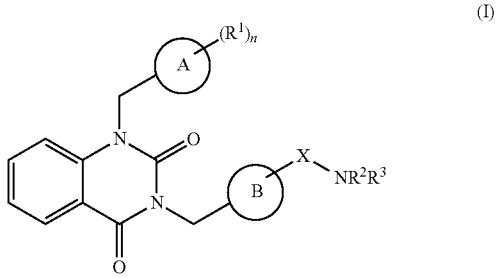

wherein:
A and B are each independently aryl, heteroaryl, cycloalkyl or heterocycle;
n is 0, 1, 2, 3, 4 or 5;
$R^1$ is selected from the group consisting of alkyl, halo, nitro, cyano, haloalkyl, amino, alkoxy, —$SO_2H$, —$SO_2NHR'$, $CONHR'$, aryl, heteroaryl, cycloalkyl and heterocycle;
each R' is independently selected from the group consisting of hydrogen and alkyl;
X is a bond, —C(O)—, $CH_2$ and $SO_2$;
$R^2$ and $R^3$ are independently selected from the group consisting of hydrogen, alkyl, haloalkyl, heterocycloalkyl, alkoxyalkyl and aminoalkyl, or $R^2$ and $R^3$ are taken together with the atom to which they are attached to form a heterocyclic ring;
each aryl is independently selected from the group consisting of phenyl, naphthyl and anthracenyl;
each heteroaryl is independently an aromatic 5-8 membered monocyclic ring having 1-3 heteroatoms, an 8-12 membered bicyclic ring having 1-6 heteroatoms, or an aromatic 11-14 membered tricyclic ring system having 1-9 heteroatoms, said heteroatoms each independently selected from the group consisting of O, N, S, P and Si;
each cycloalkyl is independently a non-aromatic, saturated or partially unsaturated cyclic, bicyclic or tricyclic hydrocarbon group having 3 to 12 carbon atoms; and
each heterocycle is independently: a nonaromatic, saturated or partially unsaturated 3-10 membered monocyclic ring system having 1-3 heteroatoms; a nonaromatic, saturated or partially unsaturated 8-12 membered bicyclic ring system having 1-6 heteroatoms; or a nonaromatic, saturated or partially unsaturated tricyclic ring system having 1-9 heteroatoms; said heteroatoms each independently selected from the group consisting of O, N, S, P and Si.

24. The pharmaceutical composition of claim 23, wherein A is phenyl.

25. The pharmaceutical composition of claim 23, wherein n is 1.

26. The pharmaceutical composition of claim 23, wherein $R^1$ is selected from the group consisting of $C_1$-$C_4$ alkyl, halo, amino and nitro.

27. The pharmaceutical composition of claim 26, wherein $R^1$ is selected from the group consisting of methyl, ethyl, isopropyl, bromo, nitro and dimethylamino.

28. The pharmaceutical composition of claim 23, wherein B is phenyl.

29. The pharmaceutical composition of claim 23, wherein X is —C(O)—.

30. The pharmaceutical composition of claim 23, wherein one of $R^2$ and $R^3$ is hydrogen, and the other is independently selected from the group consisting of heterocycloalkyl and alkoxyalkyl.

31. The pharmaceutical composition of claim 30, wherein one of $R^2$ and $R^3$ is hydrogen, and the other is independently selected from the group consisting of 3-methoxypropyl and oxetan-3-ylmethyl.

32. The pharmaceutical composition of claim 23, wherein the compound of formula (II) is selected from the group consisting of:
4-((1-(4-isopropylbenzyl)-2,4-dioxo-1,2-dihydroquinazolin-3(4H)-yl)methyl)-N-(3-methoxypropyl)benzamide;
N-(3-methoxypropyl)-4-((1-(4-nitrobenzyl)-2,4-dioxo-1,2-dihydroquinazolin-3(4H)-yl)methyl)benzamide;
4-((1-(4-bromobenzyl)-2,4-dioxo-1,2-dihydroquinazolin-3(4H)-yl)methyl)-N-(3-methoxypropyl)benzamide;
4-((1-(4-ethylbenzyl)-2,4-dioxo-1,2-dihydroquinazolin-3(4H)-yl)methyl)-N-(3-methoxypropyl)benzamide;
4-((1-(4-methylbenzyl)-2,4-dioxo-1,2-dihydroquinazolin-3(4H)-yl)methyl)-N-(oxetan-3-ylmethyl)benzamide; and
4-((1-(4-(dimethylamino)benzyl)-2,4-dioxo-1,2-dihydroquinazolin-3(4H)-yl)methyl)-N-(oxetan-3-ylmethyl)benzamide.

33. A compound of formula (III):

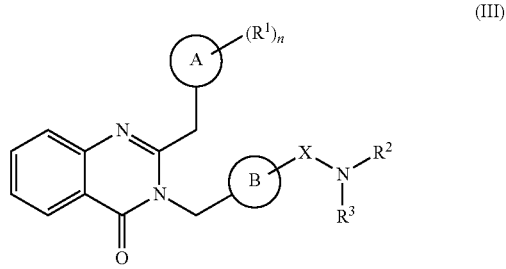

wherein:
A and B are each independently aryl, heteroaryl, cycloalkyl or heterocycle;
n is 0, 1, 2, 3, 4 or 5;
$R^1$ is selected from the group consisting of $C_2$-$C_6$ alkyl, halo, cyano, haloalkyl, amino, alkoxy, —$SO_2H$, —$SO_2NHR'$, $CONHR'$, aryl, heteroaryl, cycloalkyl and heterocycle;
each R' is independently selected from the group consisting of hydrogen and alkyl;
X is a bond, —C(O)—, $CH_2$ and $SO_2$;
$R^2$ and $R^3$ are independently selected from the group consisting of hydrogen, alkyl, haloalkyl, heterocycloalkyl, alkoxyalkyl and aminoalkyl, or $R^2$ and $R^3$ are taken together with the atom to which they are attached to form a heterocyclic ring;
each aryl is independently selected from the group consisting of phenyl, naphthyl and anthracenyl;
each heteroaryl is independently an aromatic 5-8 membered monocyclic ring having 1-3 heteroatoms, an 8-12 membered bicyclic ring having 1-6 heteroatoms, or an aromatic 11-14 membered tricyclic ring system having 1-9 heteroatoms, said heteroatoms each independently selected from the group consisting of O, N, S, P and Si;

each cycloalkyl is independently a non-aromatic, saturated or partially unsaturated cyclic, bicyclic or tricyclic hydrocarbon group having 3 to 12 carbon atoms; and each heterocycle is independently: a nonaromatic, saturated or partially unsaturated 3-10 membered monocyclic ring system having 1-3 heteroatoms; a nonaromatic, saturated or partially unsaturated 8-12 membered bicyclic ring system having 1-6 heteroatoms; or a nonaromatic, saturated or partially unsaturated tricyclic ring system having 1-9 heteroatoms; said heteroatoms each independently selected from the group consisting of O, N, S, P and Si.

34. The compound of claim 33, wherein A is phenyl.

35. The compound of claim 33, wherein n is 1.

36. The compound of claim 33, wherein $R^1$ is selected from the group consisting of $C_2$-$C_4$ alkyl, halo, and amino.

37. The compound of claim 36, wherein $R^1$ is selected from the group consisting of ethyl, isopropyl, bromo, and dimethylamino.

38. The compound of claim 33, wherein B is phenyl.

39. The compound of claim 33, wherein X is —C(O)—.

40. The compound of claim 33, wherein one of $R^2$ and $R^3$ is hydrogen, and the other is independently selected from the group consisting of heterocycloalkyl and alkoxyalkyl.

41. The compound of claim 40, wherein one of $R^2$ and $R^3$ is hydrogen, and the other is independently selected from the group consisting of 3-methoxypropyl and oxetan-3-ylmethyl.

42. The compound of claim 33, wherein the compound of formula (III) is selected from the group consisting of:

4-((1-(4-isopropylbenzyl)-2,4-dioxo-1,2-dihydroquinazolin-3(4H)-yl)methyl)-N-(3-methoxypropyl)benzamide;

4-((1-(4-bromobenzyl)-2,4-dioxo-1,2-dihydroquinazolin-3(4H)-yl)methyl)-N-(3-methoxypropyl)benzamide;

4-((1-(4-ethylbenzyl)-2,4-dioxo-1,2-dihydroquinazolin-3(4H)-yl)methyl)-N-(3-methoxypropyl)benzamide; and 4-((1-(4-(dimethylamino)benzyl)-2,4-dioxo-1,2-dihydroquinazolin-3(4H)-yl)methyl)-N-(oxetan-3-ylmethyl)benzamide.

43. A compound selected from the group consisting of:

4-((1-(4-isopropylbenzyl)-2,4-dioxo-1,2-dihydroquinazolin-3(4H)-yl)methyl)-N-(3-methoxypropyl)benzamide;

4-((1-(4-bromobenzyl)-2,4-dioxo-1,2-dihydroquinazolin-3(4H)-yl)methyl)-N-(3-methoxypropyl)benzamide;

4-((1-(4-ethylbenzyl)-2,4-dioxo-1,2-dihydroquinazolin-3(4H)-yl)methyl)-N-(3-methoxypropyl)benzamide;

4-((1-(4-methylbenzyl)-2,4-dioxo-1,2-dihydroquinazolin-3(4H)-yl)methyl)-N-(oxetan-3-ylmethyl)benzamide; and 4-((1-(4-(dimethylamino)benzyl)-2,4-dioxo-1,2-dihydroquinazolin-3(4H)-yl)methyl)-N-(oxetan-3-ylmethyl)benzamide.

* * * * *